US012573042B2

(12) United States Patent
Lisi et al.

(10) Patent No.: US 12,573,042 B2
(45) Date of Patent: ***Mar. 10, 2026

(54) DIFFERENTIATION DEVICE, DIFFERENTIATION METHOD FOR DEPRESSION SYMPTOMS, DETERMINATION METHOD FOR LEVEL OF DEPRESSION SYMPTOMS, STRATIFICATION METHOD FOR DEPRESSION PATIENTS, DETERMINATION METHOD FOR EFFECTS OF TREATMENT OF DEPRESSION SYMPTOMS, AND BRAIN ACTIVITY TRAINING DEVICE

(71) Applicants: ADVANCED TELECOMMUNICATIONS RESEARCH INSTITUTE INTERNATIONAL, Soraku-gun (JP); HIROSHIMA UNIVERSITY, Higashihiroshima (JP)

(72) Inventors: Giuseppe Lisi, Soraku-gun (JP); Jun Morimoto, Soraku-gun (JP); Mitsuo Kawato, Soraku-gun (JP); Takashi Yamada, Soraku-gun (JP); Naho Ichikawa, Hiroshima (JP); Yasumasa Okamoto, Hiroshima (JP)

(73) Assignees: ADVANCED TELECOMMUNICATIONS RESEARCH INSTITUTE INTERNATIONAL, Soraku-Gun (JP); HIROSHIMA UNIVERSITY, Higashihiroshima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/642,566

(22) Filed: Apr. 22, 2024

(65) Prior Publication Data

US 2024/0354947 A1 Oct. 24, 2024

Related U.S. Application Data

(63) Continuation of application No. 16/753,291, filed as application No. PCT/JP2018/036952 on Oct. 2, 2018, now Pat. No. 12,020,427.

(30) Foreign Application Priority Data

Oct. 3, 2017 (JP) ................................. 2017-193897
Jan. 16, 2018 (JP) ................................. 2018-005110

(51) Int. Cl.
*G06T 7/00* (2017.01)
*A61B 5/055* (2006.01)
(Continued)

(52) U.S. Cl.
CPC .......... *G06T 7/0012* (2013.01); *G06F 18/214* (2023.01); *G06F 18/2431* (2023.01);
(Continued)

(58) Field of Classification Search
None
See application file for complete search history.

(56) References Cited

U.S. PATENT DOCUMENTS 7,353,064 B2 4/2008 Kawasaki et al.
8,386,192 B2 2/2013 Kawasaki et al.
(Continued)

FOREIGN PATENT DOCUMENTS

CN 106407733 A 2/2017
EP 3381361 A1 10/2018
(Continued)

OTHER PUBLICATIONS

U.S. Office Action for U.S. Appl. No. 16/753,291, dated Jul. 19, 2023.
(Continued)

*Primary Examiner* — Mohammed Rachedine
(74) *Attorney, Agent, or Firm* — Birch, Stewart, Kolasch & Birch, LLP

(57) ABSTRACT

Objective discrimination of a disease label of a depressive symptom with respect to an active state of a brain is achieved. One means for solving the problems of the present invention is to provide a discriminating device for assisting in determination of whether a subject has a depressive symptom. The discriminating device includes a storage device for storing information for identifying a classifier generated by classifier generation processing based on a signal obtained by using a brain activity detecting apparatus
(Continued)

to measure, in advance and time-sequentially, a signal indicating a brain activity of a plurality of predetermined regions of each brain of a plurality of participants in a resting state, the plurality of participants including healthy individuals and patients with depression. The classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The discriminating device further includes a processor configured to execute discriminating processing of generating a classification result for the depressive symptom of the subject by using the classifier.

8 Claims, 39 Drawing Sheets

(51) Int. Cl.

| | |
|---|---|
| *G06F 18/214* | (2023.01) |
| *G06F 18/2431* | (2023.01) |
| *G06N 20/00* | (2019.01) |
| *G16H 20/70* | (2018.01) |
| *G16H 30/20* | (2018.01) |
| *G16H 50/30* | (2018.01) |
| *G16H 50/70* | (2018.01) |
| *G16H 70/60* | (2018.01) |

(52) U.S. Cl.

CPC ........... *G06N 20/00* (2019.01); *G06T 7/0014* (2013.01); *G16H 20/70* (2018.01); *G16H 30/20* (2018.01); *G16H 50/30* (2018.01); *G16H 50/70* (2018.01); *G16H 70/60* (2018.01); *A61B 5/055* (2013.01); *G06T 2207/10088* (2013.01); *G06T 2207/20081* (2013.01); *G06T 2207/30016* (2013.01)

(56) References Cited

U.S. PATENT DOCUMENTS

| | | | |
|---|---|---|---|
| 8,861,815 | B2 | 10/2014 | Cecchi et al. |
| 9,101,276 | B2 | 8/2015 | Georgopoulos |
| 9,265,441 | B2 | 2/2016 | Pereira et al. |
| 9,454,641 | B2 | 9/2016 | Cecchi et al. |
| 9,480,402 | B2 | 11/2016 | Leuthardt et al. |
| 9,510,756 | B2 | 12/2016 | Grady et al. |
| 9,612,306 | B2 | 4/2017 | Lin et al. |
| 9,632,162 | B2 | 4/2017 | Matthews |
| 10,357,181 | B2 | 7/2019 | Morimoto et al. |
| 11,382,556 | B2 | 7/2022 | Lisi et al. |
| 11,521,641 | B2 | 12/2022 | Ando et al. |
| 11,666,219 | B2 | 6/2023 | Fox |
| 2002/0103429 | A1 | 8/2002 | deCharms |
| 2004/0116798 | A1 | 6/2004 | Cancro et al. |
| 2005/0215884 | A1 | 9/2005 | Greicius et al. |
| 2006/0241382 | A1 | 10/2006 | Li et al. |
| 2007/0055118 | A1 | 3/2007 | Kawasaki et al. |
| 2009/0118652 | A1 | 5/2009 | Kawasaki et al. |
| 2009/0124886 | A1 | 5/2009 | Wang et al. |
| 2010/0249573 | A1 | 9/2010 | Marks |
| 2011/0119212 | A1 | 5/2011 | De Bruin et al. |
| 2012/0201320 | A1 | 8/2012 | Koike-Akino |
| 2013/0034277 | A1 | 2/2013 | Cecchi et al. |
| 2013/0102918 | A1 | 4/2013 | Etkin et al. |
| 2013/0116540 | A1 | 5/2013 | Li et al. |
| 2013/0211229 | A1 | 8/2013 | Rao et al. |
| 2013/0231552 | A1 | 9/2013 | Grady et al. |
| 2014/0002075 | A1 | 1/2014 | Lin et al. |
| 2014/0058189 | A1* | 2/2014 | Stubbeman ........... A61M 21/02 |
| | | | 600/13 |
| 2014/0107494 | A1 | 4/2014 | Kato et al. |
| 2014/0171757 | A1 | 6/2014 | Kawato et al. |
| 2014/0336998 | A1 | 11/2014 | Cecchi et al. |
| 2014/0343399 | A1* | 11/2014 | Posse ................... A61B 5/7203 |
| | | | 600/410 |
| 2014/0371573 | A1* | 12/2014 | Komoto ............... A61B 5/4064 |
| | | | 600/411 |
| 2015/0018664 | A1 | 1/2015 | Pereira et al. |
| 2015/0160322 | A1 | 6/2015 | Matthews |
| 2015/0174362 | A1 | 6/2015 | Panova et al. |
| 2015/0248615 | A1 | 9/2015 | Parra et al. |
| 2015/0272461 | A1 | 10/2015 | Morimoto et al. |
| 2015/0294074 | A1* | 10/2015 | Kawato .................. A61B 5/375 |
| | | | 702/19 |
| 2016/0019693 | A1* | 1/2016 | Silbersweig ........... G06T 11/60 |
| | | | 382/128 |
| 2017/0042474 | A1 | 2/2017 | Widge et al. |
| 2017/0071522 | A1 | 3/2017 | Parsey et al. |
| 2017/0340212 | A1 | 11/2017 | Lin et al. |
| 2018/0098738 | A1 | 4/2018 | Sutoko et al. |
| 2019/0090749 | A1 | 3/2019 | Leuthardt et al. |
| 2019/0298207 | A1 | 10/2019 | Morimoto et al. |
| 2019/0328782 | A1 | 10/2019 | Braithwaite et al. |
| 2019/0374154 | A1 | 12/2019 | Wendling et al. |
| 2019/0392348 | A1 | 12/2019 | Ando et al. |
| 2020/0077947 | A1 | 3/2020 | Shi et al. |
| 2020/0163609 | A1 | 5/2020 | Lisi et al. |
| 2021/0015366 | A1 | 1/2021 | Agrawal |
| 2021/0034912 | A1 | 2/2021 | Lisi et al. |

FOREIGN PATENT DOCUMENTS

| | | | | |
|---|---|---|---|---|
| JP | | 2006-513742 | A | 4/2006 |
| JP | | 2008-178546 | A | 8/2008 |
| JP | | 2011-184 | A | 1/2011 |
| JP | | 2012-165370 | A | 8/2012 |
| JP | | 2013-218725 | A | 10/2013 |
| JP | | 2014-84567 | A | 5/2014 |
| JP | | 5641531 | B1 | 12/2014 |
| JP | | 2015-62817 | A | 4/2015 |
| JP | | 2015-112474 | A | 6/2015 |
| JP | | 6195329 | B1 | 9/2017 |
| JP | | 2017-196523 | A | 11/2017 |
| JP | | 2018-89142 | A | 6/2018 |
| JP | | 2019-63478 | A | 4/2019 |
| JP | | 2019-516950 | A | 6/2019 |
| JP | | 2019-198376 | A | 11/2019 |
| JP | | 2020-24139 | A | 2/2020 |
| WO | | 2005/025421 | A1 | 3/2005 |
| WO | | 2006/102370 | A2 | 9/2006 |
| WO | | 2006/132313 | A1 | 12/2006 |
| WO | | 2007/014467 | A1 | 2/2007 |
| WO | WO 2011/038124 | A2 | 3/2011 |
| WO | WO 2011/115956 | A1 | 9/2011 |
| WO | WO 2012/083136 | A1 | 6/2012 |
| WO | WO 2012/165602 | A1 | 12/2012 |
| WO | WO 2013/069517 | A1 | 5/2013 |
| WO | WO-2014059234 | A1 * | 4/2014 | ............. G16H 50/70 |
| WO | WO-2014121146 | A1 * | 8/2014 | ............. G16H 50/50 |
| WO | WO 2014/178323 | A1 | 11/2014 |
| WO | WO-2015070324 | A2 * | 6/2015 | ......... A61N 1/36067 |
| WO | WO-2015149170 | A1 * | 10/2015 | ........... A61N 1/0534 |
| WO | WO-2015164882 | A1 * | 10/2015 | .......... A61B 5/4893 |
| WO | WO-2015187247 | A2 * | 12/2015 | ........... A61B 5/4827 |
| WO | WO-2016023126 | A1 * | 2/2016 | ......... A61B 5/14542 |
| WO | WO 2016/203456 | A1 | 12/2016 |
| WO | WO 2017/090590 | A1 | 6/2017 |
| WO | WO 2017/162773 | A1 | 9/2017 |
| WO | WO 2018/147193 | A1 | 8/2018 |
| WO | WO 2019/069955 | A1 | 4/2019 |

OTHER PUBLICATIONS

U.S. Office Action for U.S. Appl. No. 17/914,398, dated Feb. 26, 2025.

(56) References Cited

OTHER PUBLICATIONS

U.S. Office Action for U.S. Appl. No. 18/016,161, dated Sep. 12, 2025.

Wallace et al., "Class Imbalance, Redux," 2011 11th IEEE International Conference on Data Mining, 2011, pp. 754-763.

Yamada et al., "Resting-State Functional Connectivity-Based Biomarkers and Functional MRI-Based Neurofeedback for Psychiatric Disorders: A Challenge for Developing Theranostic Biomarkers," International Journal of Neuropsychopharmacology, vol. 20, No. 10, 2017, pp. 769-781.

"Distance correlation", Wikipedia, retrieved on Jun. 21, 2022, https://en.wikipedia.org/wiki/Distance_correlation.

"r—How to do classification after clustering?—Cross Validated," Feb. 28, 2017, XP093099851, retrieved from the Internet, URL: <https://stats.stackexchange.com/questions/264312/how-to-do-classification-after-clustering>.

Anderson et al., "Functional connectivity magnetic resonance imaging classification of autism," Brain, vol. 134, 2011, pp. 3739-3751.

Baldassarre et al., "Structured Sparsity Models for Brain Decoding from fMRI data," Second International Workshop on Pattern Recognition in NeuroImaging, 2012, pp. 5-8.

Behzadi et al., "A component based noise correction method (CompCor) for BOLD and perfusion based fMRI", Neuroimage, 2007, 37(1), pp. 90-101.

Blei et al., "Variational inference for Dirichlet process mixtures", Bayesian analysis, 2006, 1(1), pp. 121-144.

Breiman, "Random Forests", Machine Learning, 2001, 45, pp. 5-32.

Buckner et al., "The Brain's Default Network Anatomy, Function, and Relevance to Disease," Ann. N.Y. Acad. Sci, vol. 1124, 2008, pp. 1-38.

Dadi et al., "Benchmarking functional connectome-based predictive models for resting-state fMRI", Preprint submitted to NeuroImage, Jan. 14, 2019.

De Charms et al., "Control over brain activation and pain learned by using real-time functional MRI", PNAS, Dec. 20, 2005, vol. 102, No. 51, pp. 18626-18631 (6 pages).

Dinga et al., "Evaluating the evidence for biotypes of depression: Methodological replication and extension of Drysdale et al. (2017)", NeuroImage: Clinical, 2019, 22, 101796, total 11 pages.

Drysdale et al., "Resting-state connectivity biomarkers define neurophysiological subtypes of depression", Nature Medicine, Jan. 2017, vol. 23, No. 1, total 16 pages.

Extended European Search Report for European Application No. 21785099.9, dated Apr. 3, 2024.

Extended European Search Report for European Application No. 21842607.0, dated Nov. 22, 2023.

Final Office Action issued in copending U.S. Appl. No. 14/439,145 on Sep. 7, 2018.

Finn et al., "Functional connectome fingerprinting: identifying individuals based on patterns of brain connectivity", Nat Neurosci, 2015, 18(11), pp. 1664-1671.

Fukuda et al., "Decoded Neurofeedback ni yoru Seishin Shikkan Chiryo no Kanosei," Experimental Medicine, vol. 30, No. 13 (special extra), Aug. 1, 2012, pp. 182 (2162)-187 (2167) with English translation (10 pages total).

Glasser et al., "A multi-modal parcellation of human cerebral cortex", Nature, 2016, 536(7615), pp. 171-178.

Glasser et al., "The Human Connectome Project's Neuroimaging Approach", Nat Neurosci., 2016, 19(9), pp. 1175-1187.

Guan et al., "Sparse Representation based Discriminative Canonical Correlation Analysis for Face Recognition," 11th International Conference on Machine Learning and Applications, 2012, pp. 51-56.

Guan et al., "Variational inference for nonparametric multiple clustering", In:MultiClust Workshop, KDD-2010, 2010.

Hampson et al., "Real-time fMRI Biofeedback Targeting the Orbitofrontal Cortex for Contamination Anxiety," Journal of Visualized Experiments, Issue 59, e3535, Jan. 20, 2012, pp. 1-10 (11 pages).

Hardoon et al. "Unsupervised Analysis of fMRI Data Using Kernel Canonical Correlation", Neuroimage, Elsevier, vol. 37, No. 4, Sep. 14, 2007, pp. 1250-1259.

Hardoon et al., "Sparse canonical correlation analysis," Mach Learn, vol. 83, 2011 (published online Nov. 6, 2010), pp. 331-353.

Ichikawa et al., "Identifying melancholic depression biomarker using whole-brain functional connectivity", arXiv:1704.01039 [q-bio.NC], Apr. 3, 2017, V1, 24 pages.

International Search Report (PCT/ISA/210), issued in PCT/JP2021/014254, dated Jun. 15, 2021.

Japan Agency for Medical Research and Development, "AI-based Endoscopy Diagnostic Support Program Approved—to be Used to Assist Physicians in Diagnosis-", Press Release, Dec. 10, 2018, https://www.amed.go.jp/news/release_20181210.html.

Jensen, "Sur les fonctions convexes et les inégalités entre les valeurs moyennes", Acta Mathematica, 1905, 30(1), pp. 175-193.

Johnson et al., "Adjusting batch effects in microarray expression data using empirical Bayes methods" Biostatistics, 2007, 8, 1, pp. 118-127.

Kamitani et al., "Decoding the visual and subjective contents of the human brain", Nat Neurosci., May 2005, vol. 8, No. 5, pp. 679-685 (18 pages).

Kubo, "Data kaiseki no tameno toukei modeling nyu'mon" (Introduction to statistical modeling for data analysis), Iwanami shoten, 1st edition 2012, 14th edition, 2017.

Li et al., "Group Study of Simulated Driving fMRI Data by Multiset Canonical Correlation Analysis", Journal of Signal Processing Systems, vol. 68, 2012, pp. 31-48.

Madeira et al., "Biclustering algorithms for biological data analysis: a survey", IEEE Transactions on Computational Biology and Bioinformatics, 2004, vol. 1, No. 1, pp. 24-45.

Murphy, "Machine Learning: A Probabilistic Perspective", Cambridge, Massachusetts: MIT Press, 2012.

Noble et al., "Multisite reliability of MR-based functional connectivity", Neuroimage, 2017, 146, pp. 959-970.

Oldfield, "The Assessment and Analysis of Handedness: The Edinburgh Inventory". Neuropsychologia, vol. 9, 1971, pp. 97-113.

Pearlson, "Multisite collaborations and large databases in psychiatric neuroimaging advantages, problems, and challenges", Schizophr Bull, 2009, vol. 35, No. 1, pp. 1-2.

Perrot et al., "Cortical sulci recognition and spatial normalization", Medical Image Analysis, vol. 15, 2011, pp. 529-550.

Raichle et al., "A default mode of brain function", PNAS, Jan. 16, 2001, vol. 98, No. 2, pp. 676-682 (7 pages).

Rosenberg et al., "A neuromarker of sustained attention from whole-brain functional connectivity", Nat Neurosci, 2016, 19(1), pp. 165-171.

Ryali et al., "Sparse logistic regression for whole-brain classification of fMRI data," NeuroImage, vol. 51, 2010 (published online Feb. 24, 2010), pp. 752-764.

Santos et al., "On the Use of the Adjusted Rand Index as a Metric for Evaluating Supervised Classification", ICANN 2009, 2009, Part II, LNCS 5769, pp. 175-184.

Schonfelder et al., "Sparse regularized regression identifies behaviorally-relevant stimulus features from psychophysical data", The Journal of the Acoustical Society of America, vol. 131, No. 5, May 2012, pp. 3953-3969.

Shen et al., "Groupwise whole-brain parcellation from resting-state fMRI data for network node identification", Neuroimage, 2013, 82, pp. 403-415.

Shibata et al., "Perceptual learning incepted by decoded fMRI neurofeedback without stimulus presentation", Life Science Shinchaku Ronbun Review, [online], Nov. 1, 2012, [retrieval date May 15, 2014], Internet <URL:http://first.lifesciencedb.jp/archives/4093>, 6 pages.

Shibata et al., "Perceptual Learning Incepted by Decoded fMRI Neurofeedback Without Stimulus Presentation", Science, vol. 334, Dec. 9, 2011, pp. 1413-1415.

Shirer et al., "Decoding Subject-Driven Cognitive States with Whole-Brain Connectivity Patterns," Cerebral Cortext, vol. 22, Jan. 2012, pp. 158-165.

Sun et al., "Canonical Correlation Analysis for Multilabel Classification: A Least-Squares Formulation, Extensions, and Analysis,"

(56)        References Cited

OTHER PUBLICATIONS

IEEE Transactions on Pattern Analysis and Machine Intelligence, vol. 33, No. 1, Jan. 2011, pp. 194-200.

Székely et al., "Measuring and testing dependence by correlation of distances", Ann. Statist., 2007, vol. 35, No. 6, pp. 2769-2794.

Tokuda et al., "Identification of depression subtypes and relevant brain regions using a data-driven approach", Scientific Reports, 2018, 8:14082, DOI:10.1038/s41598-018-32521-z, total 13 pages.

Tokuda et al., "Multiple co-clustering based on nonparametric mixture models with heterogeneous marginal distributions", Plos One, Oct. 19, 2017, pp. 1-29.

Tzourio-Mazoyer et al., "Automated Anatomical Labeling of Activations in SPM Using a Macroscopic Anatomical Parcellation of the MNI MRI Single-Subject Brain", NeuroImage, vol. 15, 2002, pp. 273-289.

Van den Heuvel et al., "Functionally Linked Resting-State Networks Reflect the Underlying Structural Connectivity Architecture of the Human Brain," Human Brain Mapping, vol. 30, 2009, pp. 3127-3141.

Van Dijk et al., "Intrinsic Functional Connectivity as a Tool For Human Connectomics: Theory, Properties, and Optimization," J. Neurophsyiol, vol. 103, 2010, pp. 297-321.

Vounou et al., "Sparse reduced-rank regression detects genetic associations with voxel-wise longitudinal phenotypes in Alzheimer's disease," Elsevier, NeuroImage, vol. 60, No. 1, 2012 (available online Dec. 22, 2011), pp. 700-716.

Wang et al., "Extracting Multiscale Pattern Information of fMRI Based Functional Brain Connectivity with Applicaiton on Classification of Autism Spectrum Disorders," PLoS One, vol. 7, Issue 10, Oct. 2012, pp. 1-14.

Watanabe et al., "Greater plasticity in lower-level than higher-level visual motion processing in a passive perceptual learning task", Nature Neuroscience, vol. 5, 2002, pp. 1-7.

Weiskopf, "Real-time fMRI and its applicatin to neurofeedback", Neuroimage, 2012 (published online Oct. 14, 2001), vol. 62, pp. 682-692 (11 pages).

Whitfield-Gabrieli et al., "Default Mode Network Activity and Connectivity in Psychopathology," Annu. Rev. Clin. Psychol., vol. 8, 2012, pp. 49-76.

Witten et al., "A penalized matrix decomposition, with applications to sparse principal components and canonical correlation analysis", Biostatistics, vol. 10, No. 3, 2009, pp. 515-534.

Written Opinion of the International Searching Authority (PCT/ISA/237), issued in PCT/JP2021/014254, dated Jun. 15, 2021.

Wu et al., "The relationship between the dorsolateral prefrontal cortex and depressive disorders," Journal of International Psychiatry, vol. 42, No. 1, 2015, pp. 73-76, with an English abstract.

Yahata et al., "A small number of abnormal brain connections predicts adult autism spectrum disorder", Nat Commun, 2016, 7, 11254.

Yahata et al., "Computational Neuroscience Approach to Biomarkers and Treatments for Mental Disorders," Psychiatry and Clinical Neurosciences, vol. 71, 2017, pp. 215-237.

Yahata et al., "A Small number of Abnormal Brain Connections Predicts Adult Autism Spectrum Disorder," Nature Communications, vol. 7, Apr. 14, 2016, pp. 1-12.

Yamashita et al., "Harmonization of resting-state functional MRI data across multiple imaging sites via the separation of site differences into sampling bias and measurement bias", PLOS Biology, Apr. 18, 2019, pp. 1-34.

Yamashita et al., "Sparse estimation automatically selects voxels relevant for the decoding of fMRI activity patterns", NeuroImage, vol. 42, No. 4, Oct. 1, 2008, pp. 1-32.

Zeng et al., "Unsupervised Classification of Major Depression Using Functional Connectivity MRI," Human Brain Mapping, vol. 35, 2014, pp. 1630-1641.

Zotev et al., "Self-Regulation of Amygdala Activation Using Real-Time fMRI Neurofeedback," PLoS One, vol. 6, Issue 9, Sep. 2011, pp. 1-17.

* cited by examiner

[Fig. 1]
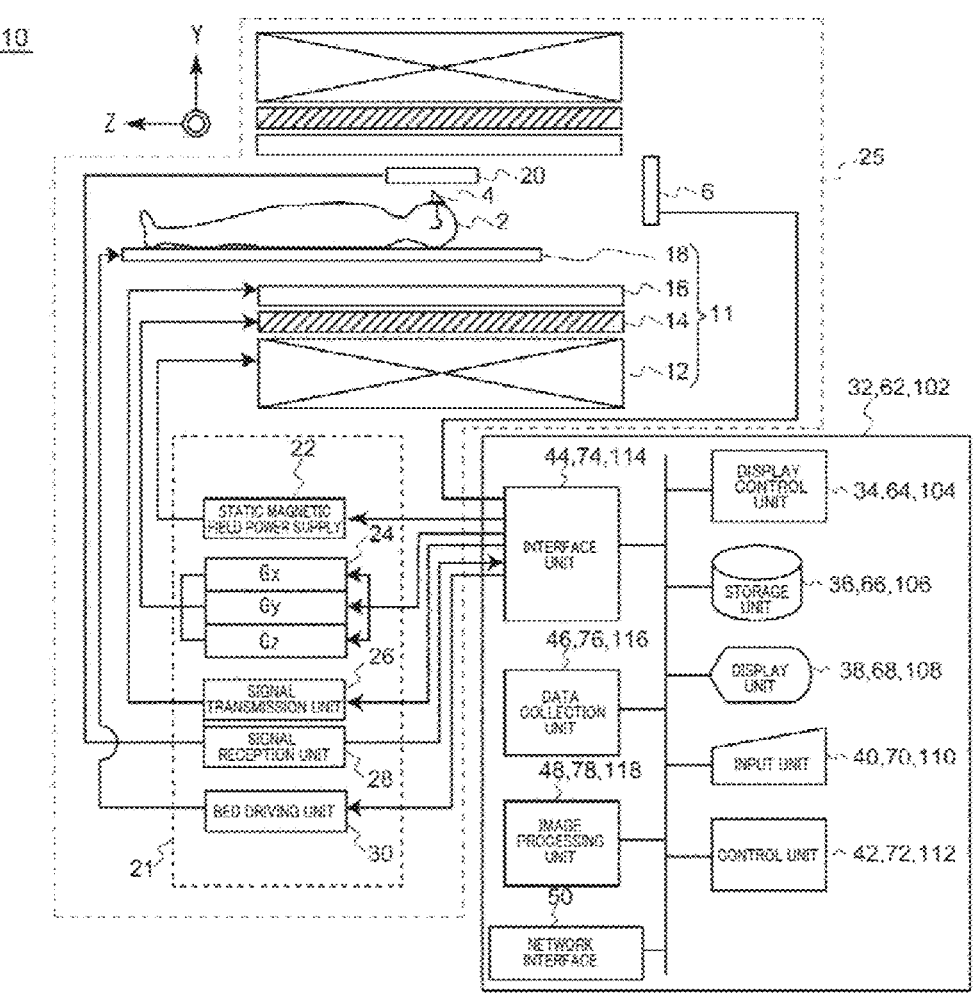

[Fig. 2]
<u>32,62,102</u>
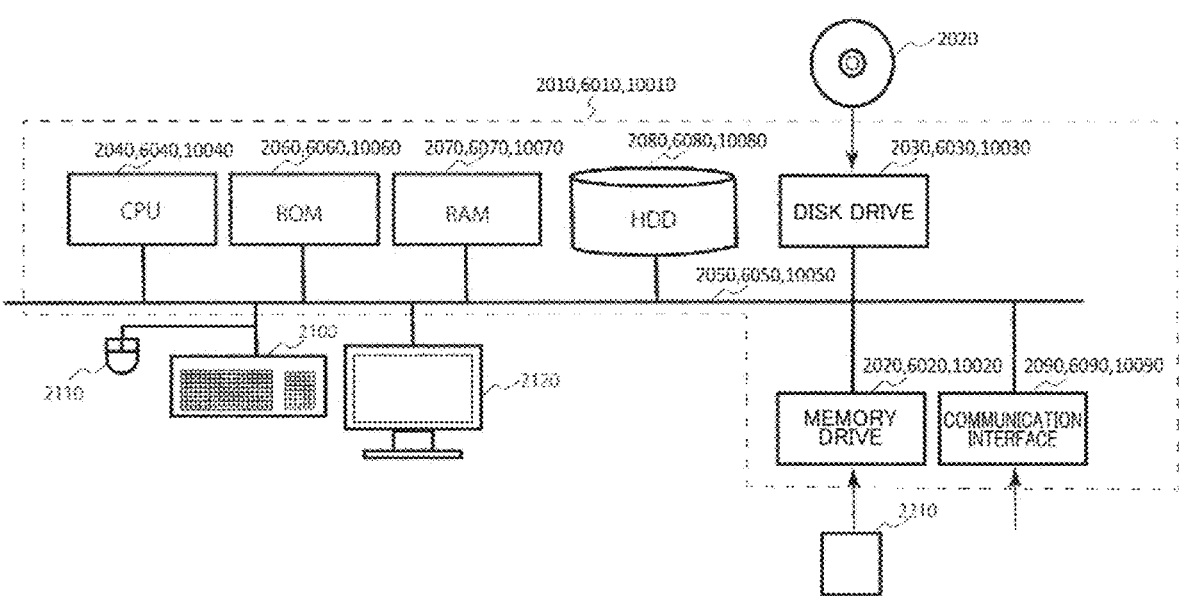

[Fig. 3]
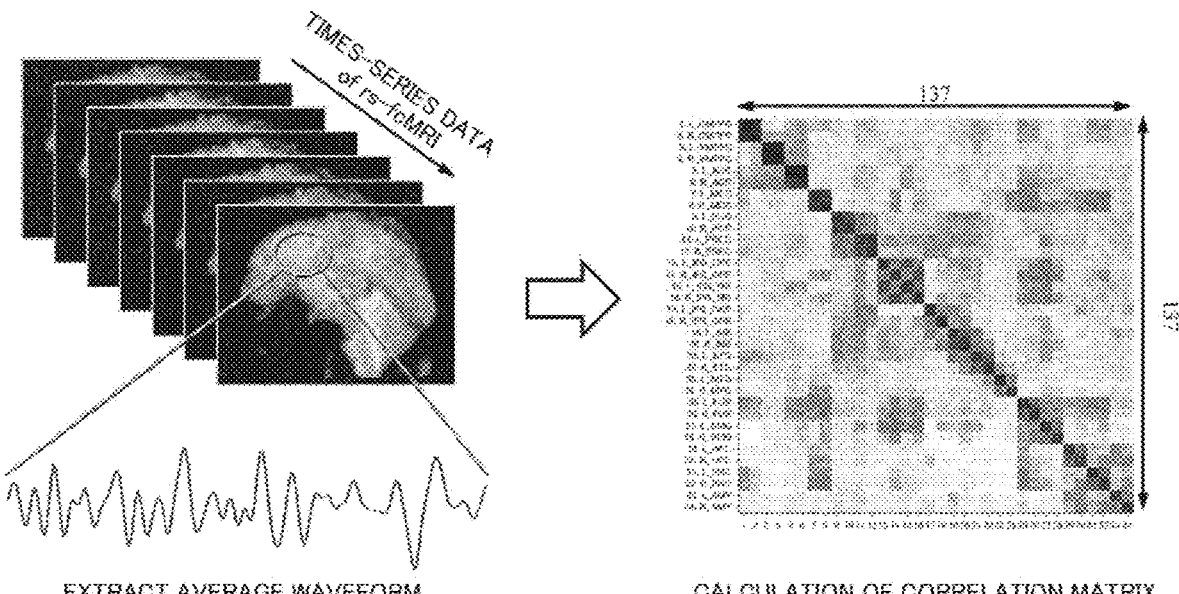
EXTRACT AVERAGE WAVEFORM
IN EACH REGION OF INTEREST
CALCULATION OF CORRELATION MATRIX
AMONG 137 REGIONS

[Fig. 4]
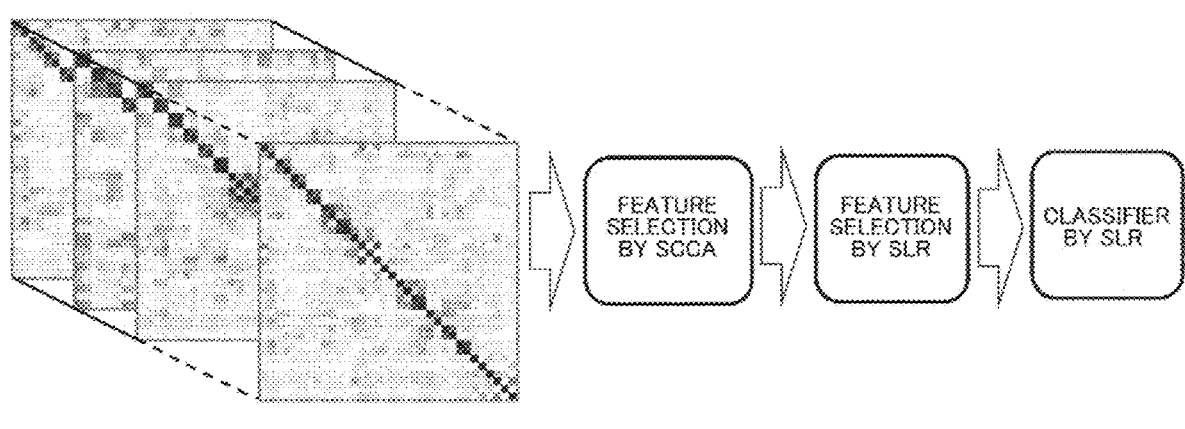
CORRELATION MATRIX

[Fig. 5]
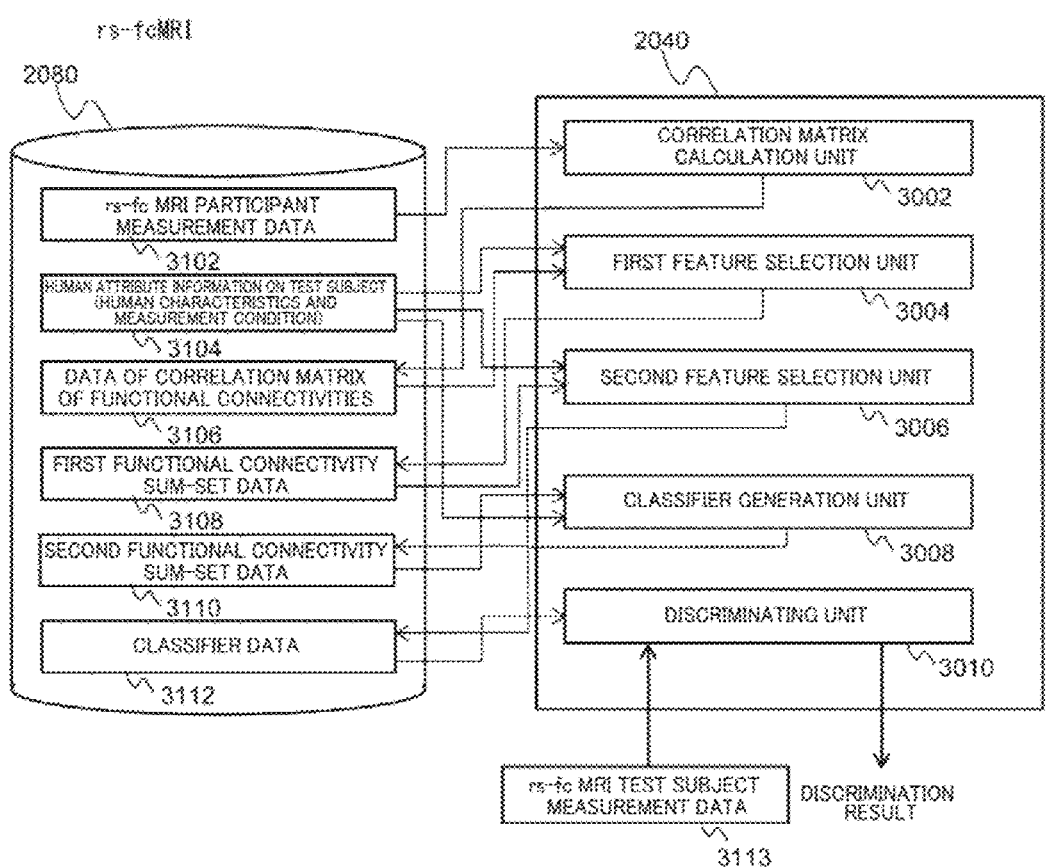

[Fig. 6]
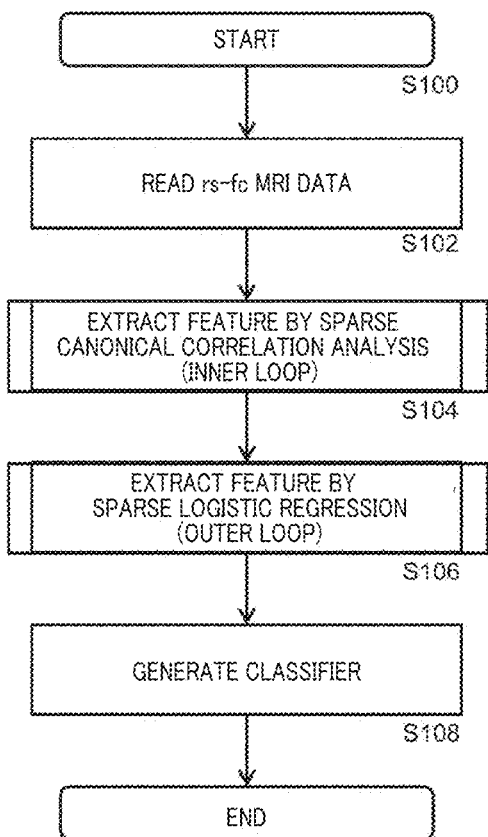

[Fig. 7]
INNER LOOP FEATURE EXTRACTION
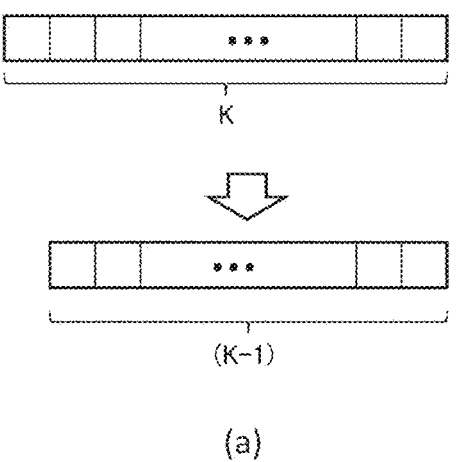
(a)
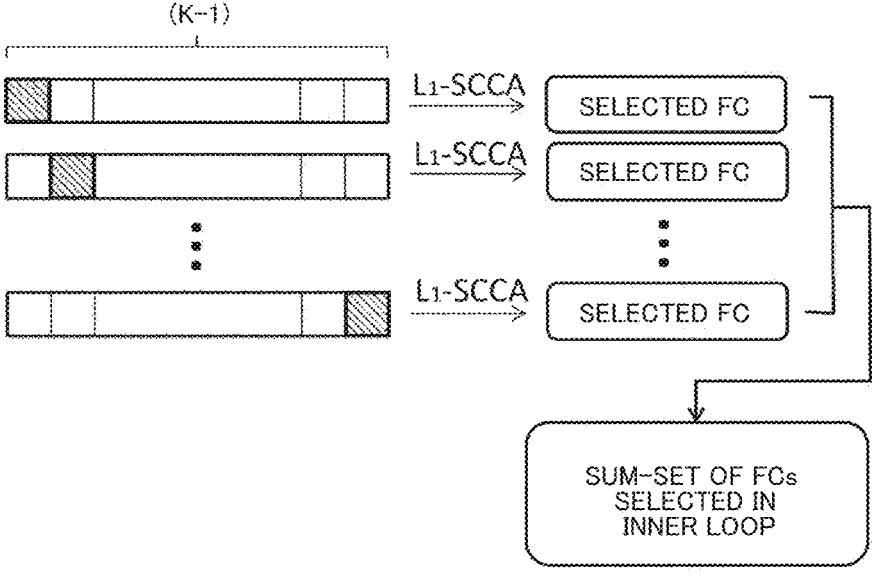
(b)

[Fig. 8]
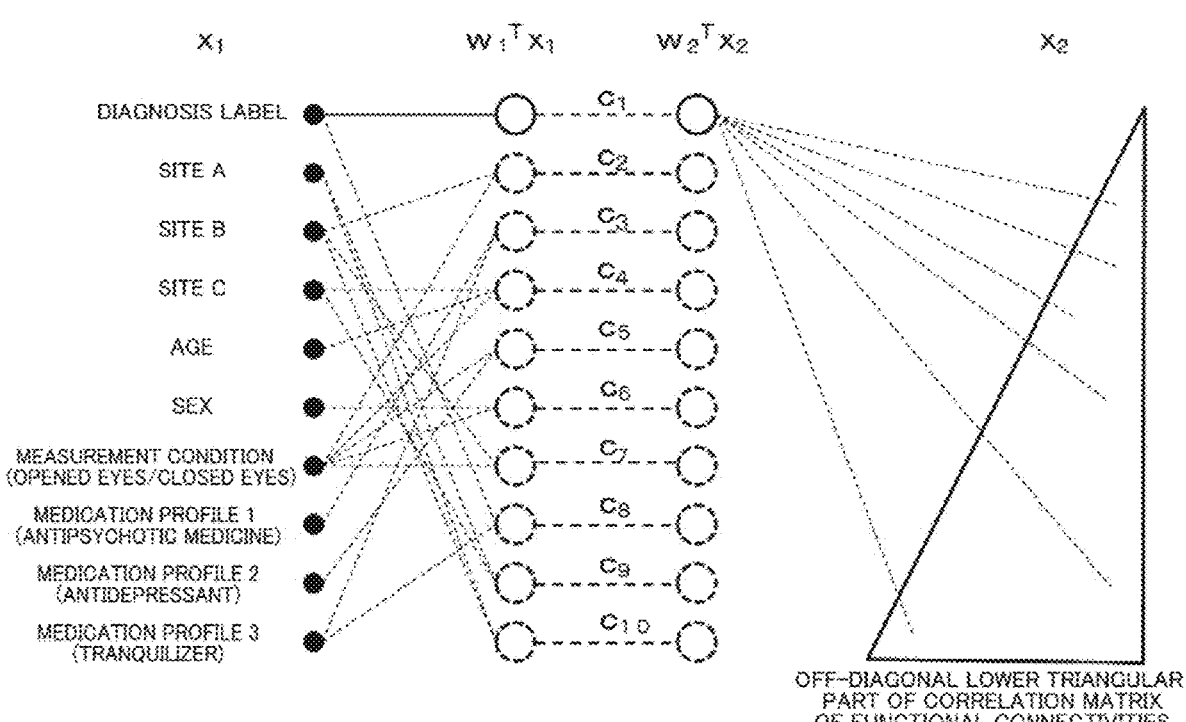
OFF-DIAGONAL LOWER TRIANGULAR
PART OF CORRELATION MATRIX
OF FUNCTIONAL CONNECTIVITIES

[Fig. 9]
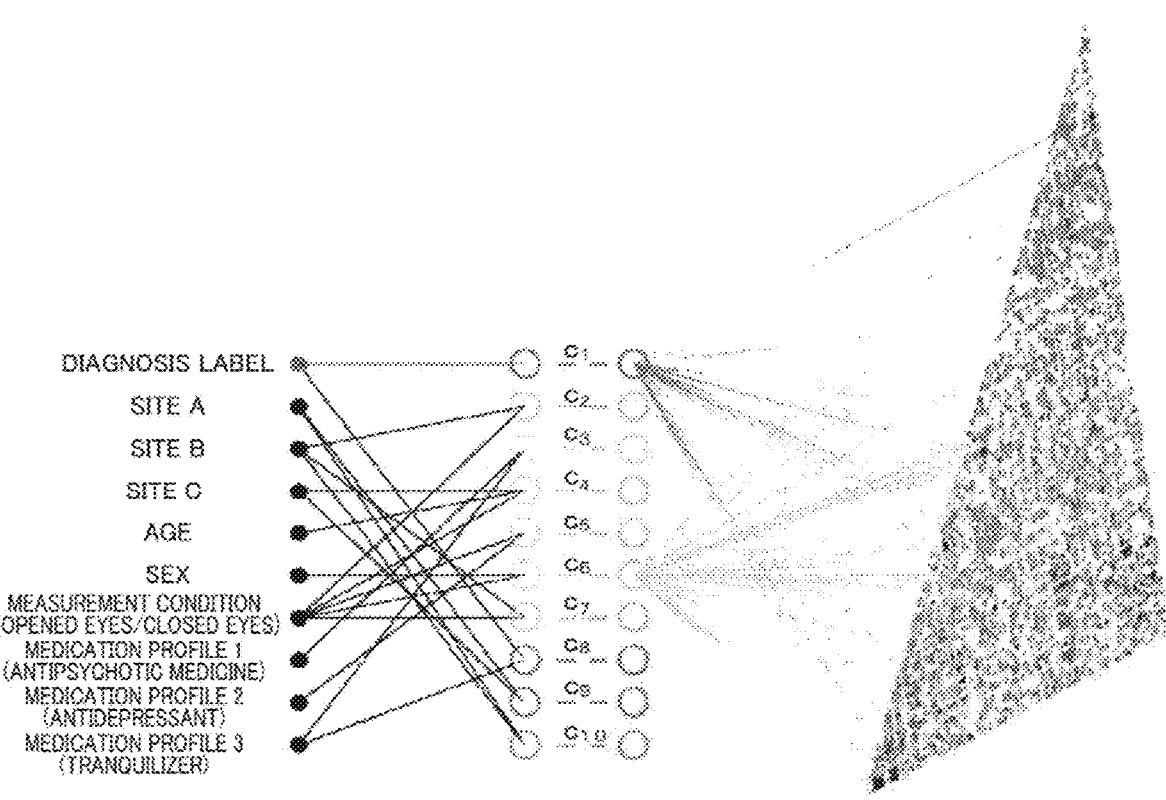

[Fig. 10]
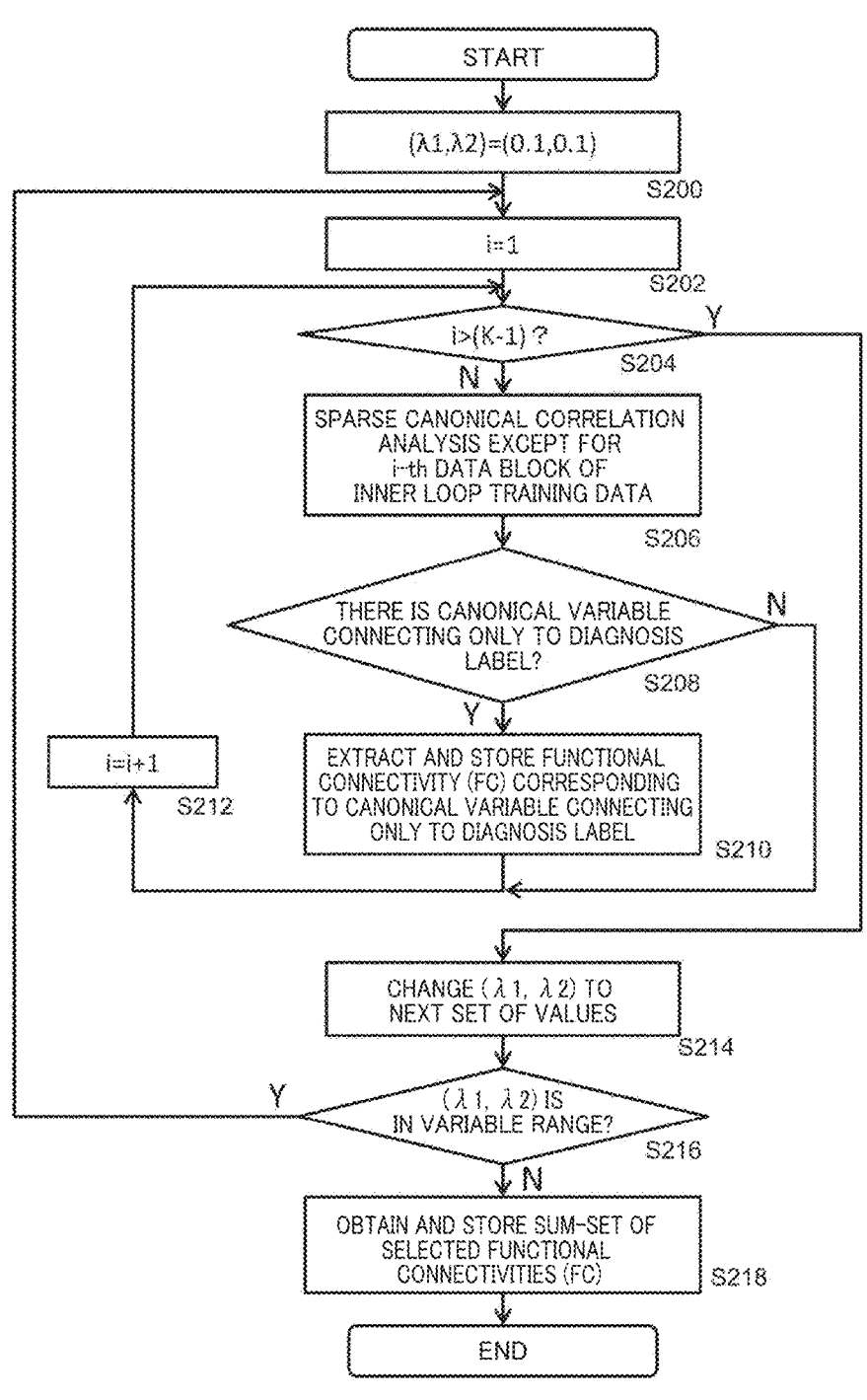

[Fig. 11]
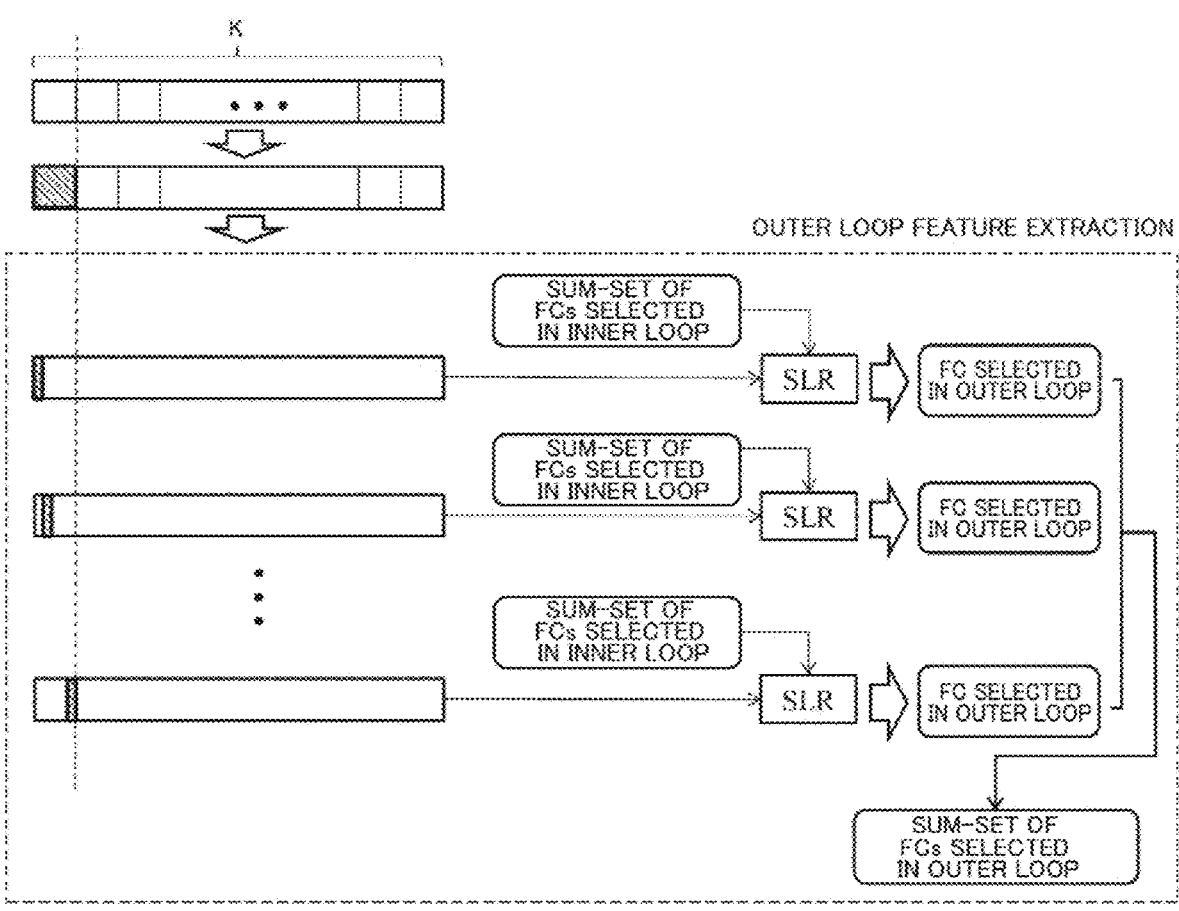

[Fig. 12]
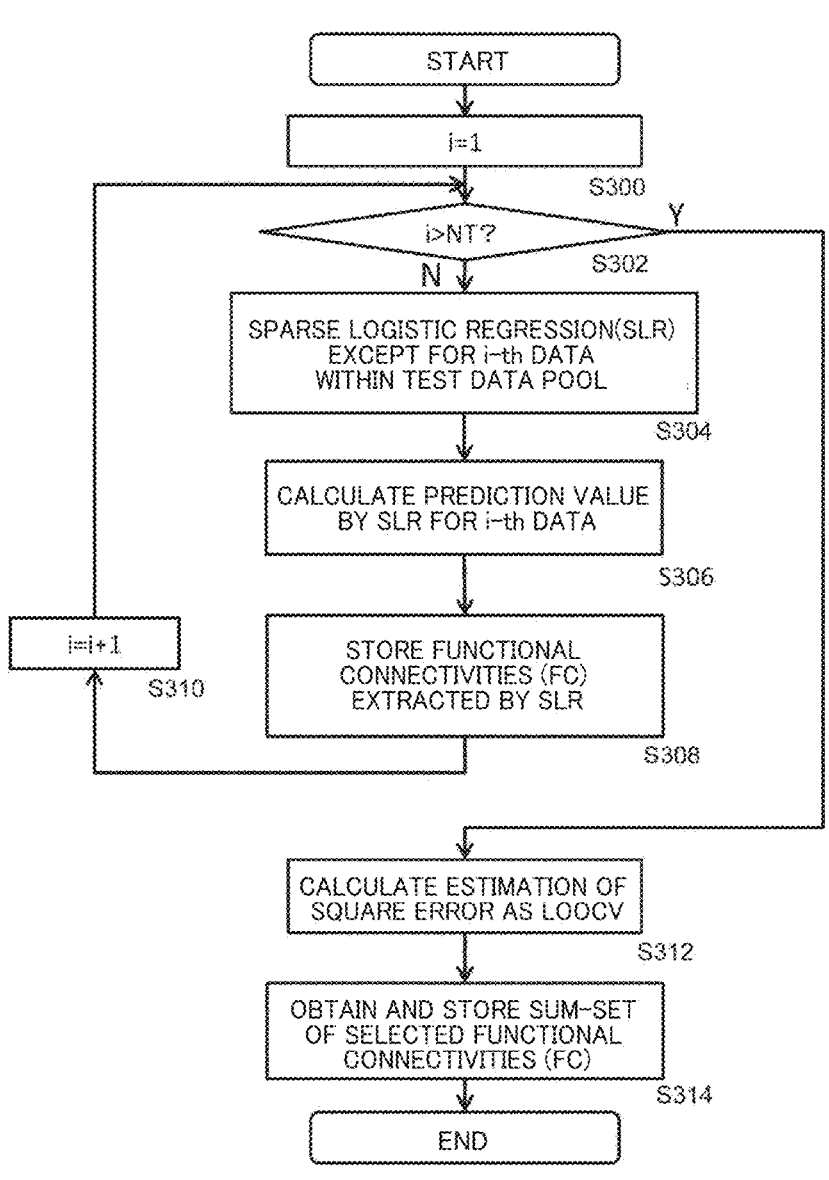

[Fig. 13]
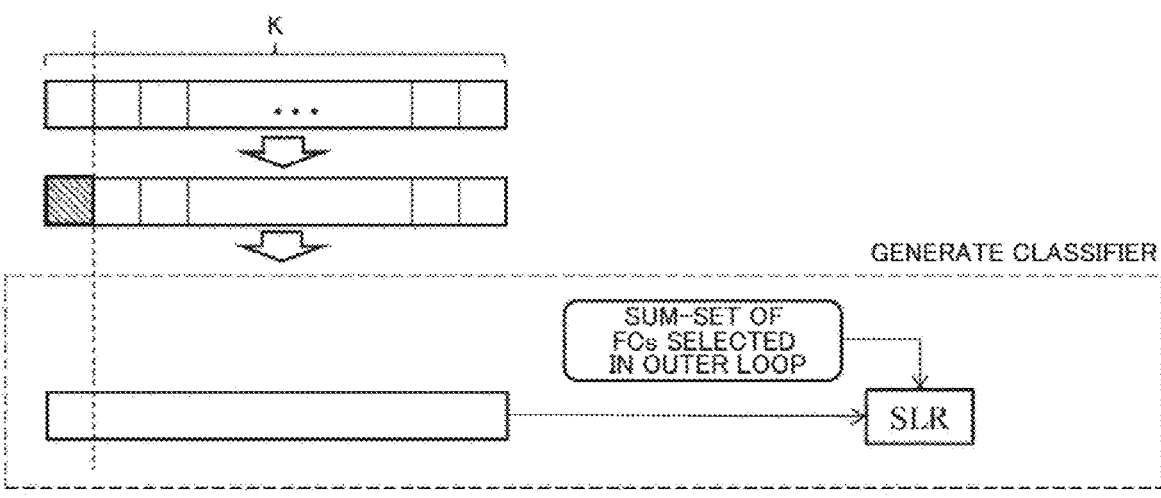

[Fig. 14]
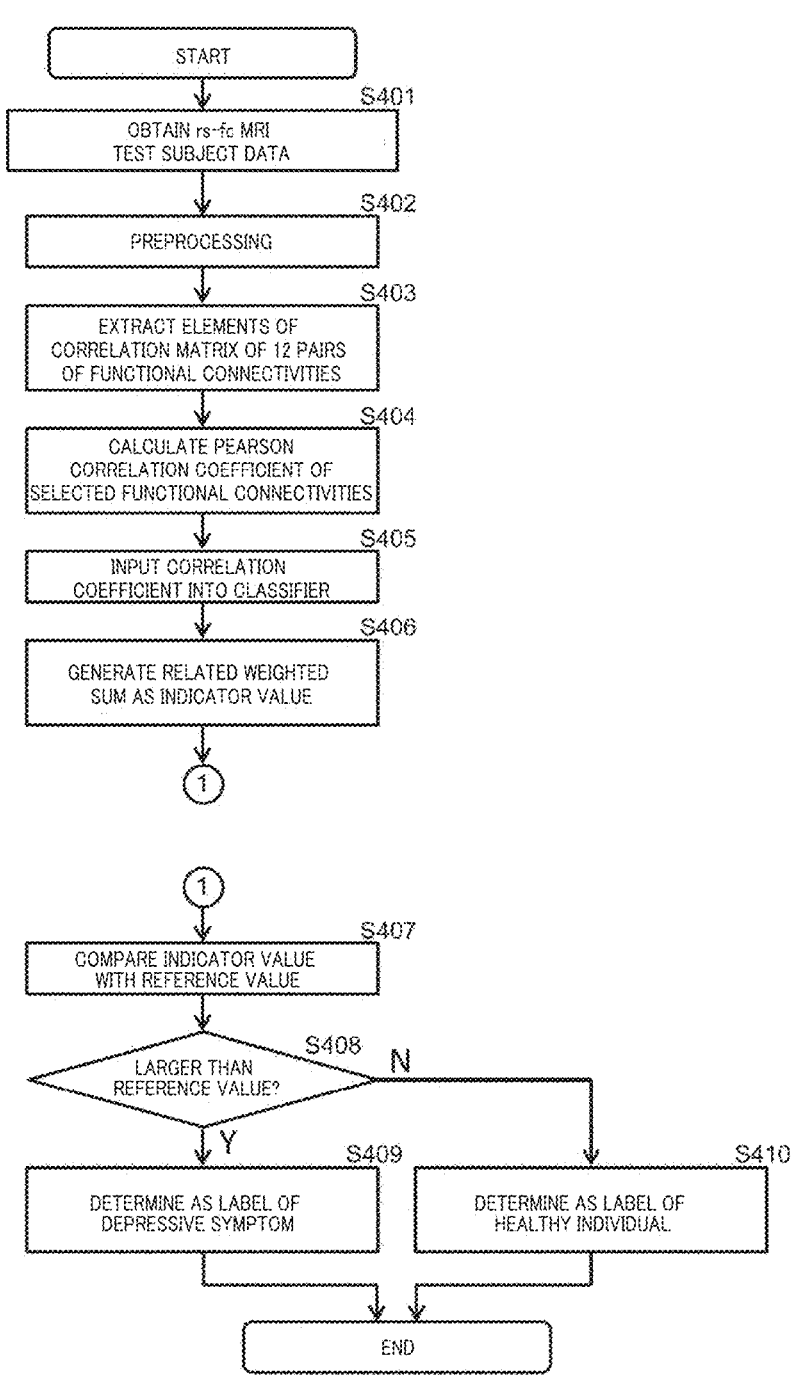

[Fig. 15]
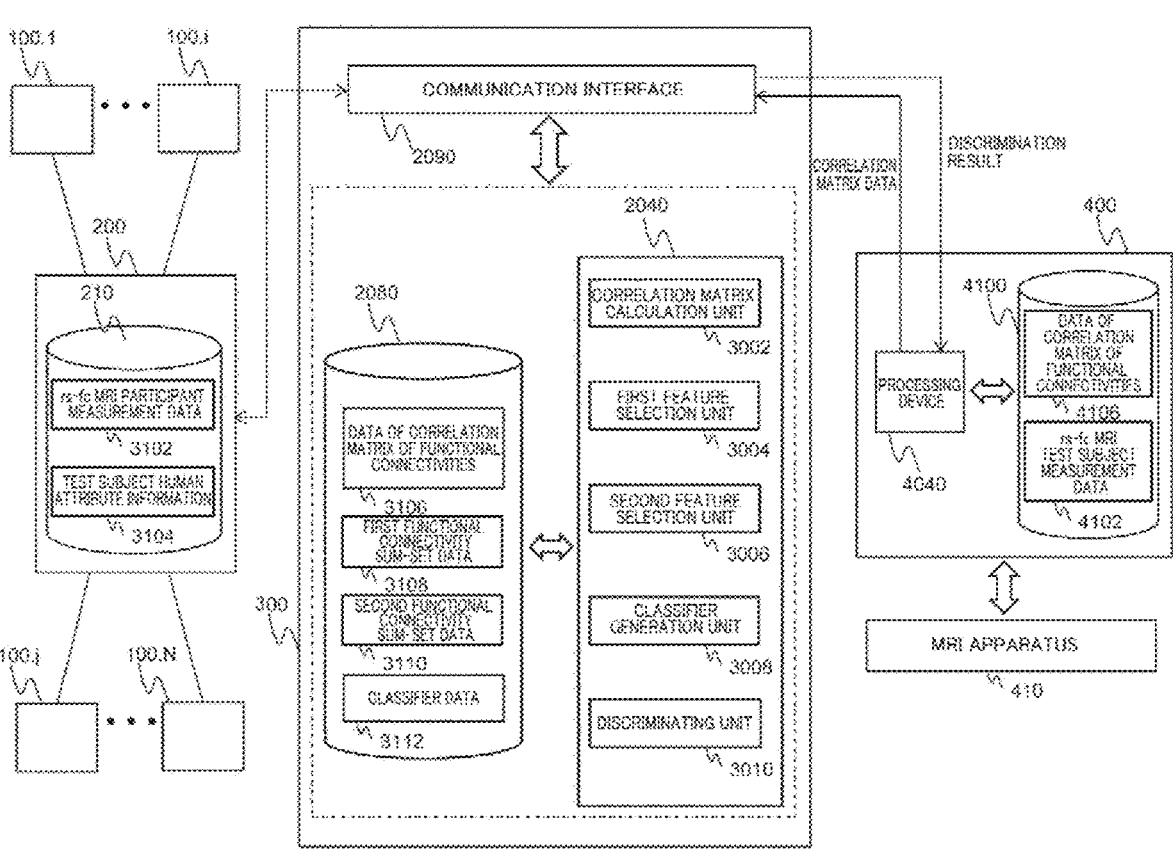

[Fig. 16]
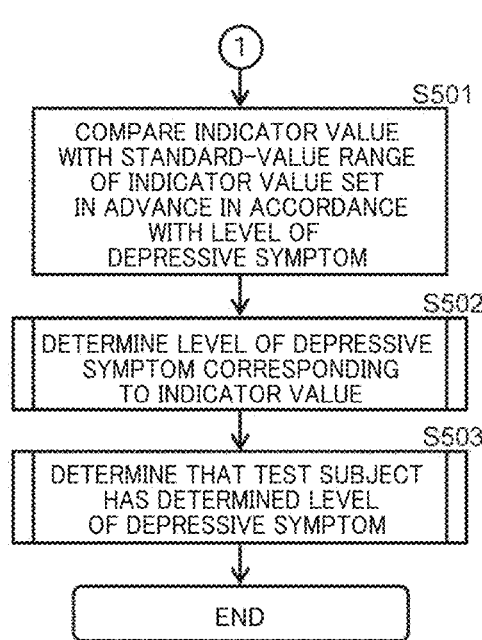

[Fig. 17-1]
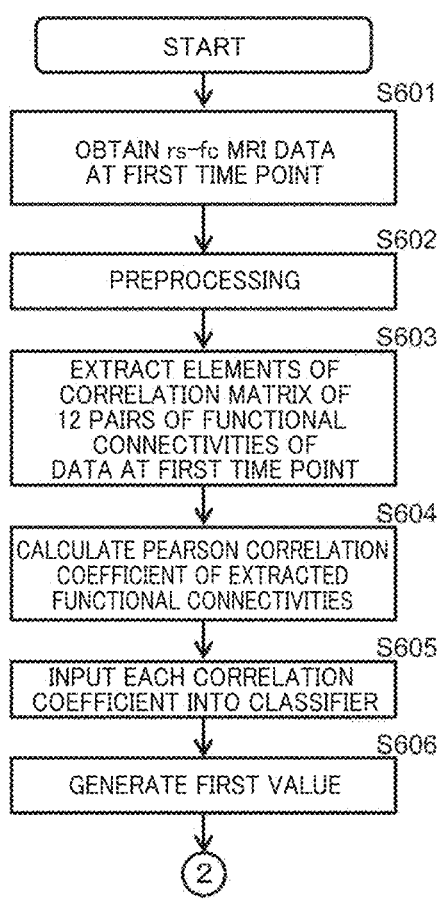

[Fig. 17-2]
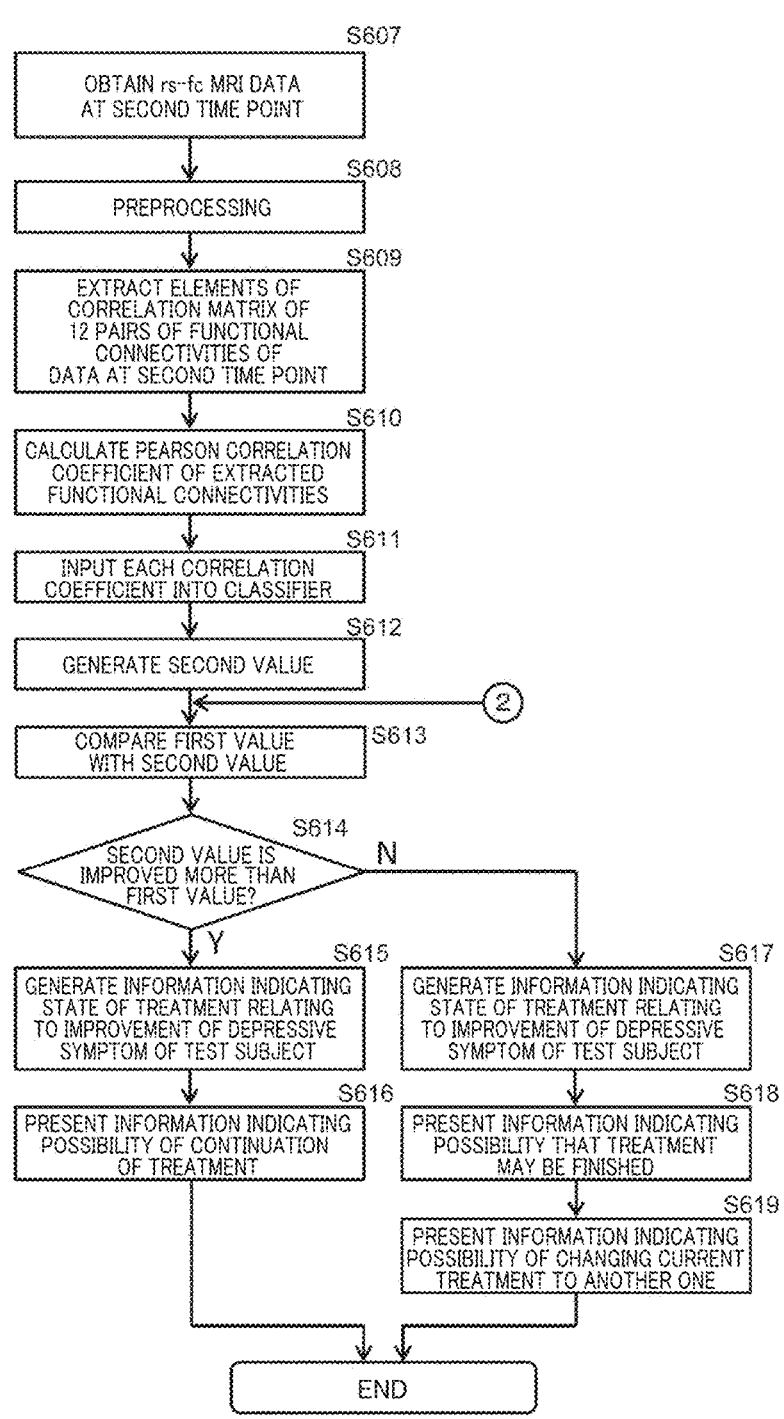

[Fig. 18]
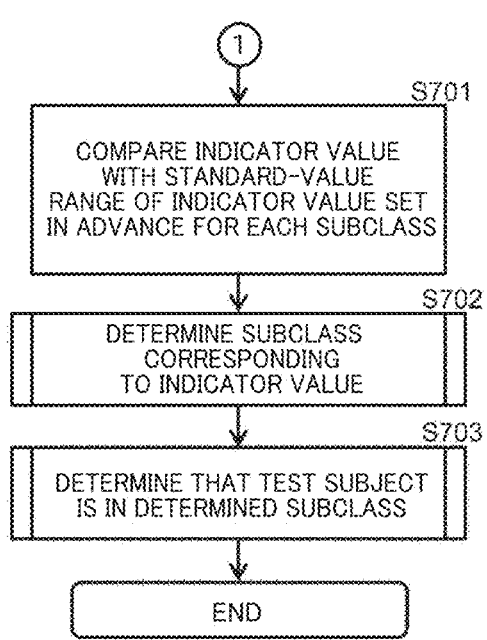

[Fig. 19]
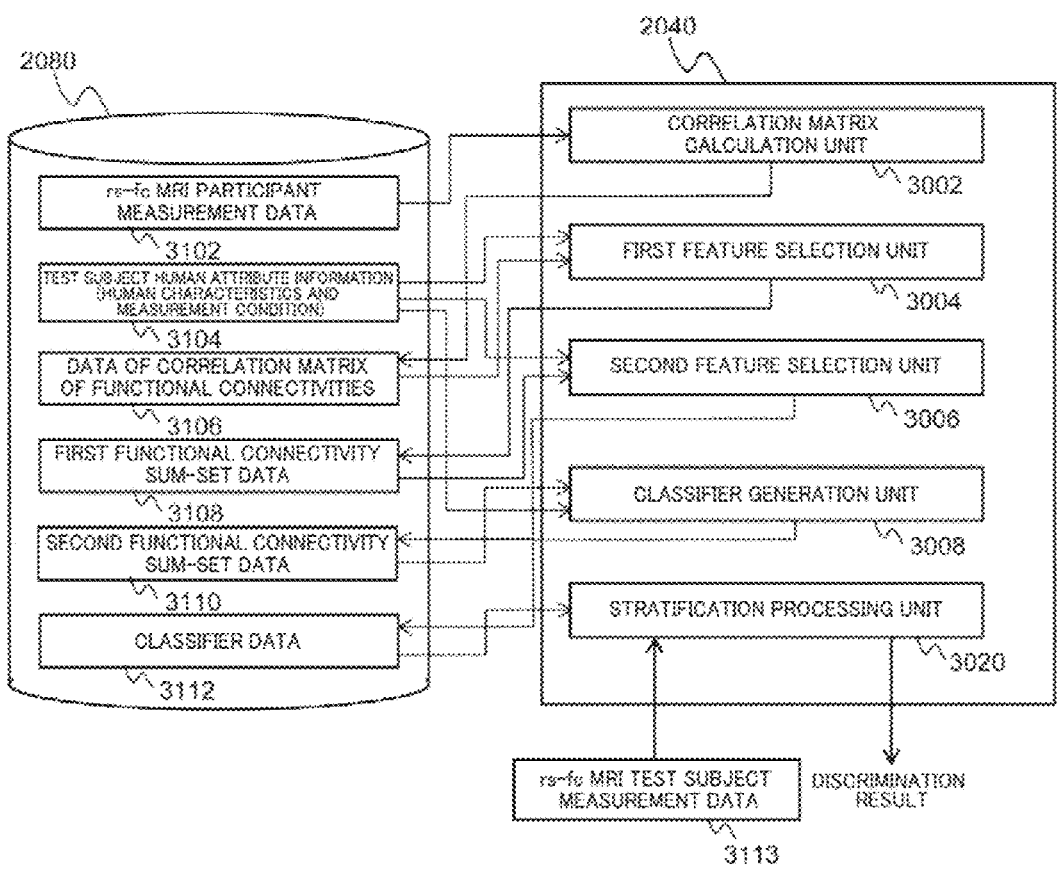

[Fig. 20]

[Fig. 21]
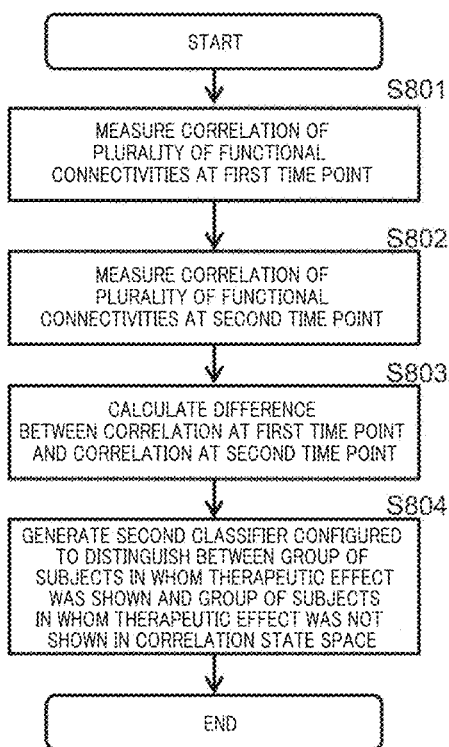

[Fig. 22]
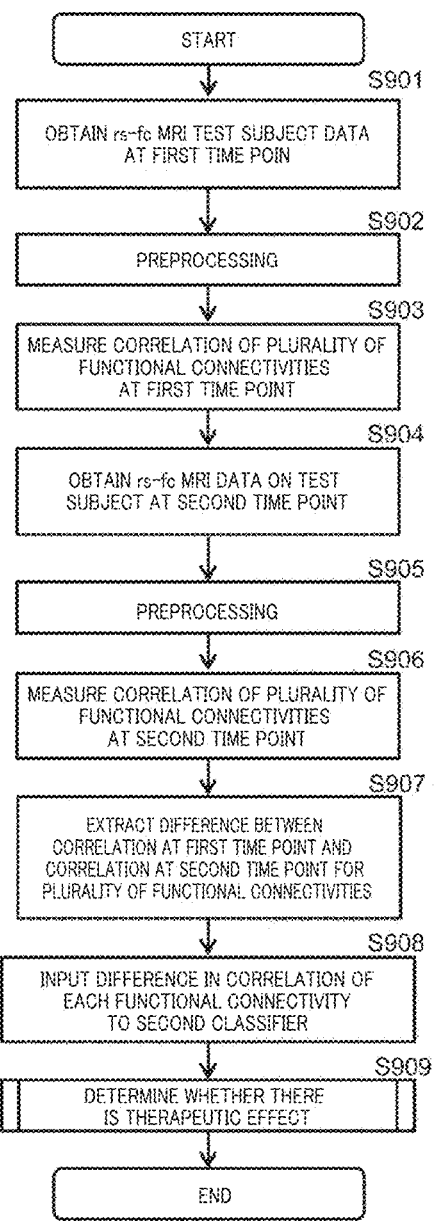

[Fig. 23]
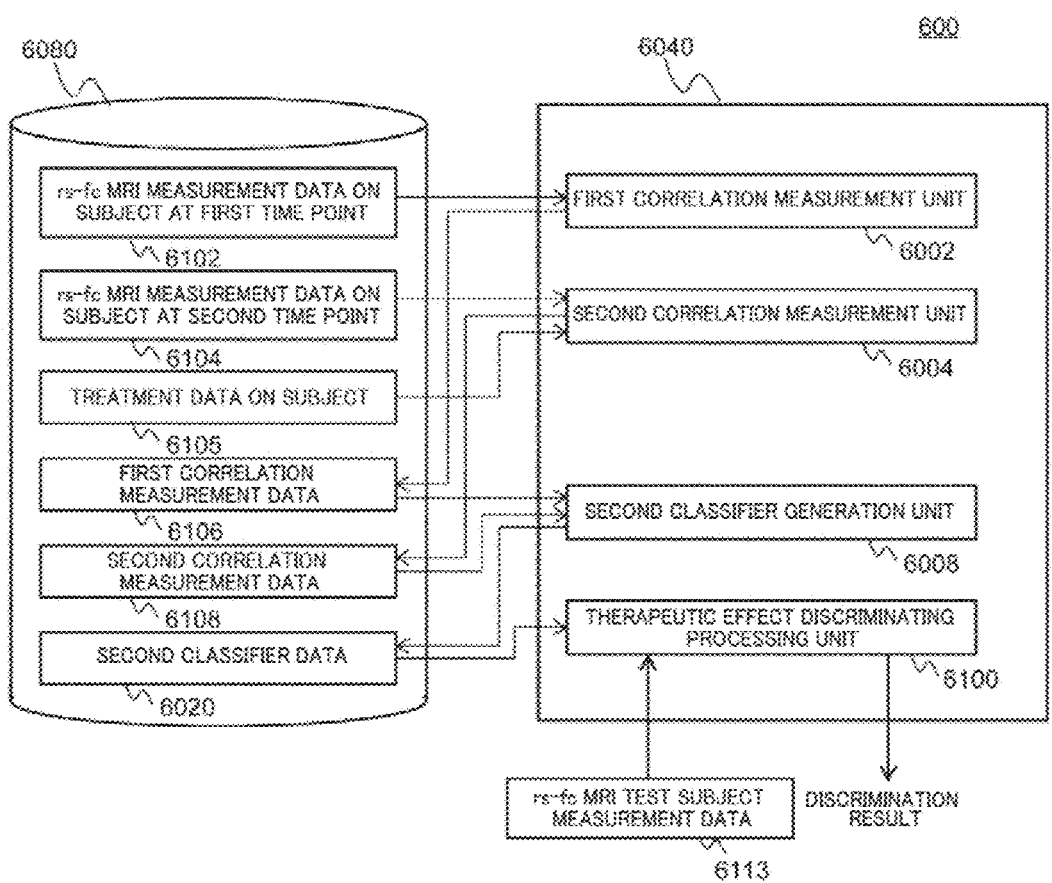

[Fig. 24]
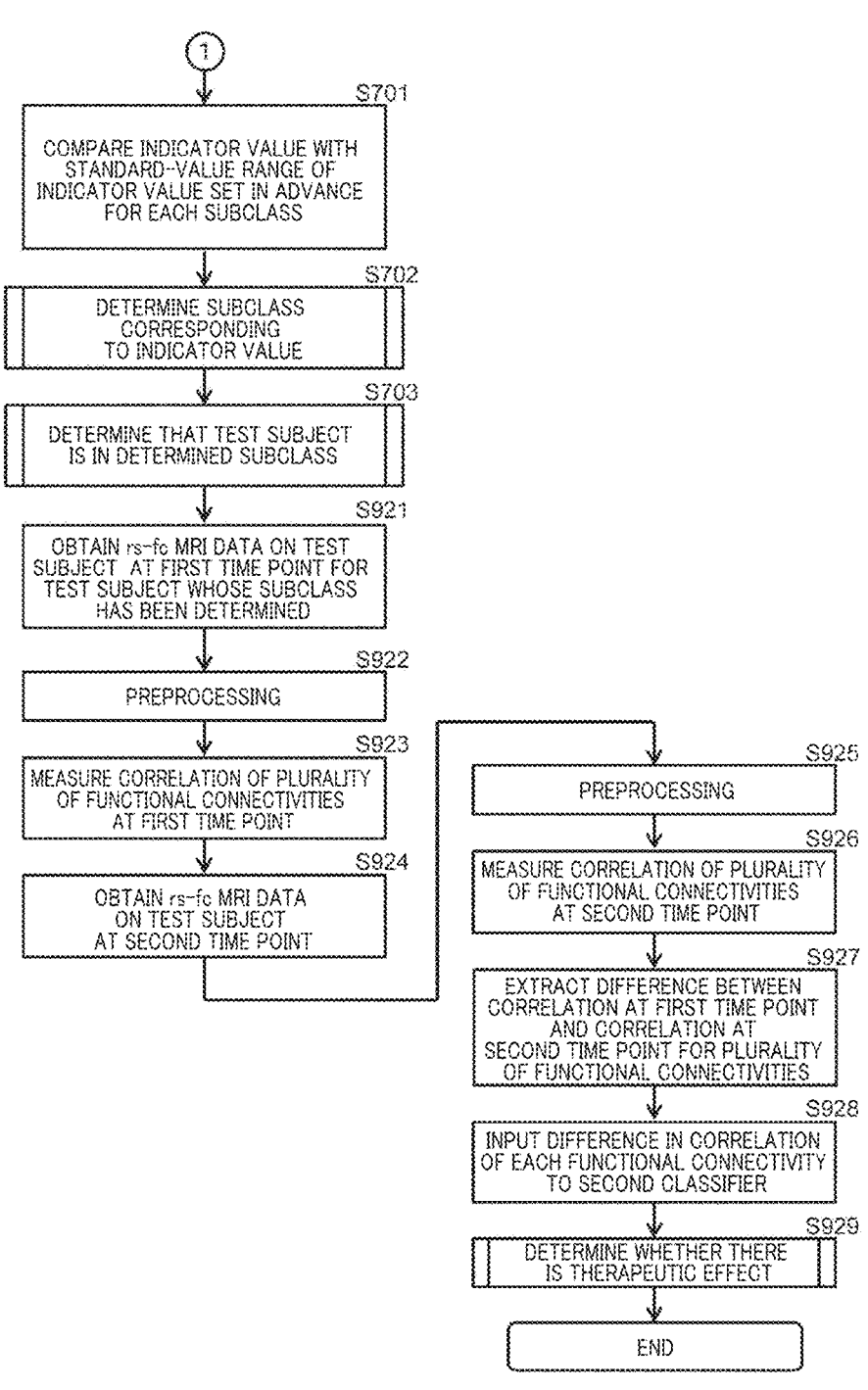

[Fig. 25]
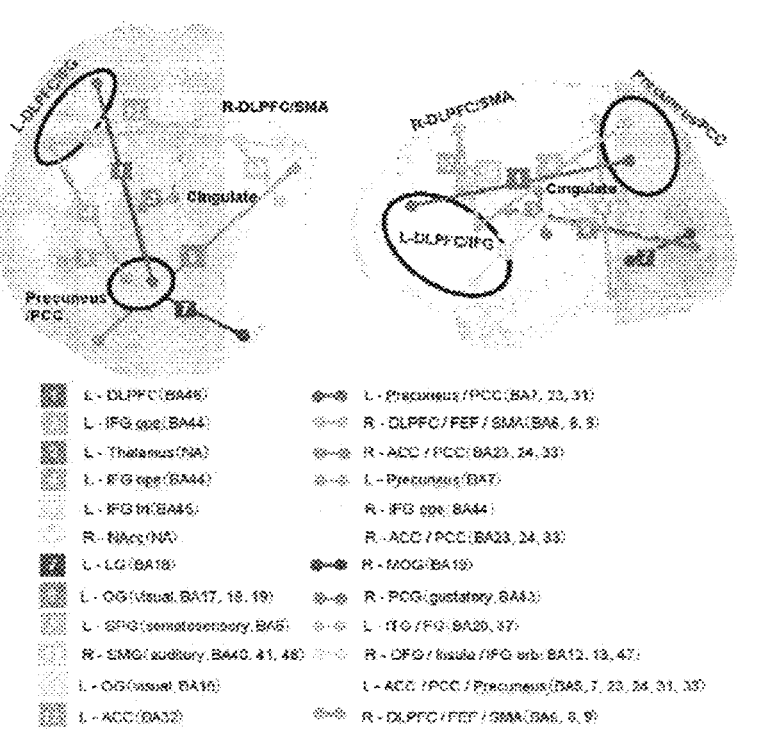
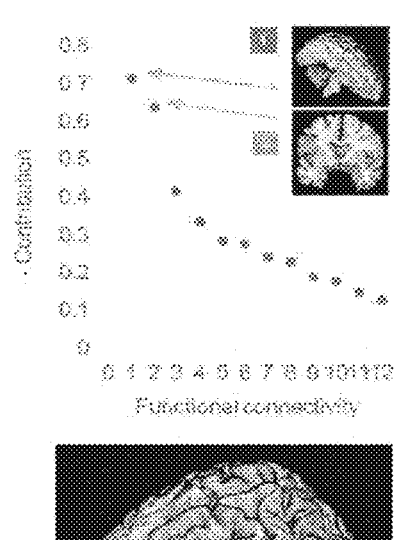
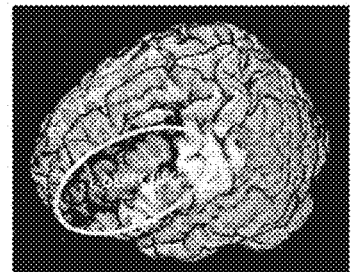

[Fig. 26]
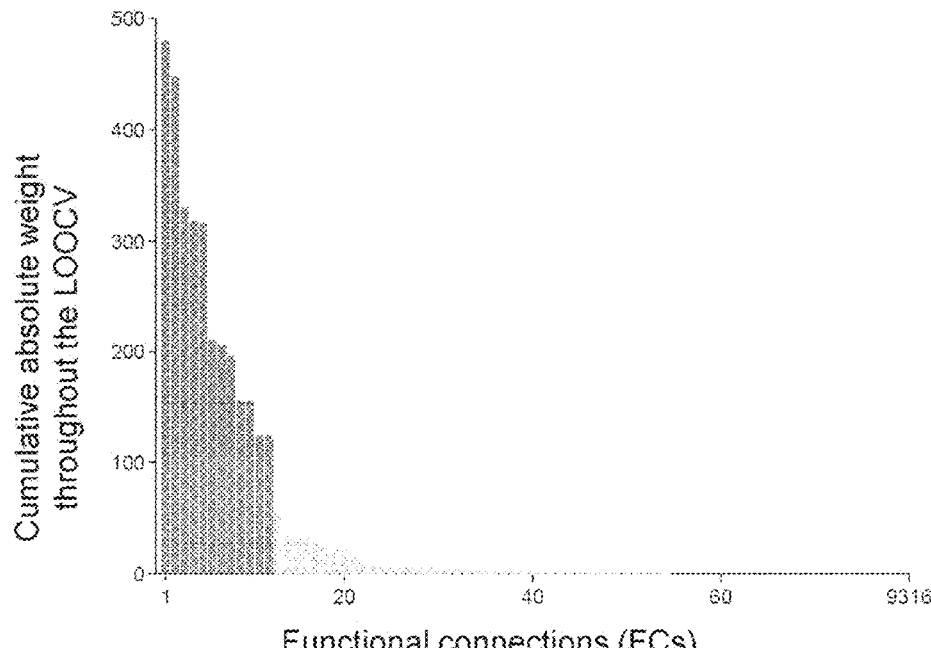

[Fig. 27]

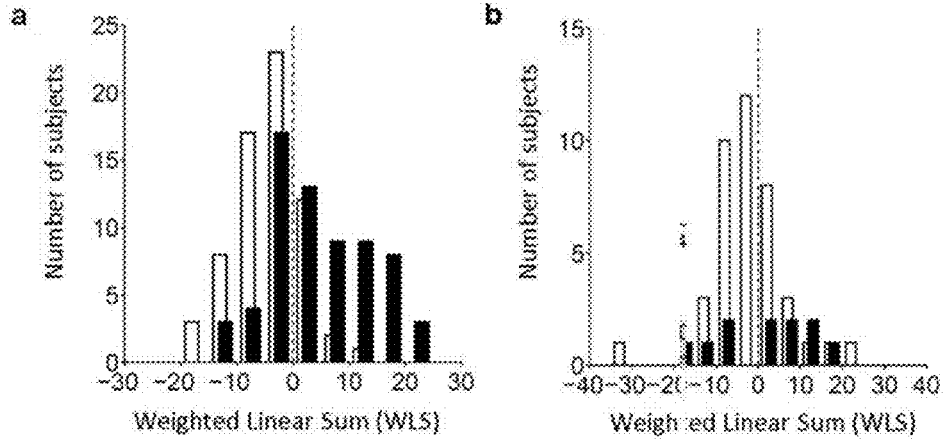

<table>
<thead>
<tr><th></th><th></th><th></th><th></th></tr>
</thead>
<tbody>
<tr><td>All MDD<br>classifier (n=186)</td><td>AUC: 0.53,<br>Accuracy: 0.53,<br>Sensitivity: 0.61,<br>Specificity: 0.44<br>(LOOCV)</td><td>AUC: 0.55,<br>Accuracy: 0.54,<br>Sensitivity: 0.64,<br>Specificity: 0.44<br>(LOOCV)</td><td>AUC: 0.44,<br>Accuracy: 0.46,<br>Sensitivity: 0.50,<br>Specificity: 0.42<br>(LOOCV)</td></tr>
<tr><td>Melancholic MDD<br>Classifier (n=132)</td><td>AUC: 0.74,<br>Accuracy: 0.66,<br>Sensitivity: 0.58,<br>Specificity: 0.74<br>(LOOCV)</td><td>AUC: 0.77,<br>Accuracy: 0.70,<br>Sensitivity: 0.64,<br>Specificity: 0.77<br>(LOOCV)</td><td>AUC: 0.65,<br>Accuracy: 0.54,<br>Sensitivity: 0.42,<br>Specificity: 0.67<br>(EXT)</td></tr>
<tr><td>Non-melancholic<br>MDD<br>classifier (n=48)</td><td>AUC: 0.63,<br>Accuracy: 0.60,<br>Sensitivity: 0.57,<br>Specificity: 0.63<br>(LOOCV)</td><td>AUC: 0.58,<br>Accuracy: 0.57,<br>Sensitivity: 0.55,<br>Specificity: 0.59<br>(EXT)</td><td>AUC: 0.73,<br>Accuracy: 0.69,<br>Sensitivity: 0.62,<br>Specificity: 0.75<br>(LOOCV)</td></tr>
</tbody>
</table>

[Fig. 28]
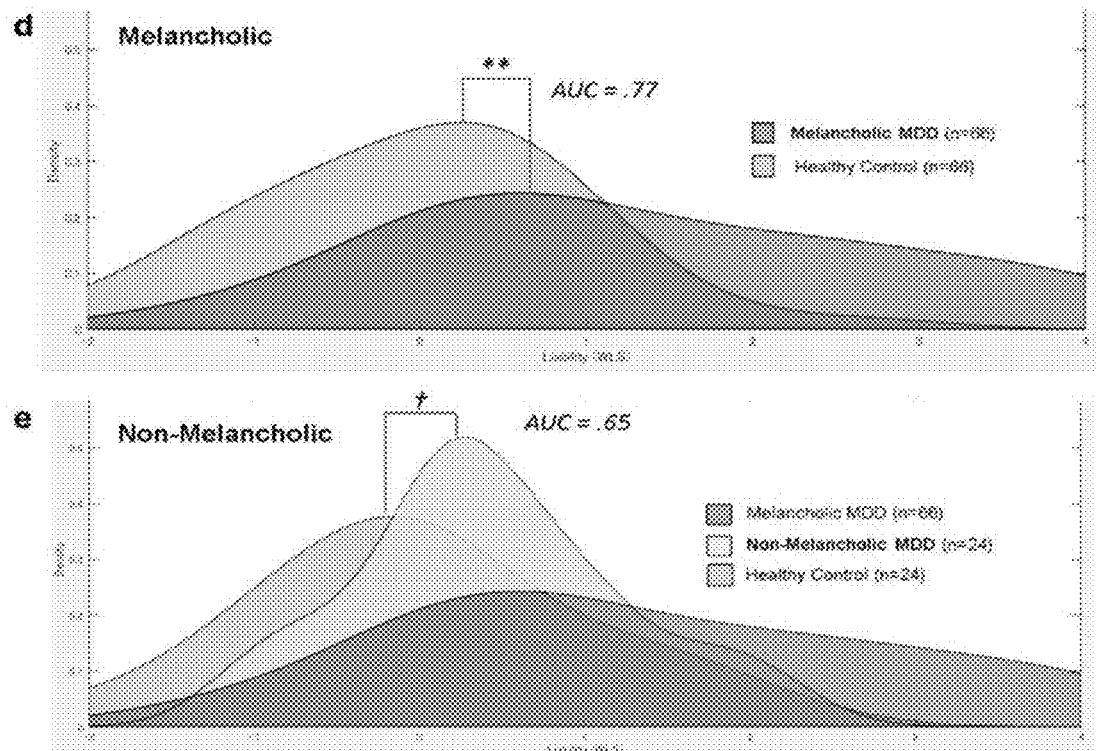

[Fig. 29]
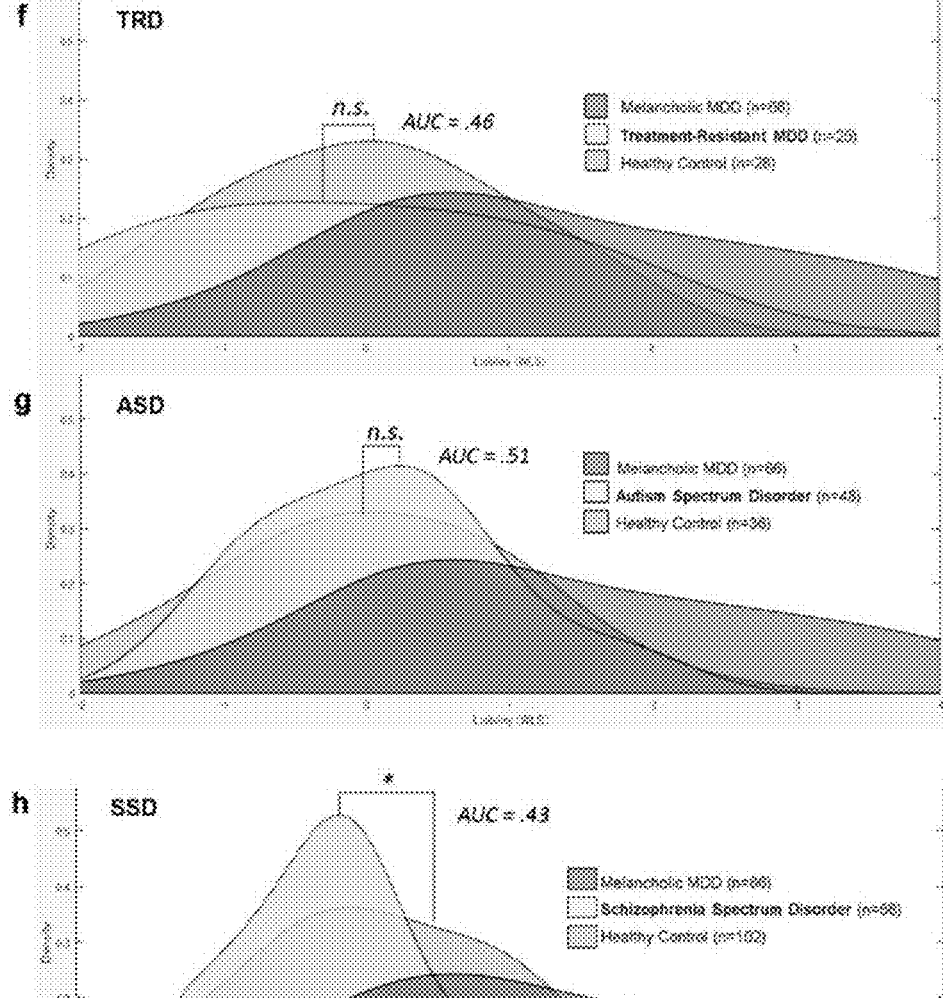

[Fig. 30]
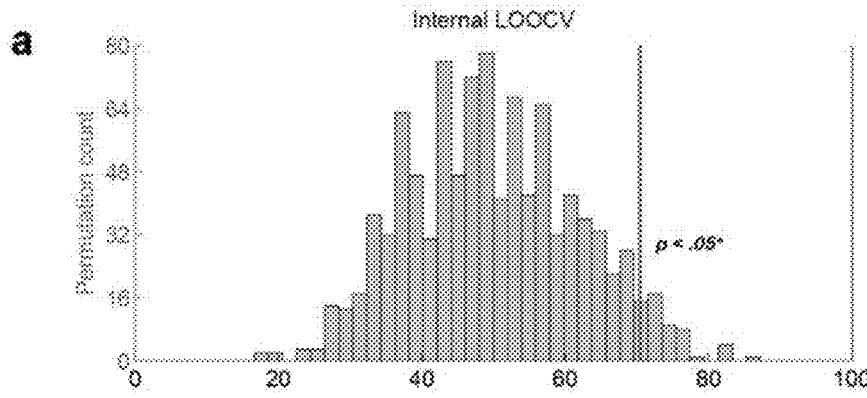
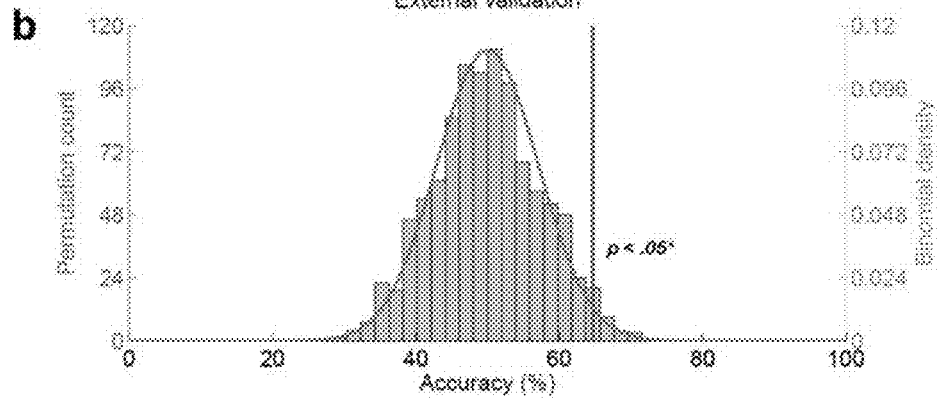

[Fig. 31]
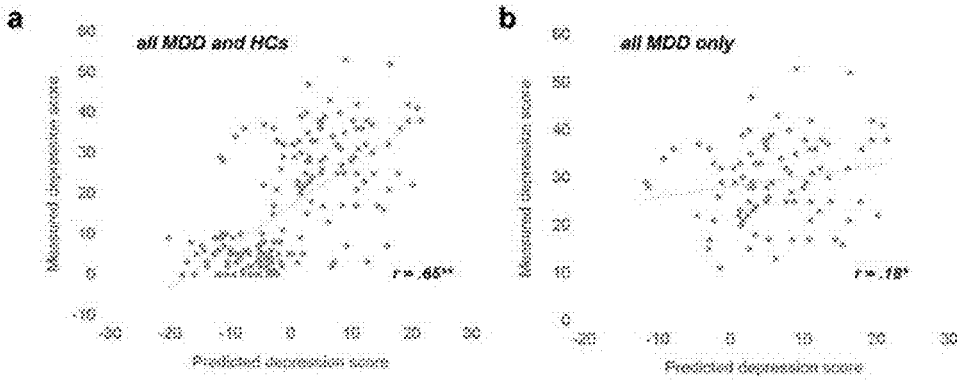
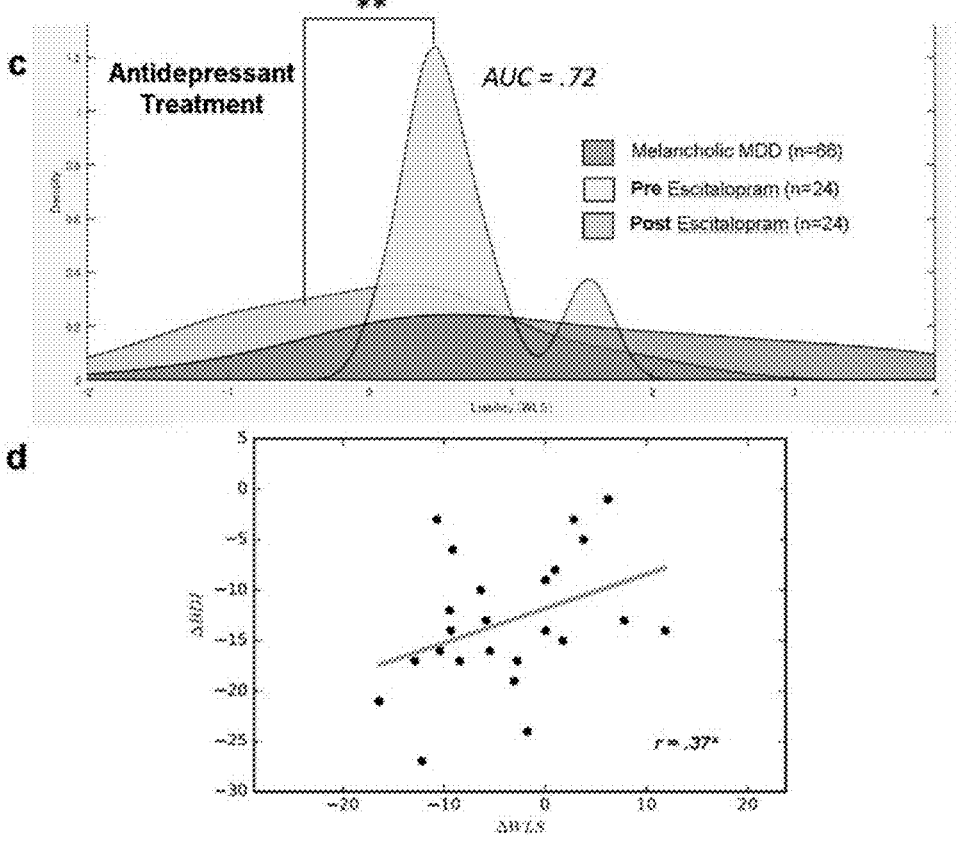

[Fig. 32]
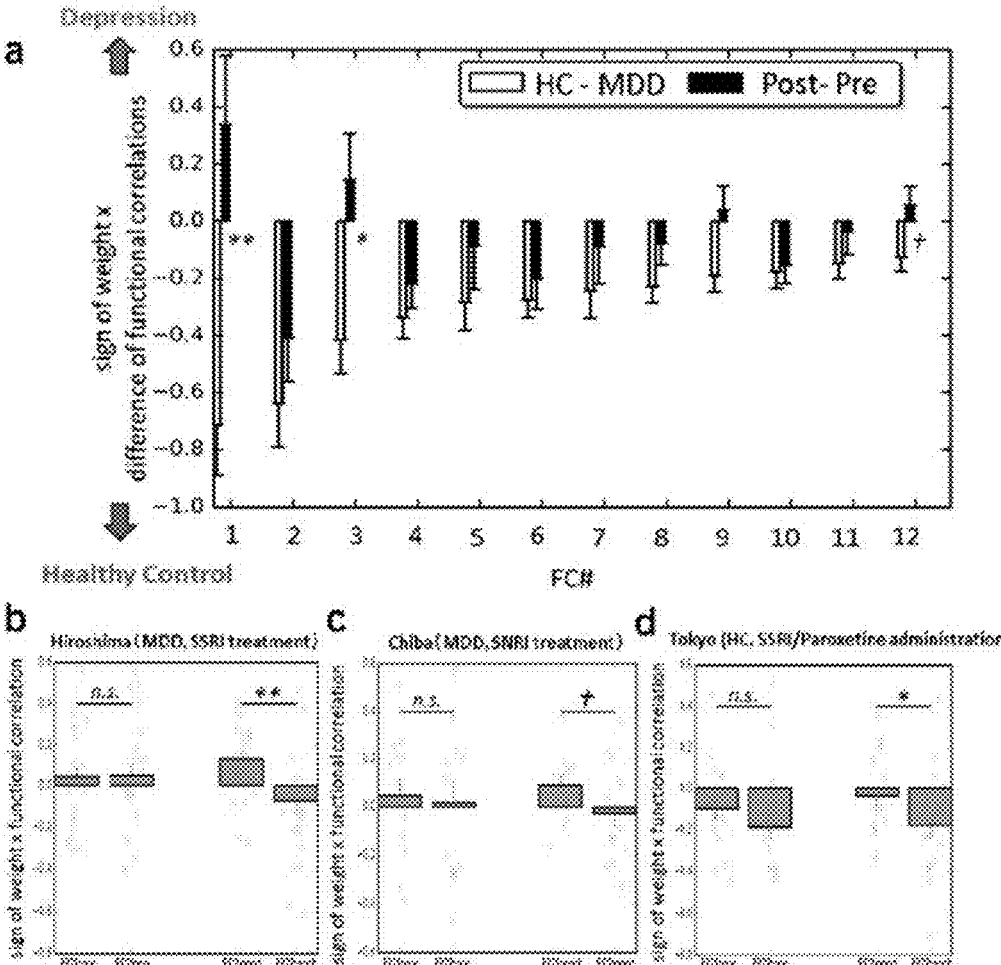

[Fig. 33]
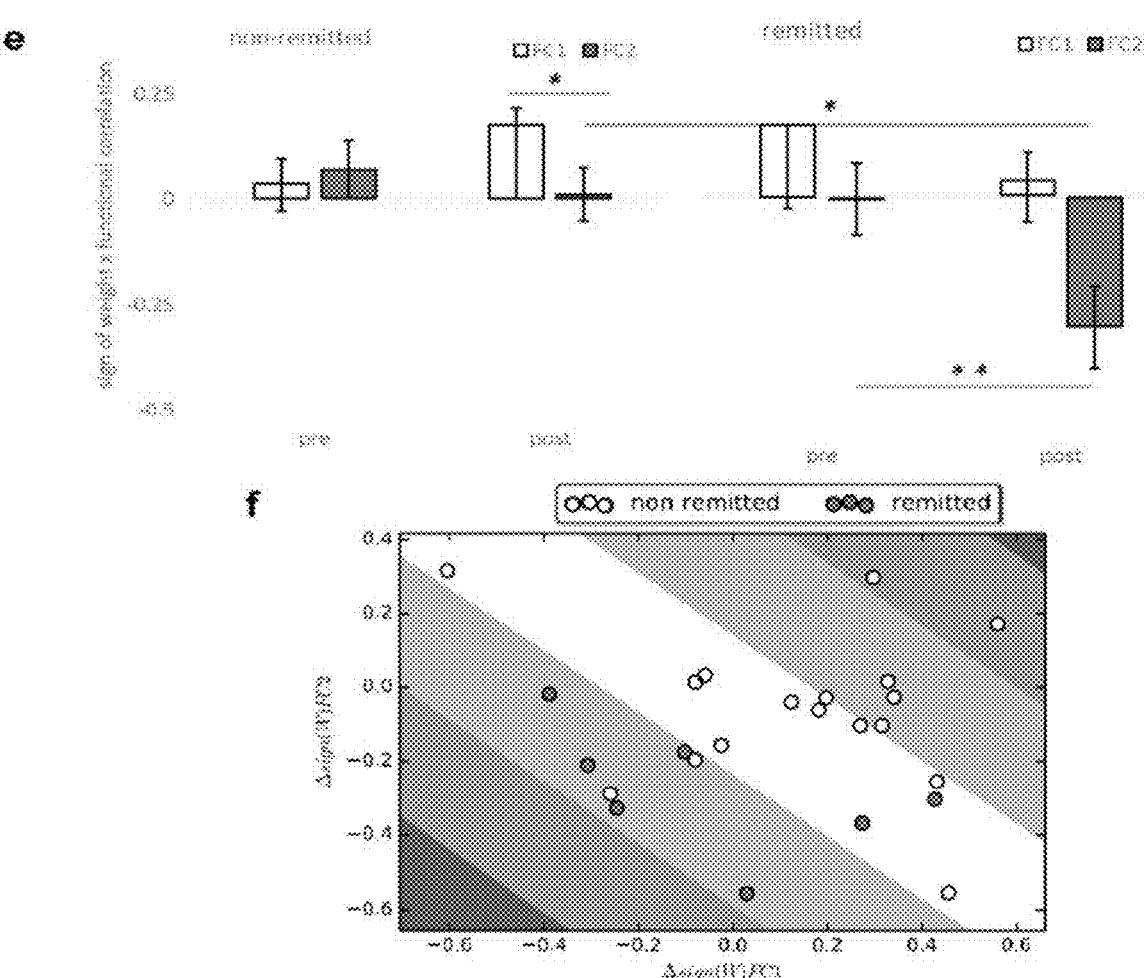

[Fig. 34]
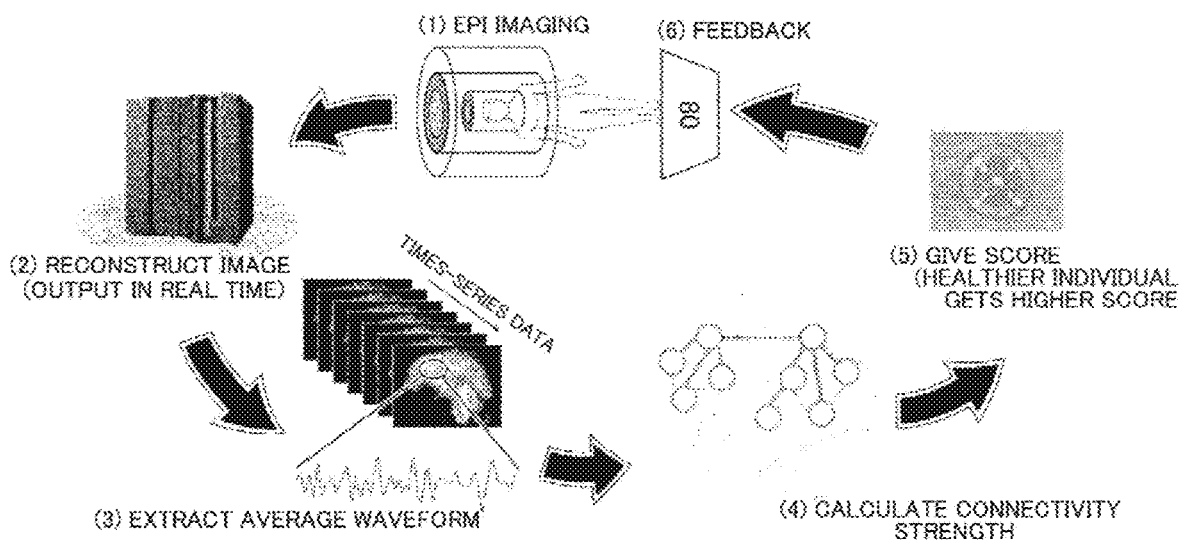

[Fig. 35]
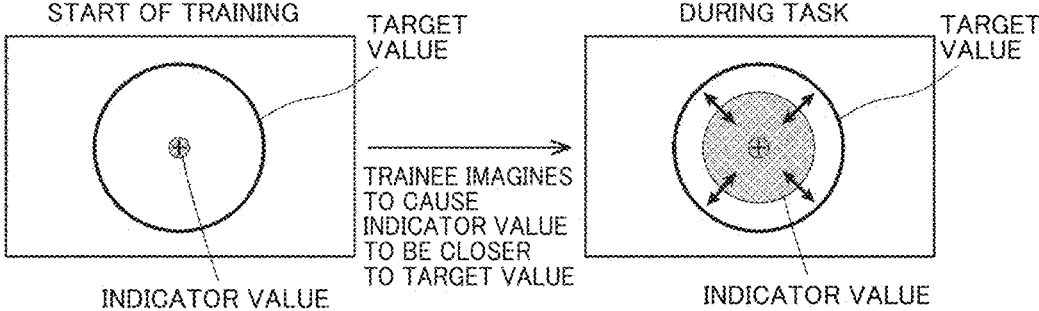

[Fig. 36]
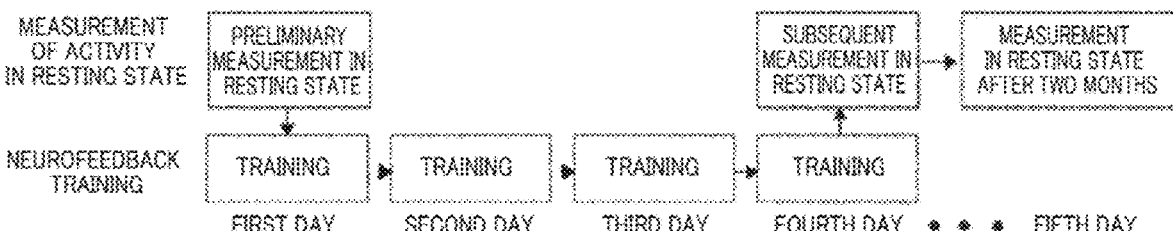

[Fig. 37]
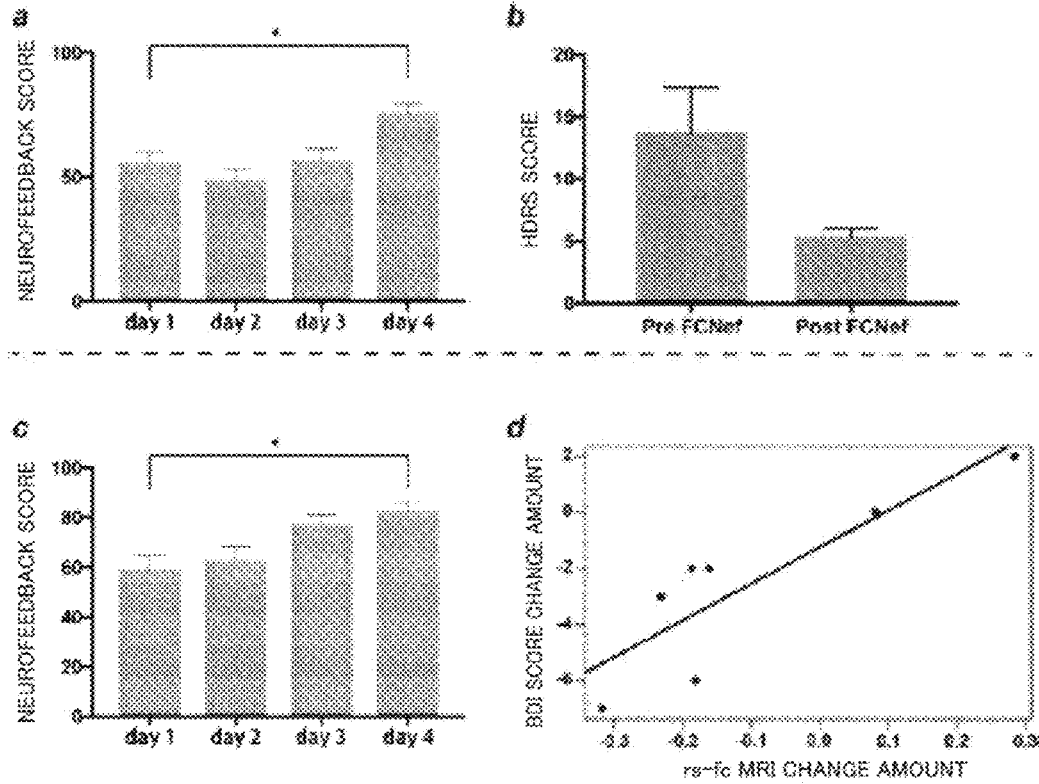

[Fig. 38]
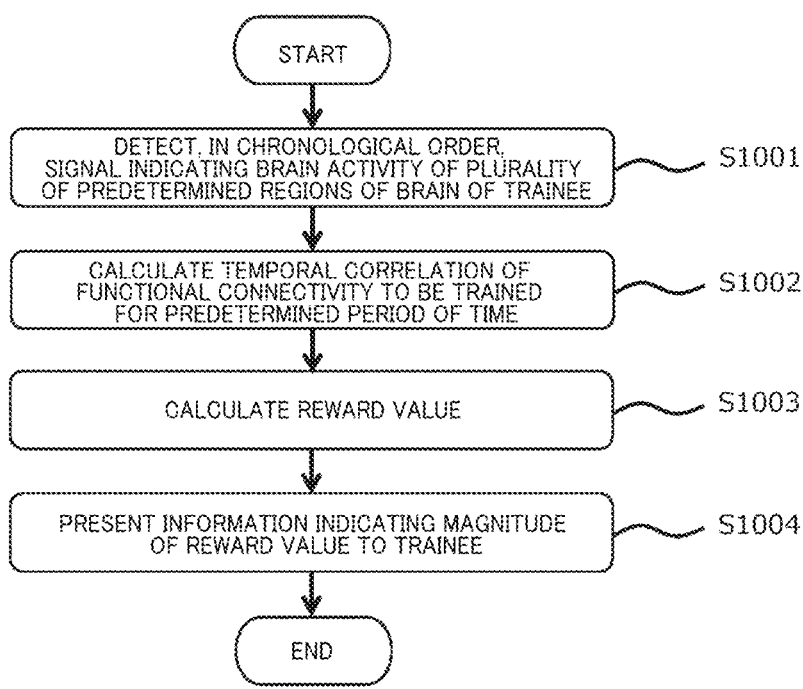

DIFFERENTIATION DEVICE, DIFFERENTIATION METHOD FOR DEPRESSION SYMPTOMS, DETERMINATION METHOD FOR LEVEL OF DEPRESSION SYMPTOMS, STRATIFICATION METHOD FOR DEPRESSION PATIENTS, DETERMINATION METHOD FOR EFFECTS OF TREATMENT OF DEPRESSION SYMPTOMS, AND BRAIN ACTIVITY TRAINING DEVICE

CROSS-REFERENCE TO RELATED APPLICATIONS

This application is a Continuation of copending application Ser. No. 16/753,291, filed on Sep. 14, 2020, which is the National Phase under 35 U.S.C. § 371 of International Application No. PCT/JP2018/036952, filed on Oct. 2, 2018, which claims the benefit under 35 U.S.C. § 119 (a) to Patent Application No. 2017-193897, filed in Japan on Oct. 3, 2017 and Patent Application No. 2018-005110, filed in Japan on Jan. 16, 2018, all of which are hereby expressly incorporated by reference in their entirety into the present application.

TECHNICAL FIELD

The present invention relates to a discriminating device, a discriminating method for a depressive symptom, a discriminating method for a level of the depressive symptom, a classification method for a patient with depression, a discriminating method for a therapeutic effect on the depressive symptom, and a brain activity training device.

BACKGROUND ART (Biomarker)

An indicator that quantifies biological information to quantitatively grasp biological changes inside a living body is called a "biomarker".

The United States Food and Drug Administration (FDA) defines the biomarker as a "characteristic that is measured as an indicator of normal biological processes, pathogenic processes, or responses to an exposure or intervention, including therapeutic interventions." Further, a biomarker that characterizes a state or change of a disease or a degree of recovery is used as a surrogate marker (alternative marker) for verifying effectiveness of a new drug in a clinical test. A blood sugar level, a cholesterol level, or the like is a representative biomarker as an indicator of a lifestyle disease. Not only substances contained in urine or blood, which comes from a living body, but also an electrocardiogram, a blood pressure, PET images, a bone density, a lung function, and the like are included in the biomarker. Further, due to development of genomic analysis or proteome analysis, various kinds of biomarkers relating to, for example, DNA, RNA, and a living body protein are discovered.

The biomarker is expected to be used not only for measurement of a therapeutic effect after a patient has caught a disease, but also for preventing a disease as an indicator used in a daily life for preventing the disease or for application to personalized medicine in which an effective treatment that avoids a side effect is selected.

However, in the case of a neurological/mental disorder, a molecular marker or the like, which can be used as an indicator that is objective in terms of biochemistry or molecular genetics, is still being examined in research and development.

Meanwhile, there is also a report of, for example, a disease discriminating system configured to perform classification for schizophrenia, depression, or other mental disorders in accordance with a feature obtained from a hemoglobin signal measured through living body light measurement by using the technology of near-infrared spectroscopy (NIRS) (Patent Literature 1).

The biomarker is used not only for usual diagnosis but also for development of a medicine.

In the case of usual drug development, a pharmacodynamic marker is used at an exploratory research stage, and a toxicity marker, which examines toxicity of a candidate compound, is also used at a non-clinical stage.

At a clinical test stage, a surrogate marker is used as an evaluation item, or various kinds of markers such as a diagnostic marker, a prognostic marker, a predictive marker, a monitoring marker, and a safety marker are used.

The term "surrogate marker" refers to a marker whose scientific relationship with a true end point is already validated.

The term "diagnostic marker" refers to two types of markers, namely, a diagnostic marker that identifies presence of a disease or the type of a disease, and a diagnostic marker that determines the degree of severity or progression of a disease. The term "predictive marker" refers to a biomarker that identifies a group to which a specific drug is effective. The term "prognostic marker" refers to a biomarker that predicts progression or recovery of a disease irrespective of a specific treatment. The "monitoring marker" is also called an "efficacy marker", which is a marker that verifies the efficacy or therapeutic effect of a drug. When this marker is monitored for a long period of time, the marker may also be used as a hint for detecting a cause of drug resistance.

For example, when a target molecule is clear, for example, the target molecule may be used as a stratification marker in a clinical test to identify and select a group of patients to which a specific drug is effective. In such a case, when a medicine that uses the stratification marker is approved, a diagnostic agent for measuring the stratification marker may be called a "companion diagnostic agent". In other cases, diagnosis to be performed to select treatment for a patient by such a stratification marker may be called "companion diagnosis".

The second half of a clinical test costs very high, and thus development of a biomarker appropriate for the second half of a clinical test is considered to be required in order to improve the efficiency of the clinical test. However, development of such a biomarker is not easy in general.

Further, for example, when a biological indicator (biomarker) is considered, in pathophysiology of a disease, a so-called "trait marker" reflects an ethological or biological process relating to a cause of the disease, and a so-called "state marker" reflects a clinical condition of a patient. The trait marker is also called a "hereditary indicator", and the state marker is also called a "state-dependent indicator".

(Real-Time Neurofeedback)

For example, hitherto, there have been known a pharmacological treatment and a behavioral treatment as treatment for obsessive-compulsive disorder (OCD), which is one type of neurosis. For example, a selective serotonin reuptake inhibitor is used for the pharmacological treatment, and an exposure response prevention therapy combining an exposure therapy and a response prevention therapy is known as the behavioral treatment, for example.

Meanwhile, real-time neurofeedback is considered as a possible treatment for a neurological/mental disorder (Patent Literature 6).

Functional brain imaging, which includes, for example, functional magnetic resonance imaging (fMRI) being a method of visualizing hemodynamic reaction related to an activity of a human brain by using magnetic resonance imaging (MRI), has been used for detecting a difference between a brain activity due to sensory stimulus or execution of a cognitive task and a brain activity due to a resting state or execution of a control task, to thereby identify a brain activated region corresponding to a component of a brain function of interest, that is, find out localization of the brain function.

In recent years, there has been a report of the real-time neurofeedback technology using functional brain imaging, for example, functional magnetic resonance imaging (fMRI) (Non-patent Literature 1). The real-time neurofeedback technology has started to be given attention as treatment for a neurological disorder and a mental disorder.

Neurofeedback is one type of biofeedback, and a subject receives feedback of his or her own brain activity to learn a method of operating the brain activity.

For example, there is a report that when the activity of an anterior cingulate cortex is measured by fMRI and a patient receives feedback of the activity as the size of a fire in real time to try to reduce the fire, the chronic pain of a central origin is improved in real time and for a long period of time (refer to Non-patent Literature 2).

(Resting-State fMRI)

Further, a recent study has revealed that the brain is active even under a resting state. Specifically, there is a nerve cell group in the brain, which is calm during a human activity and is actively excited during rest. In terms of anatomy, a medial surface of combined left and right cerebral hemispheres mainly corresponds to such a part, and includes, for example, a medial aspect of a frontal lobe, a posterior cingulate cortex, a precuneus, a posterior portion of parietal association area, and a middle temporal gyrus. A region indicating a baseline of the brain activity in this resting state is named a "default mode network (DMN)", and acts as one network in synchronization (refer to Non-patent Literature 3).

For example, a brain activity in the default mode network is given an example of difference between brain activities of healthy individuals and patients with a mental disorder. The default mode network indicates a portion at which the brain activity is more active under a resting state than a brain activity during execution of a goal-based task. There is a report that a patient with a disease such as schizophrenia or Alzheimer's disease exhibits an abnormality in the default mode network compared to a healthy individual. For example, there is a report that a patient with schizophrenia has a decreased correlation in activity between a posterior cingulate cortex, which belongs to the default mode network, and a parietal lateral cortex, a medial prefrontal cortex, or a cerebellar cortex, under a resting state.

However, for example, how such a default mode network and a cognitive function relate to each other and how a correlation between functional connectivities of brain regions and the above-mentioned neurofeedback relate to each other are not necessarily revealed.

Meanwhile, a change in correlation relationship between activities due to, for example, tasks in a plurality of brain regions is examined to evaluate functional connectivities of those plurality of brain regions. In particular, evaluation of a functional connectivity by fMRI under a resting state is also called "resting-state functional connectivity MRI (rs-fc MRI)", and clinical researches for various kinds of neurological/mental disorders are also gradually conducted more widely. However, the related-art rs-fc MRI method examines the activity of a global neural network, for example, the above-mentioned default mode network, and currently does not sufficiently consider a more detailed functional connectivity.

(Magnetic Resonance Imaging)

Now, a brief description is given below of such magnetic resonance imaging.

Specifically, hitherto, magnetic resonance imaging that uses a magnetic resonance phenomenon for atoms inside a living body, in particular, atomic nuclei of hydrogen atoms has been used for, for example, human clinical diagnostic imaging as a method of imaging a cross section of the brain or whole body of a living body.

When the magnetic resonance imaging is applied to a human body, the magnetic resonance imaging has, for example, the following characteristic in comparison with "X-ray CT" being similar human tomographic imaging.

(1) An image with a density corresponding to the distribution of hydrogen atoms and the signal relaxation time (reflecting strength of bonding between atoms) is obtained. Thus, light and shade that depend on the difference in nature of tissue are exhibited, which facilitates observation of the difference in tissue.

(2) The magnetic field is not absorbed by bones. Thus, a portion (e.g., inside skull or spinal cord) surrounded by bones is easily observed.

(3) The magnetic resonance imaging does not harm a human body unlike an X ray, and thus can be utilized in a wide range of applications.

Such magnetic resonance imaging uses a magnetic property of hydrogen atomic nuclei (protons), which are contained in each call of a human body most and have the largest magnetic property. A motion of spin angular momentum within the magnetic field, which is responsible for the magnetic property of hydrogen atomic nuclei, is classically compared to precession of a top.

Now, a principle of nuclear magnetic resonance is briefly summarized by the intuitive classical model in order to describe the background of the present invention.

The direction (direction of rotation axis of top) of spin angular momentum of the above-mentioned hydrogen atomic nuclei is random in an environment without a magnetic field, but is the same as the direction of a magnetic field line when a static magnetic field is applied thereto.

Under this state, when an oscillating magnetic field is applied additionally and the frequency of this oscillating magnetic field is a resonance frequency $f0=\gamma B0/2\pi$ ($\gamma$: substance-specific coefficient) determined by the strength of the static magnetic field, resonance causes energy to move toward the atomic nuclei, and the direction of a magnetization vector changes (magnitude of precession becomes larger). Under this state, when the oscillating magnetic field is canceled, precession returns an inclination angle to its original angle while at the same time returning to the direction under the static magnetic field. This process is detected by an antenna coil from the outside, to thereby be able to obtain an NMR signal.

Such a resonance frequency $f0$ of a hydrogen atom is $42.6 \times B0$ (MHz) when the intensity of the static magnetic field is B0 (T).

Further, magnetic resonance imaging can also visualize a portion of the brain that has become active in response to, for example, an external stimulus, based on the fact that a detected signal changes depending on a change in amount of blood flow. Such magnetic resonance imaging is particularly called "functional magnetic resonance imaging".

In terms of apparatus of fMRI, a general MRI apparatus that has additionally mounted hardware and software required for fMRI measurement is used.

The fMRI uses the fact that a change in amount of blood flow causes a change in intensity of an NMR signal because oxygenated hemoglobin and deoxygenated hemoglobin in blood have different magnetic properties. The oxygenated hemoglobin has a property of a diamagnetic substance and does not influence the relaxation time of a surrounding hydrogen atom of water, whereas the deoxygenated hemoglobin is a paramagnetic substance and changes the surrounding magnetic field. Thus, when the brain is stimulated, local blood flow increases, and the oxygenated hemoglobin increases, the corresponding change can be detected as an MRI signal. As stimulus to a subject, for example, visual stimulus, auditory stimulus, or execution of a predetermined task is used (e.g., Patent Literature 2).

Meanwhile, in research of a brain function, the activity of the brain is measured by measuring an increase in nuclear magnetic resonance signal (MRI signal) of a hydrogen atom that corresponds to a phenomenon (BOLD effect) in which the concentration of deoxygenated hemoglobin of a red blood cell in a minute vein or a capillary vessel decreases.

In particular, in research of the motion function of a human, a subject performs some motion, and at the same time, the above-mentioned MRI apparatus measures the activity of the brain.

Meanwhile, in the case of a human, non-invasive measurement of the brain activity is required, and in this case, a decoding technology that can extract more detailed information from fMRI data is being developed (e.g., Non-patent Literature 4). In particular, fMRI analyzes the brain activity in units of volumetric pixels (voxels) in the brain, to thereby enable estimation of the stimulus input or recognition state based on a spatial pattern of the brain activity.

Further, as a technology that has developed such a decoding technology, in Patent Literature 3, there is disclosed a brain activity analysis method for achieving a biomarker by functional brain imaging for a neurological/mental disorder. This method derives a correlation matrix of the degrees of activity of predetermined brain regions for each subject based on data of resting-state functional connectivity MRI, which is measured for a group of healthy individuals and a group of patients. A feature is extracted by regularized canonical correlation analysis for the correlation matrix and the attribute of a subject with a disease/healthy individual label of the subject. A classifier that functions as a biomarker is generated by discriminant analysis using sparse logistic regression (SLR) based on the result of regularized canonical correlation analysis (sparse canonical correlation analysis). It has been shown that, with such a technology of machine learning, the result of diagnosis of autism can be predicted based on a connectivity (functional connectivity) between brain areas derived from the resting-state fMRI data (Patent Literature 4 and Patent Literature 5). Further, it has been shown that validation of the prediction performance is not only limited to a brain activity measured in one facility, but also can be generalized to some extent to a brain activity measured in another facility.

Further, in recent years, it has been pointed out that fMRI can be used for a large multisite sample group (n=1,188)

obtained from a large number of research facilities to classify a patient with depression into four neurophysiological subtypes (biotypes), and such a biotype is clearly represented by each different pattern indicating dysfunctional connectivity in limbic and frontostriatal networks (refer to Non-patent Literature 5). In Non-patent Literature 5, those biotypes cannot be differentiated solely on the basis of clinical features, but are associated with different clinical-symptom profiles. Further, responsiveness to transcranial magnetic stimulation therapy is predicted (n=154).

In Non-patent Literature 5, the above-mentioned subtypes are classified by functional connectivity inside the brain based on BOLD signals obtained from 258 regions inside the brain.

CITATION LIST

Patent Literature

PTL 1: JP 2006/132313
PTL 2: JP 2011-000184 A
PTL 3: JP 2015-62817 A
PTL 4: JP 6195329 B1
PTL 5: WO 2017/090590 A1
PTL 6: JP 5641531 B1

Non-Patent Literature

NPL 1: Nikolaus Weiskopf, "Real-time fMRI and its application to neurofeedback", NeuroImage 62 (2012) 682-692
NPL 2: deCharms R C, Maeda F, Glover G H et al, "Control over brain activation and pain learned by using real-time functional MRI", Proc Natl Acad Sci USA 102 (51), 18626-18631, 2005
NPL 3: Raichle M E, Macleod A M, Snyder A Z. et al. "A default mode of brain function", Proc Natl Acad Sci USA 98 (2), 676-682, 2001
NPL 4: Kamitani Y, Tong F. Decoding the visual and subjective contents of the human brain. Nat Neurosci. 2005; 8:679-85.
NPL 5: Drysdale A T, Grosenick L, Downar J, Dunlop K, Mansouri F, Meng Y, Fetcho R N, Zebley B, Oathes D J, Etkin A, Schatzberg A F, Sudheimer K, Keller J, Mayberg H S, Gunning F M, Alexopoulos G S, Fox M D, Pascual-Leone A, Voss H U, Casey B J, Dubin M J, Liston C. Resting-state connectivity biomarkers define neurophysiological subtypes of depression. Nat Med. 2017 23 (1): 28-38.

SUMMARY OF INVENTION

Technical Problem

As described above, when analysis of a brain activity by functional brain imaging, for example, functional magnetic resonance imaging, is considered to be applied to treatment of a neurological/mental disorder, for example, as the above-mentioned biomarker, analysis of a brain activity by functional brain imaging is also expected to be applied as a non-invasive functional marker to, for example, development of a diagnosis method, and search and identification of a target molecule for drug development for achieving fundamental treatment.

For example, hitherto, development of a practical biomarker using a gene has not been complete for depression, and thus objective determination of an effect of a drug has not been easy and development of a remedy has also been difficult.

In order to generate a classifier by machine learning based on measurement data of a brain activity and put the classifier into practical use as a biomarker, it is required to improve the accuracy of prediction of the biomarker generated by machine learning for a brain activity measured in one facility. Further, the biomarker generated in this manner is required to be able to be generalized also for brain activities measured in other facilities.

That is, there are two main problems for constructing a classifier by machine learning based on measurement data on a brain activity.

The first problem is a problem of a small sample size.

An amount N of data being the number of participants is much smaller than a dimension M of brain activity measurement data obtained through measurement, and thus parameters of a classifier are easily over-fit to training data (called "overfitting" or "overtraining").

Due to this overfitting, a constructed classifier exhibits extremely poor performance for newly sampled test data. This is because such test data has not been used for training the classifier.

Thus, it is required to appropriately introduce regularization in order to identify and use only the essential feature for desired generalization of the classifier.

For example, in Non-patent Literature 5 described above, such regularization is not necessarily considered sufficiently.

The second problem is that a constructed classifier is clinically useful and scientifically reliable only when the classifier maintains excellent performance also for MRI data scanned at imaging sites different from a site at which training data has been collected.

This is so-called generalization capability over imaging sites.

However, in clinical application, it is often observed that a classifier trained by using data acquired at a specific site cannot be generalized to data scanned at different sites.

The present invention has been made to solve the above-mentioned problems, and an object thereof is to achieve objective discrimination of a disease label of a depressive symptom with respect to an active state of a brain. Further, another object of the present invention is to achieve discrimination of information representing a degree of a therapeutic effect on a depressive symptom. Another object of the present invention is to provide a classifier configured to output an indicator value serving as a biomarker for discriminating a state of a depressive symptom in an objective manner. Another object of the present invention is to achieve discrimination of a level of a depressive symptom. Another object of the present invention is to achieve classification of a patient with depression.

Solution to Problem

One embodiment of the present invention relates to a discriminating device for assisting in determination of whether a subject has a depressive symptom. The discriminating device according to this embodiment includes a storage device for storing information for identifying a classifier generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating device according to this embodiment further includes a processor configured to execute discriminating processing of generating a classification result for the depressive symptom of the subject by using the classifier.

One embodiment of the present invention relates to a discriminating device for a level of a depressive symptom. The discriminating device according to this embodiment includes a storage device for storing information for identifying a classifier generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating device according to this embodiment further includes a processor configured to generate, by the classifier, an indicator value for evaluating a depressive symptom for elements of a correlation matrix of functional connectivities measured for a subject in a resting state. The processor is configured to compare the indicator value with a reference range of the indicator value, which is set in advance in accordance with a level of the depressive symptom for each of the plurality of functional connectivities. The processor is configured to determine that the subject has a level of the depressive symptom corresponding to the reference range including the indicator value.

One embodiment of the present invention relates to a discriminating device for determining a therapeutic effect on a subject. The discriminating device according to this embodiment includes a storage device for storing information for identifying a classifier generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating device according to this embodiment further includes a processor configured to generate a first value for evaluating the depressive symptom for elements of a correlation matrix of functional connectivities measured at a first time point for the subject in a resting state by using the classifier. The processor is configured to generate a second value for evaluating the depressive symptom for elements of a correlation matrix of the same functional connectivities inside the brain measured at a second time point for the same subject in the resting state by using the classifier, the second time point being a time point after start of treatment and later than the first time point. The processor is configured to compare the first value with the second value. The discriminating device according to this embodiment is configured to determine that the treatment is effective for improvement of the depressive symptom of the subject when the second value is improved more than the first value, and/or determine that the treatment is not effective for improvement of the depressive symptom of the subject when the second value is not improved more than the first value.

One embodiment of the present invention relates to a discriminating device for classifying a patient with depression when a depressive symptom is classified into a plurality of subclasses set in advance. The discriminating device according to this embodiment includes a processor configured to generate an indicator value for evaluating a depressive symptom for elements of a correlation matrix of functional connectivities measured for a subject in a resting state. The processor is configured to compare the indicator value with a reference range of the indicator value, which is set in advance in accordance with each of the plurality of subclasses for each of the plurality of functional connectivities. The processor is configured to determine that the subject has one of the plurality of subclasses corresponding to the reference range including the indicator value.

One embodiment of the present invention relates to a computer program for causing the discriminating device to execute the above-mentioned processing.

One embodiment of the present invention relates to a discriminating method for assisting in determination of a subject with a depressive symptom. The discriminating method according to this embodiment includes a step of generating an indicator value for evaluating a depressive symptom for elements of a correlation matrix of functional connectivities measured for a subject in a resting state. The functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating method according to this embodiment further includes a step of determining that the subject has the depressive symptom when the indicator value exceeds a reference value.

One embodiment of the present invention relates to a discriminating method for assisting in determination of a level of a depressive symptom for a subject. The discriminating method according to this embodiment includes a step of generating an indicator value for evaluating a depressive symptom for elements of a correlation matrix of functional connectivities measured for a subject in a resting state. The functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating method according to this embodiment further includes the steps of: comparing the indicator value with a reference range of the indicator value, which is set in advance in accordance with the level of the depressive symptom for each of the functional connectivities; and determining that the subject has a level of the depressive symptom corresponding to the reference range including the indicator value.

One embodiment of the present invention relates to a discriminating method for assisting in determination of a therapeutic effect on a subject. The discriminating method according to this embodiment includes a step of generating a first value for evaluating a depressive symptom for elements of a correlation matrix of functional connectivities measured at a first time point for a subject in a resting state. The functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating method according to this embodiment further includes a step of generating a second value for evaluating the depressive symptom for elements of a correlation matrix of the same functional connectivities inside a brain measured at a second time point for the same subject in the resting state, the second time point being a time point after start of treatment and later than the first time point. The discriminating method according to this embodiment further includes the steps of: comparing the first value with the second value; and determining that the treatment is effective for improving the depressive symptom of the subject when the second value is improved more than the first value.

One embodiment of the present invention relates to a discriminating method for assisting in determination of a therapeutic effect on a subject. The discriminating method according to this embodiment includes a step of generating a first value for evaluating a depressive symptom for elements of a correlation matrix of functional connectivities measured at a first time point for a subject in a resting state. The functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating method according to this embodiment further includes a step of generating a second value for evaluating the depressive symptom for elements of a correlation matrix of the same functional connectivities inside a brain measured at a second time point for the same subject in the resting state, the second time point being a time point after start of treatment and later than the first time point. The discriminating method according to this embodiment further includes the steps of: comparing the first value with the second value; and determining that the treatment is not effective for improving the depressive symptom of the subject when the second value is not improved more than the first value.

One embodiment of the present invention relates to a discriminating method for assisting in classification of a patient with depression. The discriminating method according to this embodiment includes a step of, when a depressive symptom is classified into a plurality of subclasses set in advance, generating an indicator value for evaluating the depressive symptom for elements of a correlation matrix of functional connectivities measured for a subject in a resting state. The functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating method according to this embodiment further includes the steps of: comparing the indicator value with a reference range of the indicator value, which is set in advance in accordance with each of the plurality of subclasses for each of the functional connectivities; and determining that the subject has one of the plurality of subclasses corresponding to the reference range including the indicator value.

One embodiment of the present invention relates to a discriminating device for assisting in classification of a patient with depression. The discriminating device according to this embodiment includes: a processor configured to execute classification processing; and a storage device for storing information for identifying a classifier generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. In the discriminating device according to this embodiment, when the depressive symptom is classified into a plurality of subclasses set in advance, the classifier is generated so as to discriminate a label of a subclass of the depression for elements of a correlation matrix to be discriminated, which corresponds to a plurality of functional connectivities, based on a weighted sum of the plurality of functional connectivities selected by feature selection as being relevant to the label of the subclass of the depression through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The processor is configured to execute processing for discriminating the subclass based on the weighted sum and the elements of the correlation matrix to be discriminated.

One embodiment of the present invention relates to a discriminating device for assisting in determination of a therapeutic effect on a patient with depression. The discriminating device according to this embodiment includes a processor configured to execute classifier generation processing of measuring, for a plurality of subjects, a correlation at a first time point of a plurality of functional connectivities selected from among functional connectivity identification numbers 1 to 12 shown in Table 1, and a correlation at a second time point of the plurality of functional connectivities, the second time point being set to be after start of treatment and later than the first time point, to thereby generate in advance a classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point. The processor is configured to measure a first correlation of the plurality of functional connectivities inside the brain of the subject in the resting state at the first time point, and measure a second correlation of the plurality of functional connectivities inside the brain of the same subject in the resting state at the second time point. The processor is configured to discriminate a therapeutic effect on the subject by using the classifier based on a difference between the first correlation and second correlation of the plurality of functional connectivities of the subject.

One embodiment of the present invention relates to a discriminating method for assisting in determination of a therapeutic effect on a patient with depression. The discriminating method according to this embodiment includes a step of measuring, for a plurality of subjects, a correlation at a first time point of a plurality of functional connectivities selected from among functional connectivity identification numbers 1 to 12 shown in Table 1, and a correlation at a second time point of the plurality of functional connectivities, the second time point being set to be after start of treatment and later than the first time point, to thereby generate in advance a classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point. The discriminating method according to this embodiment further includes the steps of: measuring a first correlation of the plurality of functional connectivities inside the brain of the subject in the resting state at the first time point; and measuring a second correlation of the plurality of functional connectivities inside the brain of the same subject in the resting state at the second time point. The discriminating method according to this embodiment further includes a step of discriminating a therapeutic effect on the subject by using the classifier based on a difference between the first correlation and the second correlation of the plurality of functional connectivities of the subject.

One embodiment of the present invention relates to a method of using a classifier to assist in determination of whether a subject has a depressive symptom or determination of a level of the depressive symptom, the classifier being generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The method includes a step of generating the classifier configured to discriminate a disease label of the depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The method further includes a step of inputting, into the classifier, an indicator value generated based on elements of a correlation matrix of the plurality of functional connectivities of the subject.

One embodiment of the present invention relates to a method of using a classifier to assist in determination of an effect of treatment of a depressive symptom, the classifier being generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The method includes a step of generating the classifier configured to discriminate a disease label of the depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The method further includes a step of inputting, into the classifier, an indicator value generated based on elements of a correlation matrix of the plurality of functional connectivities of the subject.

One embodiment of the present invention relates to a method of using, when a depressive symptom is classified into a plurality of subclasses set in advance, a classifier to assist in classification of subjects into the plurality of subclasses, the classifier being generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The classifier is generated so as to discriminate a disease label of the depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The method includes a step of inputting, into the classifier, an indicator value generated based on elements of a correlation matrix of the plurality of functional connectivities of the subject.

One embodiment of the present invention relates to a discriminating device for assisting in determination of a therapeutic effect on a subject. The discriminating device includes a classifier generating device including a first processor configured to generate a first classifier based on a signal obtained by measuring, in advance and time-sequentially, a signal indicating a brain activity of a plurality of predetermined regions of each brain of a plurality of participants in a resting state, the plurality of participants including healthy individuals and patients with depression. The first classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The first processor is configured to measure, for a plurality of subjects, a correlation at a first time point of a plurality of functional connectivities selected from among functional connectivity identification numbers 1 to 12 shown in Table 5, and a correlation at a second time point of the plurality of functional connectivities, the second time point being set to be after start of treatment and later than the first time point, to thereby generate a second classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point. The discriminating device further includes a classification device including a second processor and a storage device. The storage device is configured to store information on the first classifier and the second classifier, and information for classifying the depressive symptom into a plurality of subclasses set in advance. The second processor is configured to execute processing of classifying subjects into the plurality of subclasses by using the first classifier. The second processor is configured to execute processing of measuring, for a subject classified into a specific subclass by the classification processing, a first correlation of the plurality of functional connectivities in the resting state at the first time point. The second processor is configured to execute processing for measuring, for the same subject, a second correlation of the plurality of functional connectivities in the resting state at the second time point. The second processor is configured to discriminate a therapeutic effect on the subject by using the second classifier, based on a difference between the first correlation and the second correlation of the plurality of functional connectivities of the subject.

One embodiment of the present invention relates to a discriminating method for assisting in determination of a therapeutic effect on a subject. The discriminating method according to this embodiment includes a step of classifying, when a depressive symptom is classified into a plurality of subclasses set in advance, subjects into the plurality of subclasses by using a first classifier generated by first classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. In the discriminating method according to this embodiment, the first classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The discriminating method according to this embodiment includes the steps of: measuring, for a subject classified into a specific subclass in the classifying step, a first correlation of the plurality of functional connectivities in the resting state before administration of a drug; and measuring, for the same subject, a second correlation of the plurality of functional connectivities in the resting state after elapse of a predetermined period of time since start of the administration. The discriminating method according to this embodiment further includes a step of discriminating efficacy for the subject classified into the specific subclass by using a second classifier, the second classifier being configured to measure, for a plurality of subjects, a correlation at a first time point of a plurality of functional connectivities selected from among functional connectivity identification numbers 1 to 12 shown in Table 1, and a correlation at a second time point of the plurality of functional connectivities, the second time point being set to be after the administration and later than the first time point. The discriminating method further includes a step of discriminating efficacy for the subject based on a difference between the first correlation and the second correlation of the plurality of functional connectivities of the subject generated in advance by second classifier generation processing of distinguishing between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point.

One embodiment of the present invention relates to a first classifier generating device including a processor and a storage device. The processor is configured to generate information for identifying a classifier based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area. The storage device is configured to store information for identifying the first classifier generated by the processor.

One embodiment of the present invention relates to a method of generating a first classifier. In this embodiment, the first classifier is generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The first classifier is generated so as to discriminate a disease label of a depressive symptom based on a weighted sum of a plurality of functional connectivities selected by feature selection as being relevant to the disease label of the depressive symptom through machine learning from among functional connectivities of the plurality of predetermined regions. The selected plurality of functional connectivities include at least one selected from: a first functional connectivity between a left dorsolateral prefrontal cortex, and a left precuneus and a left posterior cingulate cortex; and a second functional connectivity between a left inferior frontal gyrus opercular part, and a right dorsomedial prefrontal cortex and a right supplementary motor area.

One embodiment of the present invention relates to a second classifier generating device including a processor and a storage device. The processor is configured to measure, for a plurality of subjects, a correlation at a first time point of a plurality of functional connectivities selected from among functional connectivity identification numbers 1 to 12 shown in Table 3, and a correlation at a second time point of the plurality of functional connectivities, the second time point being set to be after start of treatment and later than the first time point. In this embodiment, the processor is configured to generate a second classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point. The storage device is configured to store information for identifying the second classifier generated by the processor.

One embodiment of the present invention relates to a method of generating a second classifier. In this embodiment, for a plurality of subjects, there are measured a correlation at a first time point of a plurality of functional connectivities selected from among functional connectivity identification numbers 1 to 12 shown in Table 4, and a correlation at a second time point of the plurality of functional connectivities, the second time point being set to be after start of treatment and later than the first time point. In this embodiment, the method includes a step of generating in advance a classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point.

One embodiment of the present invention relates to a brain activity training device including a brain activity detecting apparatus, a presentation device, a processor, and a storage device. In this embodiment, the brain activity detecting apparatus is configured to detect, time-sequentially, a signal indicating a brain activity of a plurality of predetermined regions of a brain of a trainee of neurofeedback training. The storage device is configured to store: information for identifying a functional connectivity to be trained from among a plurality of functional connectivities selected by feature selection to discriminate a disease label of a depressive symptom through machine learning from among functional connectivities of a plurality of predetermined regions of each brain of a plurality of participants based on a signal obtained by measuring, in advance and time-sequentially, a signal indicating a brain activity of the plurality of predetermined regions of each brain of the plurality of participants in a resting state, the plurality of participants including healthy individuals and patients with depression; and a target pattern of the functional connectivity to be trained in the neurofeedback training. The processor is configured to execute processing of the neurofeedback training including: calculating a temporal correlation of the functional connectivity to be trained for a predetermined period of time based on the signal detected by the brain activity detecting apparatus; calculating a reward value in accordance with a degree of similarity with the target pattern based on the calculated temporal correlation; and presenting information indicating a magnitude of the reward value to the trainee via the presentation device. In this case, the functional connectivity to be trained includes a first functional connectivity between a left dorsolateral prefrontal cortex, and a left precuneus and a left posterior cingulate cortex, and each of the plurality of predetermined regions of the brain of the trainee corresponds to each of the plurality of predetermined regions of each brain of the plurality of participants.

One embodiment of the present invention relates to a method of controlling a brain activity training device, the brain activity training device including a brain activity detecting apparatus, a presentation device, a processor, and a storage device. In this embodiment, the brain activity detecting apparatus is configured to detect time-sequentially a signal indicating a brain activity of a plurality of predetermined regions of a brain of a trainee of neurofeedback training, and the storage device is configured to store: information for identifying a functional connectivity to be trained from among a plurality of functional connectivities selected by feature selection to discriminate a disease label of a depressive symptom through machine learning from among functional connectivities of a plurality of predetermined regions of each brain of a plurality of participants based on a signal obtained by measuring, in advance and time-sequentially, a signal indicating a brain activity of the plurality of predetermined regions of each brain of the plurality of participants in a resting state, the plurality of participants including healthy individuals and patients with depression; and a target pattern of the functional connectivity to be trained in the neurofeedback training. The method includes the steps of: detecting, by the brain activity detecting apparatus, time-sequentially, the signal indicating the brain activity of the plurality of predetermined regions of the brain of the trainee of neurofeedback training; calculating, by the processor, a temporal correlation of the functional connectivity to be trained for a predetermined period of time based on the signal detected by the brain activity detecting apparatus; calculating, by the processor, a reward value in accordance with a degree of similarity with the target pattern based on the calculated temporal correlation; and presenting, by the processor, information indicating a magnitude of the reward value to the trainee via the presentation device. In this case, the functional connectivity to be trained includes a first functional connectivity between a left dorsolateral prefrontal cortex, and a left precuneus and a left posterior cingulate cortex, and each of the plurality of predetermined regions of the brain of the trainee corresponds to each of the plurality of predetermined regions of each brain of the plurality of participants.

Advantageous Effects of Invention

According to the present invention, it is possible to provide the discriminating device and discriminating method for discriminating an indicator for the state of the depressive symptom with respect to the active state of the brain in an objective manner. According to the present invention, it is possible to discriminate information representing the degree of a therapeutic effect on the depressive symptom in an objective manner. According to the present invention, it is possible to provide the classifier configured to output the indicator value serving as a biomarker for discriminating the depressive symptom in an objective manner. According to the present invention, it is possible to discriminate the level of the depressive symptom. According to the present invention, it is possible to classify a patient with depression in an objective manner.

According to the present invention, it is possible to perform the neurofeedback training.

BRIEF DESCRIPTION OF DRAWINGS

FIG. 1 is a schematic diagram for illustrating an overall configuration of an MRI apparatus 10.

FIG. 2 is a hardware block diagram of a data processing unit 32.

FIG. 3 is a conceptual diagram for illustrating a procedure of extracting a correlation matrix representing a correlation between functional connectivities for a region of interest under a resting state.

FIG. 4 is a conceptual diagram for illustrating a process of generating a first classifier based on the correlation matrix.

FIG. 5 is a functional block diagram for executing processing of generating the first classifier as illustrated in FIG. 4 and discriminating processing by the generated first classifier.

FIG. 6 is a flow chart for illustrating processing to be executed by the data processing unit 32 to generate the first classifier.

FIG. 7 are each a conceptual diagram for illustrating inner loop feature extraction.

FIG. 8 is a diagram for illustrating a concept of inner loop feature extraction processing.

FIG. 9 is a diagram for illustrating results of iterative processing at the time of performing inner loop feature extraction for specific hyper parameters $\lambda_1$ and $\lambda_2$ as an example.

FIG. 10 is a flow chart for illustrating the inner loop feature extraction processing in more detail.

FIG. 11 is a conceptual diagram for illustrating outer loop feature extraction.

FIG. 12 is a flow chart for illustrating outer loop feature extraction processing in more detail.

FIG. 13 is a diagram for illustrating a concept of processing of generating a classifier in Step S108.

FIG. 14 is a flow chart for discriminating a depressive symptom for a subject.

FIG. 15 is a functional block diagram for illustrating an exemplary case in which data collection, estimation processing, and measurement of a brain activity of a subject are processed in a distributed manner.

FIG. 16 is a flow chart for discriminating a level of the depressive symptom for the subject.

FIG. 17-1 is a flow chart for discriminating a therapeutic effect for the subject.

FIG. 17-2 is a flow chart for discriminating the therapeutic effect for the subject.

FIG. 18 is a flow chart for discriminating a subclass of depression.

FIG. 19 is a functional block diagram for executing processing of generating a classifier and classification processing by the generated classifier.

FIG. 20 is a functional block diagram for illustrating an exemplary case in which data collection, estimation processing, and measurement of the brain activity of the subject, which are illustrated in FIG. 19, are processed in a distributed manner.

FIG. 21 is a flow chart for generating a second classifier.

FIG. 22 is a flow chart for determining efficacy by using the second classifier.

FIG. 23 is a functional block diagram for executing processing of generating the second classifier and therapeutic effect discriminating processing by the generated second classifier.

FIG. 24 is a flow chart for determining efficacy by using the second classifier for the subject for which the subclass of depression is determined.

FIG. 25 shows selected 12 pairs of functional connectivities.

FIG. 26 is a graph for showing a distribution of the size of 54 non-zero $c_i{}^k$.

FIG. 27*a* shows a distribution of a related weighted sum of cohorts of Hiroshima. FIG. 27*b* shows a distribution of a related weighted sum of cohorts of Chiba. FIG. 27*c* shows results of considering discrimination records by replacing training data and test data, where †p<0.10, *p<0.05, and **p<0.01.

FIG. 28*d* shows a smoothed histogram of a related weighted sum of a melancholic MDD group, and FIG. 28*e* shows a smoothed histogram of a related weighted sum of a non-melancholic MDD group, where †p<0.10, *p<0.05, and **p<0.01.

FIG. 29*f* shows a smoothed histogram of a related weighted sum of a treatment-resistant MDD group, FIG. 29*g* shows a smoothed histogram of a related weighted sum of an ASD group, and FIG. 29*h* shows a smoothed histogram of a related weighted sum of an SSD group, where †p<0.10, *p<0.05, and **p<0.01.

FIG. 30 show results of a permutation test. FIG. 30*a* shows a histogram of a permutation test (repetition of 1,000 times) by LOOCV for training data. FIG. 30*b* shows an accuracy of an out-of-sample test data set, and shows a binomial distribution as a curve. The accuracy of a melancholic MDD classifier trained and validated without permutation is indicated by a vertical line. The results of the permutation test were significant for the LOOCV (p=0.049) and out-of-sample validation (p=0.036), where *p<0.05.

FIG. 31*a* shows a correlation (all MDDs and healthy individuals) between BDI scores and results of discrimination by the first classifier. FIG. 31*b* shows a correction (all MDDs) between BDI and the results of discrimination by the first classifier. FIG. 31*c* shows a smoothed histogram of a related weighted sum before and after treatment. FIG. 31*d* shows a correlation between a change in BDI score after drug administration and a change in result of determination by the first classifier.

FIG. 32*a* shows a difference in correlation between a healthy control group and an MDD group in each functional connectivity, and a difference in correlation between before drug administration and after drug administration. FIG. 32*b* shows a difference in correlation between before drug administration and after drug administration in FC1 and FC2 for cohorts of Hiroshima. FIG. 32*c* shows a difference in correlation between before drug administration and after drug administration in FC1 and FC2 for cohorts of Chiba. FIG. 32*d* shows a difference in correlation between before drug administration and after drug administration in FC1 and FC2 for cohorts of a healthy individual.

FIG. 33*e* shows a difference in correlation between before drug administration and after drug administration in FC1 and FC2 for a remitted group after drug administration and a non-remitted group after drug administration. FIG. 33*f* shows a distribution of signed ΔFC1 and ΔFC2 in the drug administration group.

FIG. 34 is a diagram for illustrating a concept of a configuration of a brain activity training device.

FIG. 35 shows an example of display on a monitor for representing closeness between an indicator value and a target value.

FIG. 36 is a diagram for illustrating an example of a training sequence in neurofeedback.

FIG. 37*a* shows a neurofeedback score during a training period of an MDD participant. FIG. 37*b* shows an HDRS score before and after training of an MDD participant. FIG. 37*c* shows a neurofeedback score during a training period of a participant with subclinical depression. FIG. 37*d* shows a correlation between an amount of change in BDI score and an amount of change in rs-fc MRI after training.

FIG. 38 is a flow chart for illustrating neurofeedback training.

DESCRIPTION OF EMBODIMENTS

Now, a description is given of embodiments of the present invention with reference to the drawings. In the following description, components and processing steps with the same reference symbols indicate the same or corresponding components and processing steps, and a description thereof is not repeated unless otherwise necessary.

1. Description of Terms

In the present invention, the depressive symptom includes at least one type selected from among: depressed mood; decline in interest; decline in willpower; impatience; inhibition; diminished ability to think, concentrate, or make decisions; worthless feeling or guilty feeling; suicide, suicidal ideation, or suicide attempt; pathological thinking; delusion; physical symptoms (such as general malaise, headache, head dullness, pains of various parts of body such as backache, palpitation, shortness of breath, loss of appetite, and weight loss); and sleep disorder. The depressive symptom preferably includes a symptom accompanying a major depressive disorder (MDD) based on the standard of the Diagnostic and Statistical Manual of Mental Disorders (DSM)-IV.

In the present invention, depression is not limited as long as the depressive symptom is accompanied, but is preferably MDD. MDD includes a melancholic MDD, a non-melancholic MDD, and a treatment-resistant MDD. Herein, MDD is sometimes simply referred to as "depression".

As evaluation of the degree of depression, for example, hitherto, evaluation using Beck Depression Inventory by self-declaration has been used for screening at the time of medical examination or an auxiliary material at the time of consultation. Further, Hamilton Depression Rating Scale (HDRS), which is used as a scale for evaluation by a doctor, is a multiple item questionnaire providing an indicator for depression, and serves as an indicator for evaluating recovery. Its abbreviation is "HAM-D".

In the present invention, although the subject is not limited, the subject is preferably a person having the depressive symptom. The age or sex is not limited. The subject may be a person who has not received treatment for improving the depressive symptom, or may be a person who has received the treatment.

The treatment for improving the depressive symptom includes at least one type selected from pharmacotherapy, neurofeedback therapy, modified electroconvulsive therapy, and repetitive transcranial magnetic stimulation. An example of the drug to be administered may be at least one type selected from among: tricyclic antidepressants (e.g., imipramine, trimipramine, clomipramine, amitriptyline, nortriptyline, amoxapine, lofepramine, and dosulepine), tetracyclic antidepressants (e.g., maprotiline, mianserin, and setiptiline), trazodone, selective serotonin reuptake inhibitors (e.g., escitalopram, fluvoxamine, paroxetine, and sertraline), serotonin-norepinephrine reuptake inhibitors (e.g., milnacipran and duloxetine), noradrenergic and serotonergic antidepressants (e.g., mirtazapine), and benzamide-based drugs (e.g., sulpiride).

The treatment of the depressive symptom does not have a concept of "healing", and thus improvement of the depressive symptom means a state in which the depressive symptom is improved more than a past state in terms of a clinical finding, for example, a BDI, or a state of being "remitted" in terms of a clinical finding.

Embodiments of the present invention include assisting in determination of a level of the depressive symptom of the subject, assisting in determination of whether the subject has a depressive symptom, assisting in determination of a therapeutic effect for the subject, and assisting in classification of the subject into a subclass of the disease.

In the present invention, drug re-profiling is intended to refer to detection of efficacy for a depressive symptom with respect to a drug whose efficacy for another disease or symptom of a human is already revealed, or a drug that has weak toxicity for a human but is revealed not to have significant efficacy, and whose influence on the depressive symptom is unknown.

2. Imaging Condition of Resting-State fMRI and Extraction of Correlation Matrix

An imaging apparatus of the resting-state fMRI is not limited. The imaging condition is not also limited as long as an fMRI image can be acquired. For example, the magnetic field is about 3.0 T, the field of view is from about 192 mm to about 256 mm, the matrix is about 64×64, the number of slices is from about 30 to about 40, the number of volumes is from about 112 to about 244, the slice thickness is from about 3.0 mm to about 4.0 mm, the slice gap is from about 0 mm to about 0.8 mm, TR is from about 2,000 ms to about 2,700 ms, TE is from about 25 ms to about 31 ms, the total imaging time is from about 5 minutes to about 10 minutes, the flip angle is from about 75 deg to about 90 deg, and the slice acquisition order is ascending (interleaved). Imaging is preferably performed under dark illumination. Further, the subject preferably stays awake without thinking anything during imaging. Further, the subject preferably keeps looking at a crosshair mark on the center of a monitor screen during imaging.

The taken fMRI image can be processed by a method described in the literature (Nature Communications|7: 11254|DOI: 10.1038/ncomms11254) by Yahata et al.

The taken fMRI image data is not particularly limited, but, for example, SPM8 (Wellcome Trust Center for Neuroimaging, University College London, UK) of Matlab R2014a (Mathworks Inc., USA) can be used to perform standard preprocessing of a T1-weighted structural image and a resting-state functional image. For example, it is possible to perform realignment, slice-timing correction, coregistering, normalization, and smoothing (FWHM=8 mm) for a taken image. Further, an image determined to have moved with respect to a previous image by 0.5 mm or more may be excluded from analysis for all the image data of each subject.

A functional connectivity (FC) (namely, connectivity strength) is calculated for a plurality of predetermined regions of interest (ROI) inside the brain based on image data subjected to the preprocessing. The functional connectivity is a feature (element of correlation matrix) generally used in resting-state brain activity analysis, and is defined by a Pearson correlation coefficient between time-series signals of different regions of interest. For example, a connectivity strength can be represented by an average value of Pearson correlation coefficients based on values measured for a predetermined period of time, although the manner of representation is not particularly limited. Alternatively, the connectivity strength may be represented by other statistical amounts for the Pearson correlation coefficient within a predetermined period of time.

As described later, in this embodiment, in order to discriminate the state of the depressive symptom, the functional connectivity (connectivity strength) is calculated for all or a part of regions of interest with functional connectivity identification numbers ("ID" in Table 1) 1 to 12 shown in Table 1, for example.

TABLE 1

| ID | Name | Lat. | BSA atlas (Sulcus) | BA | rControl | rMDD | Weight |
|---|---|---|---|---|---|---|---|
| 1 | Precuneus/Posterior Cingulate Cortex | L | Internal parietal sulcus | 7, 23, 31 | −0.063 | 0.121 | 3.88 |
|  | Middle Frontal Gyrus, Dorsolateral Prefrontal Cortex (DLPFC) | L | Intermediate frontal sulcus | 46 |  |  |  |
| 2 | Supplementary Motor Area (SMA, Pre-SMA), Frontal Eye Fields, Dorsomedial Prefrontal Cortex | R | Median frontal sulcus | 6, 8, 9 | 0.175 | −0.017 | −3.34 |
|  | Inferior Frontal Gyrus opercular part | L | Diagonal ramus of the lateral fissure | 44 |  |  |  |

TABLE 1-continued

| ID | Name | Lat. | BSA atlas (Sulcus) | BA | rControl | rMDD | Weight |
|---|---|---|---|---|---|---|---|
| 3 | Thalamus | L | Thalamus | — | 0.210 | 0.051 | −2.61 |
| | Anterior Cingulate Cortex, Posterior Cingulate Cortex | R | Subcallosal sulcus | 23, 24, 33 | | | |
| 4 | Precuneus | L | Superior parietal sulcus | 7 | −0.155 | 0.014 | 1.99 |
| | Inferior Frontal Gyrus opercular part | L | Diagonal ramus of the lateral fissure | 44 | | | |
| 5 | Inferior Frontal Gyrus opercular part | R | Inferior precentral sulcus | 44 | 0.408 | 0.288 | −2.38 |
| | Inferior Frontal Gyrus Triangular part | L | Inferior frontal sulcus | 45 | | | |
| 6 | Nucleus Accumbens | R | Accumbens | — | 0.010 | 0.134 | 2.22 |
| | Anterior Cingulate Cortex, Posterior Cingulate Cortex | R | Subcallosal sulcus | 23, 24, 33 | | | |
| 7 | Lingual Gyrus | L | Anterior intralingual sulcus | 18 | 0.074 | 0.163 | 2.75 |
| | Middle Occipital Gyrus | R | Lobe occipital | 19 | | | |
| 8 | Postcentral Gyrus (Gustatory Area) | R | Central sylvian sulcus | 43 | −0.137 | −0.004 | 1.73 |
| | Occipital Lobe (Visual Area) | L | Lobe occipital | 17, 18, 19 | | | |
| 9 | Superior Parietal Gyrus (Somatosensory Area) | L | Superior postcentral sulcus | 5 | 0.076 | −0.022 | −1.93 |
| | Inferior Temporal Gyrus, Fusiform Gyrus | L | Median occipito-terrporal lateral sulcus | 20, 37 | | | |
| 10 | Rolandic operculum, Supramarginal Gyrus (Auditory Area) | R | Posterior lateral fissure | 40, 41, 48 | 0.066 | 0.168 | 1.75 |
| | Orbitofrontal Cortex, Insular Cortex, Inferior Frontal Gyrus Orbital part | R | Anterior lateral fissure | 12, 13, 47 | | | |
| 11 | Occipital Lobe (Visual Association Area) | L | Posterior intra-lingual sulcus | 18 | −0.144 | −0.052 | 1.59 |
| | Anterior Cingulate Cortex, Posterior Cingulate Cortex, Precuneus (Somatosensory Association Area) | L | Calloso-marginal posterior fissure | 5, 7, 23, 24, 31, 33 | | | |
| 12 | SMA, Pre-SMA, Frontal Eye Fields, DLPFC | R | Median frontal sulcus | 6, 8, 9 | 0.207 | 0.115 | −1.37 |
| | Anterior Cingulate Cortex (ACC) | L | Calloso-marginal anterior fissure | 32 | | | |

In Table 1, "L" and "R" of "Lat." represent a left brain and a right brain in a distinguished manner. "BSA" represents Brodmann's area, and "BA" represents the number of a Brodmann's area. "Weight" represents the weight of a related weighted sum (hereinafter sometimes referred to as just "weighted sum") described later.

Extraction of elements of the correlation matrix is not particularly limited, but can be performed in the following procedure, for example.

First, time-series average signals of all the voxels included in each region of interest are extracted. Next, the time-series average signals are subjected to a bandpass filter (from 0.008 Hz to 0.1 Hz) to remove noises of those signal values. After that, 9 explanatory variables (average signals of whole brain, white matter, and cerebrospinal fluid, and 6 body motion correction parameters) are used to perform regression. A residual sequence after regression is considered to be a time-series signal value relating to the functional connectivity, the time-series signal value is set as an element of each region of interest, and a time-series Pearson correlation coefficient is calculated for elements of each correlation matrix of each pair of regions of interest. The correlation coefficient is a value representing the connectivity strength of a functional connectivity, and the connectivity strength corresponding to each pair is acquired.

The correlation coefficient of each functional connectivity is input to a classifier described later as input data, and on the basis of the correlation coefficient and a coefficient representing a weight (degree of contribution) calculated in advance for each functional connectivity for executing classification processing by the classifier, an indicator value for discriminating the disease label of a depressive symptom for the functional connectivity is calculated. In other cases, a related weighted sum for a plurality of functional connectivities is calculated as an indicator value for discriminating the disease label of the depressive symptom based on the correlation coefficient and the coefficient. The term "related weighted sum" herein refers to a value obtained by multiplying a plurality of functional connectivities by corresponding weights and taking a sum thereof.

Thus, the indicator value is not data obtained by simply measuring the brain activity of a subject, but a value calculated artificially in consideration of the weight of each functional connectivity. The indicator value is used for discrimination of the label of the depressive symptom, discrimination of the level of the depressive symptom, discrimination of the therapeutic effect, or classification of a patient with depression.

A functional connectivity with the functional connectivity identification number 1 contributes to the depressive symptom most among the 12 pairs of functional connectivities. A functional connectivity with the functional connectivity identification number 2 contributes the second most. Thus, in each embodiment described below, at least one or both of the functional connectivity identification number 1 and the functional connectivity identification number 2 may be selected to be used.

The 12 pairs of functional connectivities are particularly appropriate for discriminating a melancholic MDD patient group and a healthy control group.

3. Generation of First Classifier and Discriminating Device

The first classifier is generated by classifier generation processing based on a signal obtained by using a brain activity detecting apparatus to measure, in advance and time-sequentially, a signal indicating a brain activity of a plurality of predetermined regions of each brain of a plurality of participants in a resting state, the plurality of participants including healthy individuals and patients with depression. The term "patient with depression" refers to a participant who is diagnosed with depression in a diagnosis by a doctor in advance and is associated with "disease label" of depression. The classifier is generated so as to discriminate the disease label of the depressive symptom based on the weights of functional connectivities selected by feature selection as being relevant to the disease label of the depressive symptom through machine learning from among functional connectivities of the plurality of predetermined regions.

Specifically, as described later, a functional connectivity to be used for discrimination of the disease label of depression is selected by feature selection by sparse logistic regression from among functional connectivities extracted by sparse canonical correlation analysis as being specifically relevant to the disease label of the depressive symptom from among functional connectivities of a plurality of regions of interest set in advance. Then, the above-mentioned related weighted sum is calculated based on the functional connectivities selected in this manner.

3-1. Discriminating Device 1

For example, the first classifier is generated from fMRI image data acquired from an MRI apparatus 10 illustrated in FIG. 1.

FIG. 1 is a schematic diagram for illustrating an overall configuration of the MRI apparatus 10 being a discriminating device 1 according to a first embodiment of the present invention.

As illustrated in FIG. 1, the MRI apparatus 10 includes an MRI imaging unit 25 configured to perform MRI imaging and a data processing unit 32 configured to set a control sequence for the MRI imaging unit 25 and process various kinds of data signals, to thereby generate an image. The MRI imaging unit 25 includes a magnetic field applying mechanism 11 configured to apply a magnetic field that is controlled to target a region of interest of a subject 2 to radiate an RF wave, and a reception coil 20 configured to receive a response wave (NMR signal) from this subject (or trainee) 2 to output an analog signal, and a driving unit 21 configured to control a magnetic field to be applied to the subject 2 and control transmission or reception of an RF wave.

A central axis of a cylindrical bore in which the subject 2 is to be placed is set as a Z axis, and a horizontal direction and a vertical direction orthogonal to the Z axis are set as an X axis and a Y axis, respectively.

The MRI apparatus 10 has such a configuration, and thus the nuclear spin of atomic nuclei forming the subject 2 is oriented in a magnetic field direction (Z axis) by a static magnetic field applied by the magnetic field applying mechanism 11, and performs precession at a Larmor frequency specific to those atomic nuclei with this magnetic field direction serving as an axis.

Then, when the same RF pulse as that of this Larmor frequency is radiated, the atoms resonate with each other to absorb energy to be excited, with the result that a nuclear magnetic resonance (NMR) phenomenon occurs. When radiation of an RF pulse is stopped after this resonation, atoms output an electromagnetic wave (NMR signal) with the same frequency as that of the Larmor frequency in a relaxation process of emitting energy and returning to their original steady states.

The reception coil 20 receives this output NMR signal as a response wave from the subject 2, and the data processing unit 32 processes a region of interest of the subject 2 to form an image.

The magnetic field applying mechanism 11 includes a static magnetic field generating coil 12, a magnetic field gradient generating coil 14, an RF irradiating unit 16, and a bed 18 to be used to place the subject 2 in the bore.

The subject 2 lies face up on the bed 18, for example. The subject 2 can, for example, though not particularly limited, use prism eyeglasses 4 to view a screen displayed on a presentation device 6 (e.g., display) installed vertically with respect to the Z axis. The subject 2 receives a visual stimulus through an image of the presentation device 6. The subject

2 may receive a visual stimulus through a configuration in which an image is projected by a projector in front of the subject 2.

Such a visual stimulus corresponds to presentation of feedback information in the above-mentioned neurofeedback.

The driving unit 21 includes a static magnetic field power supply 22, a gradient magnetic field power supply 24, a signal transmission unit 26, a signal reception unit 28, and a bed driving unit 30 for moving the bed 18 to any position in the Z-axis direction.

The data processing unit 32 includes an input unit 40 configured to receive various kinds of operations or input of information from an operator (not shown), a display unit 38 configured to display, on a screen, various kinds of images or various kinds of information on a region of interest of the subject 2, a storage unit 36 configured to store programs for executing various kinds of processing, control parameters, image data (e.g., structure image), and other electronic data, a control unit 42 configured to control operation of each functional unit, for example, generation of a control sequence for driving the driving unit 21, an interface unit 44 configured to execute transmission/reception of various kinds of signals to/from the driving unit 21, a data collection unit 46 configured to collect data including a group of NMR signals originating from a region of interest, an image processing unit 48 configured to form an image based on this NMR signal data, and a network interface unit 50 for executing communication through a network.

Further, in addition to the case of the data processing unit 32 being a dedicated computer, the data processing unit 32 may be a general-purpose computer configured to execute a function for operating each functional unit, and may perform specified calculation, data processing, or generation of the control sequence based on a program installed in the storage unit 36. Now, a description is given based on the assumption that the data processing unit 32 is a general-purpose computer.

The static magnetic field generating coil 12 is configured to cause a current supplied from the static magnetic field power supply 22 to flow through a helical coil wound around the Z axis to generate an induction field, to thereby generate a static magnetic field in the bore in the Z-axis direction. A region of interest of the subject 2 is set in a region having a highly constant static magnetic field formed in the bore. More specifically, the static magnetic field generating coil 12 includes four air-core coils, for example, and a combination thereof forms a constant magnetic field internally, and the spin of predetermined atomic nuclei inside the body of the subject 2, more specifically, the spin of hydrogen atomic nuclei, is given orientation.

The magnetic field gradient generating coil 14 includes an X coil, a Y coil, and a Z coil (not shown), and is provided on an inner peripheral surface of the static magnetic field generating coil 12 having a cylindrical shape.

Those X coil, Y coil, and Z coil switch the X-axis direction, Y-axis direction, and Z-axis direction in order, respectively, to thereby superimpose a gradient magnetic field on the constant magnetic field in the bore and apply a strength gradient to the static magnetic field. The Z coil applies a gradient to the magnetic field intensity in the Z-axis direction to limit a resonant face at the time of excitation, the Y coil applies a gradient for a short period of time immediately after application of the magnetic field in the Z-axis direction to add a phase modulation proportional to a Y coordinate to a detected signal (phase encoding), and the X coil next applies a gradient at the time of collection of data to add frequency modulation proportional to an X coordinate to the detected signal (frequency encoding).

Switching of the gradient magnetic field to be superimposed is implemented by the transmission unit 24 outputting a pulse signal different for each of the X coil, the Y coil, and the Z coil in accordance with the control sequence. With this, it is possible to identify the position of the subject 2 exhibiting an NMR phenomenon, and position information of three-dimensional coordinates required for forming an image of the subject 2 is given.

As described above, three orthogonal gradient magnetic fields can be assigned a slice direction, a phase encoding direction, and a frequency encoding direction, respectively, to thereby perform imaging from various angles by a combination thereof. For example, in addition to a transverse slice in the same direction as that of imaging by an X-ray CT apparatus, imaging can be performed for a sagittal slice and a coronal slice orthogonal thereto, and for an oblique slice in which a direction perpendicular to the surface is not parallel to the axes of the three orthogonal gradient magnetic fields, for example.

The RF irradiating unit 16 is configured to radiate a radio frequency (RF) pulse to a region of interest of the subject 2 based on a high frequency signal transmitted from the signal transmission unit 33 in accordance with the control sequence.

In FIG. 1, the RF irradiating unit 16 is incorporated in the magnetic field applying mechanism 11, but may be provided in the bed 18, or may be integrated with the reception coil 20.

The reception coil 20 is configured to detect a response wave (NMR signal) from the subject 2, and is arranged near the subject 2 in order to detect this NMR signal with high sensitivity.

In the reception coil 20, a minute current is caused based on electromagnetic induction when an electromagnetic wave of the NMR signal cuts the coil wire. This minute current is amplified in the signal reception unit 28, and is converted from an analog signal into a digital signal for transmission to the data processing unit 32.

That is, the following configuration is adopted. When the RF irradiating unit 16 applies a high frequency electromagnetic field with a resonance frequency to the subject 2 in a state in which a Z-axis gradient magnetic field is applied to the static magnetic field, predetermined atomic nuclei of a portion satisfying a resonance condition in terms of the strength of the magnetic field, for example, hydrogen atomic nuclei, are excited selectively and start to resonate. Predetermined atomic nuclei of a portion (e.g., section with predetermined thickness of subject 2) satisfying the resonance condition are excited, and spins rotate all at once. When an excitation pulse is stopped, in the reception coil 20, the electromagnetic wave emitted by the rotating spins next excites a signal, and this signal is detected for a while. With this signal, tissues containing predetermined atoms inside the body of the subject 2 are observed. Then, a signal is detected by applying X and Y gradient magnetic fields in order to grasp the position of emission of the signal.

The image processing unit 48 measures a detection signal while at the same time repeatedly producing an excitation signal based on data constructed in the storage unit 36, reduces the resonance frequency into an X coordinate by first Fourier transform calculation, obtains an image by restoring the Y coordinate by second Fourier transform, and displays a corresponding image on the display unit 38.

For example, with such an MRI system, the above-mentioned BOLD signal is imaged in real time, and the control unit 42 executes analysis processing as described later for a chronologically taken image, to thereby enable imaging of the resting-state functional connectivity MRI (rs-fc MRI).

FIG. 2 is a hardware block diagram of the data processing unit 32.

As described above, the hardware of the data processing unit 32 is not particularly limited, but a general-purpose computer can be used as the hardware.

In FIG. 2, in addition to a memory drive 2020 and a disk drive 2030, a computer main body 2010 of the data processing unit 32 includes a processor (central processing unit: CPU) 2040, a bus (also called "interface") 2050 connected to the disk drive 2030 and the memory drive 2020, a read-only memory (ROM) 2060 for storing a program, for example, a booting program, a random access memory (RAM) 2070 for temporarily storing a command of an application program and providing a temporary memory space, a non-volatile storage device 2080 for storing an application program, a system program, and data, and a communication interface 2090. The communication interface 2090 corresponds to the interface unit 44 for transmitting/receiving a signal to/from the driving unit 21, for example, and a network interface 50 for communicating to/from other computers via a network (not shown). A hard disk drive (HDD), a solid state drive (SSD), or the like can be used as the non-volatile storage device 2080. The non-volatile storage device 2080 corresponds to the storage unit 36. The computer main body 2010 of the data processing unit 32 also functions as a first classifier generating device and/or a second classifier generating device.

The CPU 2040 executes arithmetic processing based on a program to implement each function of the data processing unit 32, for example, each function of the control unit 42, the data collection unit 46, and the image processing unit 48.

The program for causing the data processing unit 32 to execute the above-mentioned function of the embodiment is stored in a CD-ROM 2200 or a memory medium 2210, and is inserted into the disk drive 2030 or the memory drive 2020. Further, the program may be transferred to the non-volatile storage device 2080. The program is loaded onto RAM 2070 at the time of execution of the program.

The data processing unit 32 further includes a keyboard 2100 and a mouse 2110 serving as input devices, and a display 2120 serving as an output device. The keyboard 2100 and the mouse 2110 correspond to the input unit 40, and the display 2120 corresponds to the display unit 38.

The program for implementing such a function of the data processing unit 32 as described above may not always include an operating system (OS) for executing the function of, for example, an information processing device in the computer main body 2010. The program may include only such a command as to call an appropriate function (module) in a controlled mode to obtain a desired result. The manner of operation of the data processing unit 32 is widely known, and thus a detailed description thereof is omitted here.

Further, there may be a single or plurality of computers for executing the program. That is, any of centralized processing and distributed processing may be performed.

FIG. 3 is a conceptual diagram for illustrating a procedure of extracting a correlation matrix representing a correlation between functional connectivities under a resting state relating to the disease label of the depressive symptom.

As illustrated in FIG. 3, an average "degree of activity" of regions of interest is calculated based on fMRI data equivalent to n (n: natural number) time points of fMRI in a resting state measured in real time, and a correlation value for the degrees of activity of brain regions (regions of interest) is calculated.

In this case, 137 regions excluding small brain regions are considered as the region of interest, and thus the number of independent non-diagonal components in the correlation matrix is:

$$(137 \times 137 - 137)/2 = 9316,$$

in consideration of symmetry. On FIG. 3, the correlation indicates only 34×34 components.

Calculation of elements of such a correlation matrix is not particularly limited, but for example, can be performed in the following manner.

The functional connectivity between different regions of interest is calculated for each participant based on the resting-state brain activity data. The functional connectivity is a feature generally used in resting-state brain activity analysis, and is defined by a Pearson correlation coefficient between time-series signals of different regions of interest.

First, time-series average signals of all the voxels included in each region of interest are extracted.

Next, the time-series average signals are subjected to a bandpass filter to remove noises of those signal values. After that, 9 explanatory variables (average signals of whole brain, white matter, and cerebrospinal fluid, and 6 body motion correction parameters) are used to perform regression.

A residual sequence after regression is considered to be a time-series signal value relating to the functional connectivity, and a time-series Pearson correlation coefficient is calculated for different ROIS.

As the region of interest, 137 regions of interest included in the Brain Sulci Atlas (BAL) are used. A functional connectivity FC among those 137 regions of interest is used as the feature.

The following disclosure is known for the Brain Sulci Atlas (BAL).

Literature: Perrot et al., Med Image Anal, 15(4), 2011
Literature: Tzourio-Mazoyer et al., Neuroimage, 15(1), 2002

FIG. 4 is a conceptual diagram for illustrating a process of generating the first classifier being a biomarker based on such a correlation matrix as illustrated in FIG. 3.

As described below, for example, the first classifier functions as an indicator being a diagnostic marker for "depression", and can be used for assisting a doctor in diagnosing the degree of severity or progression of a disease. Thus, an apparatus configured to calculate the first classifier and output results can also be referred to as "diagnosis assisting apparatus".

As illustrated in FIG. 4, the data processing unit 32 derives elements of a correlation matrix of the degrees of activity of brain regions (regions of interest) for each participant by a procedure as described later based on fMRI data measured for participants including a group of healthy individuals and a group of patients with depression, which has been imaged by the MRI imaging unit 25.

Next, the data processing unit 32 extracts a feature by regularized canonical correlation analysis for the correlation matrix and the attribute of a participant including a disease/healthy individual label of the participant. In machine learning or statistics, the term "regularization" generally refers to a method of adding a regularized term weighted by hyperparameters to an error function, and suppressing the complexity or degree of freedom of a model, to thereby prevent overtraining. As a result of regularized canonical correlation analysis, when an explanatory variable is subjected to sparsification as well, the regularized canonical correlation analysis is particularly called "sparse canonical correlation analysis (SCCA)". Now, a description is given of a specific example in which sparse canonical correlation analysis is performed.

Then, in such sparse canonical correlation analysis, as described later, the value of a hyperparameter is adjusted to produce a canonical variable connecting only to the "disease label", and extract a functional connectivity FC connecting to the corresponding canonical variable. A sum-set of functional connectivities FC extracted within a range in which there are canonical variables satisfying such a condition when the hyperparameter is changed within a predetermined range is referred to as a "first sum-set".

Further, the "first sum-set" obtained as a result of sparse regularized canonical correlation analysis by the data processing unit 32 is set as an explanatory variable, and for example, discriminant analysis by sparse logistic regression is performed in each cross validation step while at the same time performing leave-one-out cross validation (LOOCV). A sum-set of functional connectivities FC extracted as explanatory variables over all the cross validation is referred to as a "second sum-set".

Lastly, discriminant analysis by sparse logistic regression is performed for the "disease label" being an objective variable with the "second sum-set" serving as an explanatory variable for data on all the participants, to thereby generate the first classifier.

FIG. 5 is a functional block diagram for executing processing of generating the first classifier as illustrated in FIG. 4 and discriminating processing by the generated first classifier.

First, the non-volatile storage device 2080 stores rs-fc MRI participant measurement data 3102 being information obtained by using the MRI apparatus to measure, in advance and time-sequentially, a signal indicating a brain activity of a plurality of predetermined regions of each brain of a plurality of participants including healthy individuals and patients with depression, and a plurality of pieces of human attribute information 3104 associated with respective participants whose MRI measurement data has been measured.

The term "human attribute information" herein includes "human characteristic information" for identifying a participant, and "measurement condition information" for identifying a measurement condition for each participant.

The term "human characteristic information" refers to information on a participant such as the disease label, age, sex, or medication history.

The term "measurement condition information" refers to a condition for identifying a measurement condition such as information on a measurement site (including information for identifying measurement facility and/or measurement apparatus) at which the participant has been measured, whether measurement has been performed with opened eyes or closed eyes during measurement, or measured magnetic field intensity.

The processor 2040 executes processing of generating a classifier for the disease label based on the rs-fc MRI participant measurement data 3102 and the corresponding human attribute information 3104.

The correlation matrix calculation unit 3002 calculates, for each participant, a correlation matrix of functional connectivities of the brain activities of a plurality of predetermined regions based on the rs-fc MRI participant measurement data 3102. Data on the calculated correlation matrix of functional connectivities is stored into the non-volatile storage device 2080 for each participant as data 3106 of the correlation matrix of functional connectivities.

A first feature selection unit 3004 sequentially selects one subset for different K (K: natural number of 2 or more) subsets extracted from a plurality of participants, and performs sparse canonical correlation analysis for a plurality of pieces of attribute information and elements of the correlation matrix for (K−1) subsets excluding the selected subset, to thereby extract specific attribute information among the plurality of pieces of human attribute information, for example, an element of the correlation matrix connecting to a canonical variable corresponding only to the disease label. Further, the first feature selection unit 3004 acquires a first sum-set being a sum-set of elements of the extracted correlation matrix for the sequentially selected subsets, and stores the first sum-set into the non-volatile storage device 2080 as first functional connectivity sum-set data 3108. The "first functional connectivity sum-set data" may also be an index for identifying elements corresponding to the first sum-set within the data 3106 of the correlation matrix of functional connectivities.

When remaining participants excluding the K subsets among the plurality of participants are set as a test set, and the test set is divided into N different groups, a second feature selection unit 3006 calculates, by sparse logistic regression, a test classifier for estimating the specific attribute information (e.g., disease label) based on the first sum-set for a set of participants among the plurality of participants excluding one selected group among the N groups, and extracts elements of the correlation matrix being explanatory variables of the test classifier due to sparsification. The second feature selection unit 3006 further sequentially selects one group from among the N groups, repeats feature extraction to acquire a second sum-set being a sum-set of elements of the correlation matrix extracted as explanatory variables of the test classifier, and stores the second sum-set into the non-volatile storage device 2080 as second functional connectivity sum-set data 3110. The "second functional connectivity sum-set data" may also be an index for identifying elements corresponding to the second sum-set within the data 3106 of the correlation matrix of functional connectivities.

The number of elements of each of N groups may be one.

A classifier generation unit 3008 calculates the first classifier for estimating the specific attribute information (e.g., disease label) by sparse logistic regression with the second sum-set serving as an explanatory variable. The classifier generation unit 3008 stores information for identifying the generated first classifier into the non-volatile storage device 2080 as classifier data 3112.

The discriminating processing unit 3010 executes discriminating processing for input data based on the classifier identified by the classifier data 3112.

In the above description, the second sum-set is set as an explanatory variable, and the classifier generation unit 3008 generates the classifier. However, for example, the classifier generation unit 3008 may directly generate the first classifier with the first sum-set serving as an explanatory variable. However, as described later, it is desired that the second sum-set be set as an explanatory variable in terms of reduction of the dimension and generalization performance.

In generation of the first classifier, regularized logistic regression being logistic regression using a regularization method (e.g., L1 regularization or L2 regularization) can be used, and more specifically, for example, the above-mentioned "sparse logistic regression" can also be used. Further, in generation of the first classifier, for example, a support vector machine or linear discriminant analysis (LDA) may be used. In the following, a description is given by taking sparse logistic regression as an example.

As described later, in parallel to feature selection processing by the second feature selection unit 3006, one group excluded from the N groups may be sequentially selected, and the test classifier calculated by the second feature selection unit 3006 may be used to calculate a discrimination result with the excluded group serving as a test sample, to thereby perform cross-validation.

In this manner, reduction of the dimension of the explanatory variable is performed by the procedure of feature selection in nested structure, to thereby be able to reduce the number of dimensions efficiently in terms of time while at the same time using data of almost all of the participants in the processing executed by the second feature selection unit 3006.

Further, the test set in the processing of the second feature selection unit 3006 is set to be independent of a data set used for reducing the number of dimensions, to thereby be able to avoid an extremely optimistic result.

FIG. 6 is a flow chart for illustrating processing to be executed by the data processing unit 32 to generate the classifier being a biomarker.

Now, a description is given of the processing illustrated in FIG. 4 in more detail with reference to FIG. 6.

The most critical problem in the case of creating a biomarker based on connection between brain regions derived from the resting-state fMRI data and the discrimination label (disease label) of the disease of a participant is that the number of dimensions of data is much larger than the number of pieces of data. Thus, when the data set is used for the classifier to perform learning for predicting the disease label (label indicating whether or not participant has disease is referred to "disease label") without regularization, overfitting occurs and the performance of predicting unknown data drastically deteriorates.

Meanwhile, in general machine learning, processing of explaining measurement data with a smaller number of explanatory variables is referred to "feature selection (or feature extraction)". In this embodiment, among a "plurality of correlation values (plurality of connectivities) of degrees of activity of brain regions (regions of interests)", such feature selection (feature extraction) as to enable construction of the first classifier by a smaller number of correlation values, that is, selection of a more important correlation coefficient as an explanatory variable, may be referred to as "extraction of reduced representation" in machine learning of the first classifier for predicting the target disease label.

Further, in this embodiment, the regularization method is used as the feature extraction method. In this manner, such processing is referred to as "sparse canonical correlation analysis" in consideration of execution of regularization, sparsification, and processing of selecting more important explanatory variables in canonical correlation analysis. More specifically, for example, as the regularization method for implementing sparsification in combination, a method of imposing a penalty on the size of the absolute value of a parameter of canonical correlation analysis, namely, "L1 regularization" as described later can be used.

Specifically, referring to FIG. 6, when the data processing unit 32 starts processing of generating the classifier in response to, for example, input of start of processing from the input unit 40 (Step S100), the data processing unit 32 reads MRI measurement data for each participant from the storage unit 36 (Step S102), and executes processing of extracting a first feature by sparse canonical correlation analysis (SCCA) (Step S104).

The processing of Step S104 is hereinafter referred to as "inner loop feature extraction".

Now, a description is given of each of the "sparse canonical correlation analysis" and the "inner loop feature extraction" below to describe the processing of the inner loop feature extraction in Step S104.

(Sparse Canonical Correlation Analysis)

Now, a description is given of L1 regularized canonical correlation analysis as the sparse canonical correlation analysis. This L1 regularized canonical correlation analysis is disclosed in the following literature.

Literature: Witten D M, Tibshirani R, and T Hastie. A penalized matrix decomposition, with applications to sparse principal components and canonical correlation analysis. Biostatistics, Vol. 10, No. 3, pp. 515-534, 2009.

First, in general canonical correlation analysis (CCA), regarding a pair of data $x_1$ and $x_2$, the variables $x_1$ and $x_2$ are normalized to have an average of 0 and a standard deviation of 1.

In general, the CCA can be used to identify a potential relationship between a pair of measurement amounts.

Specifically, in the CCA, a projection vector is retrieved to find a maximum correlation between the pair of projected variables (canonical variable).

In contrast, when L1 regularization is applied to canonical correlation analysis, that is, when sparse CCA due to L1-norm regularization, namely, L1-SCCA is used, the following optimization problem is solved.

Now, the following combination of variables is considered.

When there are a combination of measurement amounts each [Math. 1] including $N$ elements of variables $x_1 \in R^{p1}$ and $x_2 \in R^{p2}$, it is assumed that $X_1 = \left[x_1^1, x_1^2, \cdots x_1^N\right]^T$ represents an $N \times p_1$ matrix being a combination of first variables, and $X_2 = \left[x_2^1, x_2^2, \cdots x_2^N\right]^T$ represents an $N \times p_2$ matrix being a combination of second variables.

Also in this case, it is assumed that columns forming the matrices $X_1$ and $X_2$ are normalized to have an average of 0 and a variance of 1.

Then, L1-SCCA can be formulated into the following Expression (1).

[Math. 2]

$$\max_{w_1, w_2} w_1^T X_1^T X_2 w_2 \text{ subject to } \|w_1\|_1^2 \le \lambda_1, \|w_2\|_1^2 \le 1, \|w_2\|_2^2 \le 1 \quad (1)$$

In the expression given above, hyperparameters $\lambda_1$ and $\lambda_2$ represent the degrees of sparsification of weight parameters $w_1$ and $w_2$ (referred to as "sparse projection vectors" because corresponding variables are subjected to sparsification due to $w_1$ and $w_2$), respectively.

Specifically, in the examples of this embodiment, it is assumed that two data matrices corresponding to the above-mentioned variables are constructed in order to identify a potential relationship between human attribute information and a functional connectivity FC.

In the following, the participants include a group of patients with depression (with disease label of "major depressive disorder (MDD)") and a healthy control group (with disease label of "healthy control (HC)"), and the first row of the data matrix $X_1$ represents human attribute information (human characteristic information and measurement condition information) on one participant, and for example, the characteristic information and measurement condition information include the following items.

i) Disease label (MDD or HC)

ii) Site information (indicating where brain activity of participant has been measured, namely, sites A, B, and C)

iii) Age iv) Sex v) Imaging condition (opened eyes or closed eyes)

vi) State of drug administration 1 (antipsychotic)

vii) State of drug administration 2 (antidepressant)

viii) State of drug administration 3 (tranquilizer)

Specifically, the number of columns of the human attribute information data matrix $X_1$ is 10, that is, $p_1=10$.

The first column includes 1 (=MDD) or 0 (=HC).

The next three columns indicate a facility (location) at which the brain activity has been measured, and in this case, include any one of [100] (site A), [010] (site B), and [001] (site C) depending on measurement at three different sites.

The fifth column includes the value of the age of a participant. The sixth column is information on the sex of a participant, and includes a value indicating any one of "1" (male) and "0" (female). The seventh column indicates whether a participant opened eyes or closed eyes during measurement among measurement conditions, and includes the value of "1" (opened eyes) or "0" (closed eyes). Further, the last three columns include three pieces of status information on the medication history, and each column includes the value of "1" (there is history of drug treatment) or "0" (there is no history of drug treatment).

The human characteristic information and the measurement condition information are not limited to the above-mentioned items, and for example, may include other characteristics such as information on the medication histories of other drugs of a participant, or information on other measurement conditions, for example, the size of an applied magnetic field of the MRI apparatus.

It is assumed that, in the second data matrix $X_2$, elements of a lower non-diagonal triangular part of the correlation matrix representing a correlation (FC) between functional connectivities of a participant are represented in a row vector format.

Further, L1-SCCS is applied to the pair of matrices $X_1$ and $X_2$, and then sparse projection vectors $w_1$ and $w_2$ are derived.

Further, as described above, the first data matrix $X_1$ is set to satisfy such a condition that the first data matrix $X_1$ is projected to canonical variables of specific human attribute information, namely, canonical variables with only "disease label" in this case by the sparse projection vector $w_1$ due to sparsification when the hyperparameters $\lambda_1$ and $\lambda_2$ are set to predetermined values. In this case, in the corresponding second data matrix $X_2$, a sparse projection vector $w_2$ is used to identify an index (element) for identifying a correlation matrix element of the functional connectivity associated only with the disease label.

That is, in the inner loop feature extraction, the hyperparameters $\lambda_1$ and $\lambda_2$ of L1-SCCA are changed independently of each other between 0.1 and 0.9 in units of 0.1, for example.

However, the range in which the hyperparameters $\lambda_1$ and $\lambda_2$ are set to be variable and the unit of change of the hyperparameters $\lambda_1$ and $\lambda_2$ are not limited to this example.

Regarding the processing of L1-SCCA, a range of hyperparameters $\lambda_1$ and $\lambda_2$ in which there are canonical variables connecting only to the "disease" label are found.

Projection of original correlation matrix elements onto a subspace defined by non-zero elements of the derived sparse projection vector $w_2$ is represented in the following manner.

A variable $i_k$ is defined to indicate an index of a k-th non-zero element of the projection vector $w_2$. In this case, $1 \le k \le m$ is satisfied, and m represents the number of non-zero elements.

Then, a projection matrix E, which is obtained by projection onto the following subspace, is considered.

$$E = [e_{i1}, e_{i2}, \cdots, e_{im}]^T \qquad \text{[Math. 3]}$$

where $e_{ik} \in R^{p2}$ is a standard basis vector containing "1" as an $i_k$-th element and containing "0" as other elements.

Lastly, the original correlation matrix element vector $x_2$ is projected in the following manner to derive a vector in a subspace $z \in R^m$.

[Math. 4]

$$z = E x_2 \qquad (2)$$

As a result, only a specific number of features (elements of correlation matrix) associated with the disease label (MDD/HC) can be selected.

Correlation matrix elements essential for classification are selected by selecting correlation matrix elements corresponding to canonical variables associated only with the diagnosis label.

(Inner Loop Feature Extraction)

FIG. 7 are a conceptual diagram for illustrating the inner loop feature extraction.

In the inner loop feature extraction of Step S104 of FIG. 6, a set of participants is divided into K sets (K: natural number of 2 or more) as illustrated in FIG. 7, and the above-mentioned L1-SCCA is executed for (K−1) times for remaining subsets excluding one set among (K−1) subsets.

That is, as illustrated in FIG. 7(a), subsets (hereinafter referred to as "inner loop training data") corresponding to (K−1)/K (e.g., 8/9 when K=9) within the set of participants are used for such inner loop feature extraction. The remaining one among the K subsets is used as "test pool" including test data to be used for training in outer loop feature extraction described later, and thus is not used in the inner loop feature extraction.

As illustrated in FIG. 7(b), L1-SCCA is executed for remaining subsets excluding one set (indicated by oblique lines in FIG. 7(b)) among (K−1) subsets by changing the hyperparameters $\lambda_1$ and $\lambda_2$ in units of predetermined steps within predetermined ranges. A functional connectivity element FC related to a canonical variable associated only with the "diagnosis" label within the ranges of specific hyperparameters $\lambda_1$ and $\lambda_2$ is extracted as a feature.

Such extraction processing is repeated for subsets for which one set to be excluded is changed in order among the (K−1) subsets.

In each repetition, a sum-set of elements FC of the correlation matrix of the extracted functional connectivities is set as a "sum-set of functional connectivity elements FC selected in inner loop" (first sum-set).

Through such processing, an inappropriate influence caused by a difference in human attribute information at different imaging sites or in imaging condition at different imaging sites, which corresponds to a nuisance variable NV, is reduced.

As described later, this procedure is useful for constructing a robust first classifier generalized to a foreign country, for example, the United States, based on the first classifier generated based on MRI measurement data obtained at a plurality of imaging sites in Japan, for example.

Referring back to FIG. 6, next, the data processing unit 32 uses sparse logistic regression to execute second feature extraction processing based on the result of the inner loop feature extraction (Step S106).

The processing of Step S106 is hereinafter referred to as "outer loop feature extraction".

Now, a description is given of each of "sparse logistic regression" and "outer loop feature extraction" in order to describe the processing of the outer loop feature extraction in Step S106.

(Sparse Logistic Regression)

The sparse logistic regression is a method of extending logistic regression analysis to the framework of Bayesian estimation, and is a method of performing dimension compression of a feature vector and weight estimation for discrimination at the same time. This method is useful when the number of dimensions of the feature vector of data is extremely large, and a large amount of unrequired features are contained. The weight parameter in linear discriminant analysis is set to 0 for an unrequired feature (that is, feature selection is performed), and only a small amount of features related to discrimination are retrieved (sparsity).

In the sparse logistic regression, a probability p of the obtained feature data belonging to a class to be classified is acquired for each class, and the feature data is assigned to a class that has output the maximum value. The probability p is output by a logistic regression expression. Estimation of the weight is performed by automatic relevance determination (ARD), and a feature that contributes less to class discrimination is excluded from calculation because the weight approaches 0.

Specifically, the first sum-set of features extracted by using the above-mentioned L1 regularized CCA is input to use the first classifier based on next hierarchical Bayesian estimation and predict the disease label.

At this time, logistic regression is used as the classifier to predict a probability of the diagnosis label being the disease (diagnosis of autism in this case) based on feature input z (selected FC) extracted in Expression (2) given above.

[Math. 5]

$$p(y = 1 \mid \theta) = \frac{1}{1 + \exp\left(-\theta^T \hat{z}\right)} \qquad (3)$$

In the expression given above, y represents a diagnosis class/label, that is, y=1 represents an MDD class, and y=0 represents an HC class.

Further, the following z hat ("^" assigned to top of letter is referred to as "hat") is a feature vector including extended input.

$$\hat{z} = \left[z^T, 1\right]^T \in R^{m+1} \qquad \text{[Math. 6]}$$

The feature vector z is extracted in accordance with Expression (2) based on a connectivity correlation matrix of MRI samples of one participant in the resting state.

Use of extended input "1" is a standard approach for introducing certain (bias) input into the first classifier.

The following $\theta$ is a parameter vector of a logistic function.

$$\theta \in R^{m+1} \qquad \text{[Math. 7]}$$

The distribution of the parameter $\theta$ in this case is set to the following normal distribution.

$$p(\theta \mid \alpha) = N(\theta \mid 0, \operatorname{diag}(\alpha)) \qquad \text{[Math. 8]}$$

Further, the distribution of a hyperparameter $\alpha$ for the distribution of a parameter w is set in the following manner, to thereby estimate the distribution of each parameter by performing hierarchical Bayesian estimation.

$$p(\alpha) = \prod_{j} \Gamma\left(\alpha_i \mid a^0, b^0\right) \qquad \text{[Math. 9]}$$

In the expression given above, $a^0$ and $b^0$ represent parameters for determining the gamma distribution of a hyperparameter. Symbol $\alpha$ is a parameter vector representing the variance of the normal distribution of the vector $\theta$, and an i-th element of the vector is $\alpha_i$.

Such sparse logistic regression is disclosed in the following literature.

Literature: Okito Yamashita, Masa aki Sato, Taku Yoshioka, Frank Tong, and Yukiyasu Kamitani. "Sparse Estimation automatically selects voxels relevant for the decoding of fMRI activity patterns." NeuroImage, Vol. 42, No. 4, pp. 1414-1429, 2008.

(Outer Loop Feature Extraction)

FIG. 11 is a conceptual diagram for illustrating the outer loop feature extraction.

In the outer loop feature extraction in Step S106 of FIG. 6, a set of participants is divided into K subsets (K: natural number of 2 or more) as illustrated in FIG. 11 at the time of the inner loop feature extraction, and the remaining one subset excluding (K−1) subsets used for the inner loop feature extraction is used as "test pool" including test data to be used for training.

That is, as illustrated in FIG. 11, for example, this test pool is divided into L groups, and one group (indicated by oblique lines within dotted square of FIG. 11) is selected in order from among the L groups. Then, the first classifier for predicting the disease label is generated by sparse logistic regression for a set of participants excluding the selected group with the first sum-set of functional connectivity elements FC of the correlation matrix serving as an explanatory variable. At this time, the "elements FC of the correlation matrix of functional connectivities" are additionally selected by sparse logistic regression. This is referred to as "elements FC of correlation matrix of functional connectivities selected in outer loop".

In this manner, one group is selected in order from among L groups, and such processing is repeated L times to set a sum-set of elements FC of the correlation matrix of the extracted functional connectivities as a "sum-set of functional connectivity elements FC selected in outer loop" (second sum-set).

In this manner, a test set to be used for outer loop feature extraction is always independent of a data set used for reducing the number of dimensions in the inner loop feature extraction.

As an example, it is particularly assumed that each of the L groups includes one participant. In this case, in the above-mentioned repetition processing, prediction processing by the generated first classifier for one excluded participant, and processing of accumulating an error between the disease label and the prediction result for one excluded participant correspond to performing so-called leave-one-out cross validation (LOOCV). Therefore, in the processing of FIG. 11, the above-mentioned error can be calculated in each repetition processing to be accumulated, and then averaged over L times, to thereby be able to perform cross validation of the generated first classifier, that is, evaluation of the generalization capability as well.

(Generation of First Classifier)

Referring back to FIG. 6, the data processing unit 32 next executes processing of generating the classifier by sparse logistic regression based on the result (second sum-set) of the outer loop feature extraction (Step S108).

FIG. 13 is a diagram for illustrating a concept of the processing of generating the classifier in Step S108.

As illustrated in FIG. 13, in Step S108, the classifier is generated by sparse logistic regression for all the participants with the second unit extracted by the outer loop feature extraction from the first sum-set serving as an explanatory variable.

Classifier data (data on function form and parameter) 3112 for identifying the generated classifier is stored into the non-volatile storage device 2080, and after that, when MRI measurement data (test data) different from that used for the above-mentioned training is input, the classifier data is used for discriminating processing at the time of estimating the disease label for test data.

That is, a correlation (connectivity) of the degrees of activity of brain regions (regions of interest) of participants classified into a group of healthy individuals and a group of patients with depression is measured based on preliminary diagnosis by a doctor, and a classifier, which has been generated so as to discriminate whether test data for a new different participant corresponds to any one of the depressive symptom and the healthy state through machine learning for a measurement result, functions as a biomarker for the depressive symptom.

At this time, the classifier is generated by logistic regression, and thus the "disease label" being an output of the biomarker may include a probability (or probability of being healthy) of having a disease. For example, such display as the "probability of having a disease is oo %" is output. Such a probability can be used as a "disease marker".

Further, the attribute output by the classifier is not always limited to discrimination of a disease, and may be output of another attribute. Also in this case, a discrete discrimination result of which class the attribute belongs to may be output, or a continuous value of the attribute intrinsic to some class, for example, a probability may be output.

That is, in learning (creation) of the classifier, in order to create a biomarker for the depressive symptom, rs-fc MRI data is input to extract a feature by the above-mentioned inner loop feature extraction and outer loop feature extraction, and the classifier generated with the extracted feature serving as an explanatory variable is used to discriminate between the depressive symptom label and the healthy individual label.

(Processing of Inner Loop Feature Extraction)

FIG. 8 is a diagram for illustrating a concept of the inner loop feature extraction processing.

FIG. 9 is a diagram for illustrating results of iterative processing at the time of performing the inner loop feature extraction for the specific hyperparameters $\lambda_1$ and $\lambda_2$ as an example.

Referring to FIG. 8, one repetition of L1-SCCA is represented in feature selection having nested structure, and in this case, the canonical variable is connected only to the "disease label".

In FIG. 8, the fact that the canonical variable is connected only to the "disease label" is represented by connection of the disease label to only one canonical variable $w_1{}^T x_1$ by a solid line.

Further, a symbol $c_j$ on a dotted line connecting the canonical variable $w_1{}^T x_1$ to a canonical variable $w_2{}^T x_2$ each represents a correlation coefficient between canonical variables.

When the canonical variable $w_1{}^T x_1$ is connected only to the "disease label", elements of a lower non-diagonal triangular part of the correlation matrix of functional connectivities connected to the corresponding canonical variable $w_2{}^T x_2$ are extracted as a feature.

As an example, FIG. 9 shows a combination of smallest hyperparameters that generate at least one canonical correlation for each piece of human attribute information in the first outer loop.

The canonical variable is represented by a circle.

A circle on the left column represents the canonical variable $w_1{}^T x_1$ due to the human characteristic information and measurement condition. Meanwhile, a circle on the right column represents the canonical variable $w_2{}^T x_2$ due to the functional connectivity (FC).

As described above, a number on a dotted line connecting canonical variables represents a correlation coefficient between the canonical variables $w_1{}^T x_1$ and $w_2{}^T x_2$.

The label of human attribute information and connection to the canonical variable $w_2{}^T x_2$ are represented by a solid line or a dotted line.

(Processing of Inner Loop Feature Extraction)

FIG. 10 is a flow chart for illustrating the inner loop feature extraction processing in more detail.

In the inner loop feature extraction, a set of participants is divided into K subsets as illustrated in FIG. 7(*a*), and the remaining (K−1) subsets excluding one specific subset among the K subsets are used.

Referring to FIG. 10, when the inner loop feature extraction processing is started, an arithmetic processing device (CPU) 2040 sets the hyperparameters $\lambda_1$ and $\lambda_2$ to $(\lambda_1, \lambda_2)=(0.1, 0.1)$ being an initial value (Step S200).

Next, the value of the variable i is set to 1 (Step S202), and when the value of i does not exceed the number of times (K−1) of repetition of the inner loop feature extraction (N in Step S204), the CPU 2040 executes sparse canonical correlation analysis based on the human attribute information 3104 on a participant and the correlation matrix data 3106 of functional connectivities, which are stored in the non-volatile storage device 2080 except for an i-th data block among pieces of inner loop training data (Step S206).

When there is a canonical variable connecting only to the disease label for a current combination of values $(\lambda_1, \lambda_2)$ (Y in Step S208), the CPU 2040 extracts elements (FC) of the correlation matrix of functional connectivities corresponding to the canonical variable connecting only to the disease label, and stores the elements into the non-volatile storage device 2080 (Step S210). After the processing of Step S210, or when there is no canonical variable connecting only to the disease label for a current combination of values $(\lambda_1, \lambda_2)$ (N in Step S208), the CPU 2040 increments the value of i by 1, and the processing returns to Step S204.

Thus, the CPU 2040 repeats the processing of Step S206 to Step S212 for (K−1) times.

In Step S204, when the value of i exceeds the number of times (K−1) of repetition of the inner loop feature extraction (Y in Step S204), the CPU 2040 changes any one of $\lambda_1$ and $\lambda_2$ by a predetermined step amount in accordance with a predetermined rule for $(\lambda_1, \lambda_2)$ (Step S214). In Step S216, when the value of $(\lambda_1, \lambda_2)$ falls within a variable range (Y in Step S216), the CPU 2040 returns the processing to Step S202.

When the processing is finished for all the possible combinations of values $(\lambda_1, \lambda_2)$ (N in Step S216), the CPU 2040 acquires a sum-set of elements (FC) of the correlation matrix of functional connectivities extracted in the processing executed so far, and stores the sum-set into the non-volatile storage device 2080 as the first functional connectivity sum-set data 3108, to thereby finish the processing.

(Processing of Outer Loop Feature Extraction)

FIG. 12 is a flow chart for illustrating the outer loop feature selection processing in more detail.

In the outer loop feature extraction, a set of participants is divided into K subsets as illustrated in FIG. 11, and one subset that has not been used in the inner loop feature extraction among the K subsets is used as a test pool. The number of participants included in this test pool is set to be NT.

Further, in the following, a description is given on the assumption that leave-one-out cross validation (LOOCV) processing is executed as an example.

Referring to FIG. 12, when the outer loop feature extraction processing is started, the arithmetic processing device (CPU) 2040 sets the value of the variable i to 1 (Step S300), and when the value of i does not exceed the number of times NT of repetition of the outer loop feature extraction (N in Step S302), the CPU 2040 executes sparse logistic regression (SLR) to generate the test classifier based on the human attribute information 3104 on a participant and the correlation matrix data 3106 on functional connectivities, which are stored in the non-volatile storage device 2080, except for an i-th piece of data within the test pool (Step S304).

Next, the CPU 2040 uses the generated test classifier to calculate a prediction value by SLR for the excluded i-th piece of data (Step S306).

Further, the CPU 2040 stores the functional connectivity FC extracted by sparsification at the time of generating the test classifier into the non-volatile storage device 2080 as the extracted feature, and increments the value of the variable i by 1 (Step S310).

After the processing of Step S304 to Step S308 is repeated NT times, when the value of the variable i exceeds NT (Y in Step S302), the CPU 2040 calculates an estimation of a square error as LOOCV (Step S312).

Next, the CPU 2040 acquires a sum-set (second sum-set) of the extracted functional connectivities FC by repetition processing of NT times, and stores the sum-set into the non-volatile storage device 2080 as the second functional connectivity sum-set data 3110, to thereby finish the processing.

(Processing of Generating Classifier)

FIG. 13 is a conceptual diagram for illustrating a procedure of generating the definitive first classifier.

As illustrated in FIG. 13, in the classifier generation processing, the inner loop feature extraction processing and the outer loop feature extraction processing are performed to generate the first classifier by sparse logistic regression for all the participants with the definitively extracted second functional connectivity sum-set data 3110 serving as an explanatory variable. Information (e.g., parameter vector θ of logistic function) for identifying the generated first classifier is stored in the non-volatile storage device 2080.

As described above, in the procedure described above, when "depression" is set as the disease label, 12 pairs of functional connectivities shown in Table 1 are used as explanatory variables of the definitively extracted second functional connectivity sum-set data 3110, and the first classifier is generated.

All the functional connectivities shown in Table 1 may be used for generation of the classifier represented by the logistic regression expression. However, at least one or both of the functional connectivity identification number 1 and the functional connectivity identification number 2 may be selected to be used. Further, a plurality of functional connectivities having a high degree of contribution may be selected. Such selection of the functional connectivity to be used for the classifier from among the 12 pairs of functional connectivities may be performed by the data processing unit 32 or the CPU of a computer 300 described later. However, selection may be manually performed.

(Discriminating Processing)

FIG. 14 is a flow chart for illustrating processing to be executed by the data processing unit 32 to discriminate the disease label based on rs-fc MRI data on a subject by using the generated first classifier.

In Step S401, the CPU 2040 acquires, via the interface unit 44, rs-fc MRI measurement data 3113 on a subject in the resting state from the MRI imaging unit 25.

The CPU 2040 executes the preprocessing described in the above-mentioned section "2." in Step S402 and Step S403, and extracts elements of a correlation matrix for all or a part of the functional connectivities shown in Table 1.

In Step S404, the CPU 2040 acquires a Pearson correlation coefficient for the extracted elements of the correlation matrix. In Step S405 and Step S406, the CPU 2040 inputs the correlation coefficient into the classifier, and generates an indicator value for discriminating the disease label of the depressive symptom for at least one functional connectivity. In other cases, the CPU 2040 desirably inputs the correlation coefficient into the classifier, and generates a related weighted sum for a plurality of functional connectivities as an indicator value for discriminating the disease label of the depressive symptom.

Next, in Step S407, the CPU 2040 compares the indicator value with a reference value. For example, in the logistic regression expression of Math. 5 as represented by Math. 6, a threshold value for the disease label of the depressive symptom and the label of the healthy individual are set to be 0, and thus the reference value is 0. For example, when the "related weighted sum" is used as the indicator value of the biomarker, the reference value may be set to a value different from 0 in order to adjust the sensitivity or specificity of the first classifier. For example, when the reference value is set to be smaller than 0, the sensitivity of discrimination of the disease level of "depression" is increased, whereas the specificity decreases. When the above-mentioned result of discrimination by the classifier is intentionally used as reference information (assistance information) for diagnosis by a doctor based on other subsequent information, the setting of prioritizing improvement of the sensitivity may be adopted.

In Step S408, when the indicator value is larger than 0 ("YES: Y"), the CPU 2040 can determine that the subject has the label of the depressive symptom (Step S409). On the contrary, when the indicator value is smaller than 0 ("NO: N"), the CPU 2040 can determine that the subject has the label of the depressive symptom (Step S410).

3-2. Discriminating Device 2

In the description of the first embodiment, the brain activity measuring apparatus (fMRI apparatus) is configured to measure brain activity data measured at one measurement location, and use the brain activity data to generate the classifier and estimate (predict) the disease label by the classifier through processing by the same computer or distributed processing.

However, the following configuration may be adopted: i) measurement of brain activity data for training the classifier by machine learning (data collection), ii) processing of generating the classifier by machine learning, and processing of estimating (predicting) the disease label by the classifier for a specific subject (estimation processing), and iii) measurement of brain activity data for the specific participant (brain activity measurement of subject) are executed at different facilities in a distributed manner.

Specifically, data on a group of healthy individuals and a group of patients with depression is not limited to the case of measurement by the MRI apparatus 10 itself, and pieces of data measured by other MRI apparatus may be integrated to generate the classifier. Further, more generally, the data processing unit 32 is not always required to be a computer for executing control of the MRI apparatus, but may be a dedicated computer configured to receive measurement data from one or a plurality of MRI apparatus, and execute the discriminating processing by the processing of generating the classifier and the generated classifier.

FIG. 15 is a functional block diagram for illustrating an exemplary case in which data collection, estimation processing, and measurement of the brain activity of the subject are processed in a distributed manner in another embodiment of the first embodiment of the present invention.

Referring to FIG. 15, sites 100.1 to 100.N are facilities in which the brain activity measuring apparatus measures data on participants including a group of patients with depression and a group of healthy individuals, and a management server 200 is configured to manage measurement data obtained at the sites 100.1 to 100.N.

The computer 300 serving as the discriminating device 2 is configured to generate the classifier based on data stored in the management server 200.

The MRI apparatus 410 is provided on another site that uses the result of the classifier on the computer 300, and is configured to measure brain activity data for a specific subject.

A computer 400 is installed on another site at which the MRI apparatus 410 is provided, and is configured to calculate correlation data of functional connectivities of the brain of a specific subject based on the measurement data of the MRI apparatus 410, transmit the correlation data of functional connectivities to the computer 300, and use the returned result of discrimination by the classifier.

The server 200 stores FMRI participant measurement data 3102 on a group of patients with depression and a group of healthy individuals, which are transmitted from the sites 100.1 to 100.N, and human attribute information 3104 on a participant associated with the fMRI participant measurement data 3102, and is configured to transmit those pieces of data to the computer 300 in response to access from the computer 300.

The computer 300 is configured to receive the fMRI participant measurement data 3102 and the human attribute information 3104 on a subject from the server 200 via the communication interface 2090.

The hardware configurations of the server 200, the computer 300, and the computer 400 are basically similar to those of the "data processing unit 32" illustrated in FIG. 2, and thus a description thereof is not repeated here.

Referring back to FIG. 15, the correlation matrix calculation unit 3002, the first feature selection unit 3004, the second feature selection unit 3006, the classifier generation unit 3008, the discriminating processing unit 3010, the data 3106 on the correlation matrix of functional connectivities, the first functional connectivity sum-set data 3108, the second functional connectivity sum-set data 3110, and the classifier data 3112 are similar to those described in the first embodiment, and thus a description thereof is not repeated here.

The MRI apparatus 410 is configured to measure brain activity data on a subject for which the diagnosis label is to be estimated, and a processing device 4040 of the computer 400 stores the measured MRI measurement data 4102 into a non-volatile storage device 4100.

Further, the processing device 4040 of the computer 400 is configured to calculate data 4106 on the correlation matrix of functional connectivities based on the MRI measurement data 4102 and the human attribute information on a subject to be measured by the MRI apparatus 410 similarly to the correlation matrix calculation unit 3002, and stores the data 4106 into the non-volatile storage device 4100.

A user of the computer 400 specifies a disease to be diagnosed, and the computer 400 transmits the data 4106 on the correlation matrix of functional connectivities to the computer 300 in accordance with a transmission instruction given by the user. In response to this, the discriminating processing unit 3010 calculates a result of discrimination for the specified diagnosis label, and the computer 300 transmits the result to the computer 400 via the communication interface 2090.

The computer 400 notifies the user of the result of discrimination via a display apparatus (not shown), for example.

With such a configuration, it is possible to provide the result of estimation of the diagnosis label by the classifier for a larger number of users based on data collected for a larger number of subjects.

Further, it is possible to employ a mode in which separate managers manage the server 200 and the computer 300. In that case, a computer that can access the server 200 is limited, to thereby be able to improve the security for information on subjects stored in the server 200.

Further, in terms of a subject of management of the computer 300, a "service of providing the discrimination result" can be performed without providing information on the classifier at all to a "side (computer 400) that receives the service of discrimination by the classifier".

3-4. Usage of Classifier and Discriminating Device

In addition to discrimination of the disease label of the depressive symptom, the discriminating devices 1 and 2 can be used for discriminating the level of the depressive symptom, generating information that has discriminated the degree of an effect of treatment of the depressive symptom, or generating assistance information at the time of classification of a subject into a subclass when the depressive symptom is already classified into a plurality of subclasses set in advance. How to use each of the discriminating devices 1 and 2 is described later.

The first classifier can be used as a diagnosis biomarker for discriminating the depressive symptom. Further, the first classifier can be used as a diagnosis biomarker for discriminating the level of the depressive symptom. The first classifier can be used as an efficacy marker for discriminating an effect of treatment of the depressive symptom. The first classifier can be used as a biomarker for classifying a subject into a subclass of depression.

3-5. Computer Program for Generating Classifier and Computer Program for Discriminating Depressive Symptom Another mode of the first embodiment includes a program for causing a computer to execute processing including Step S100 to Step S108 (specifically, including Step S200 to Step S218 and Step S300 to Step S314), to thereby execute the function of classifier generation processing, and a program for causing the computer to execute processing including Step S401 to Step S410, to thereby execute the function of discriminating processing. Further, another mode of the first embodiment includes a program for causing the computer to execute processing including Step S100 to Step S108 (specifically, including Step S200 to Step S218 and Step S300 to Step S314) and Step S401 to Step S410, to thereby execute the function of the discriminating device. Those programs may be stored in a storage medium, for example, a hard disk drive, a semiconductor memory element such as a flash memory, or an optical disc. The format of storage of a program into the storage medium is not limited as long as the CPU 2040 can read the program. The storage medium for storing a program is preferably a non-volatile storage medium.

3-6. Discriminating Method for Depressive Symptom

A second embodiment of the present invention relates to a discriminating method for a depressive symptom. The discriminating method includes a step of generating an indicator value for evaluating the depressive symptom for elements of a correlation matrix of functional connectivities measured for a subject in a resting state, and a step of determining that the subject has the depressive symptom when the indicator value exceeds a reference value. A specific procedure conforms to Step S401 to Step S410, but all or a part of the procedure may be manually performed except for the step of generating an indicator value.

4. Discriminating Device and Discriminating Method for Level of Depressive Symptom 4-1. Discriminating Device The discriminating device 1 and the discriminating device 2 can be used for discriminating the level of the depressive symptom. That is, a discriminating device for a level of a depressive symptom according to another mode of the first embodiment includes a processor and a storage device. This processor executes processing of generating, by using the first classifier based on a program stored in the storage device, an indicator value for evaluating the depressive symptom for elements of a correlation matrix of functional connectivities measured for a subject in a resting state. Then, the processor executes processing of comparing the indicator value with a reference range of the indicator value set in advance in accordance with a level of the depressive symptom for each functional connectivity, and determining that the subject has a level of the depressive symptom corresponding to the reference range including the indicator value. In this case, the configurations of the discriminating device 1 and the discriminating device 2 are similar to those described in the above-mentioned section "3.", and thus a description thereof is omitted here. The discriminating processing unit 3010 executes processing of discriminating input data based on the classifier identified by the classifier data 3112, and discriminates the level of the depressive symptom of the subject.

In this case, regarding discrimination of the "level of the depressive symptom", for example, a value that may be taken by the value of the "related weighted sum" being the indicator value is classified into a plurality of levels of reference ranges in advance, to thereby be able to output a discrimination result corresponding to the "level of the depressive symptom".

Alternatively, in this case, the "disease label" to be used for generating the classifier may be set in advance as a plurality of "levels of disease labels" that correspond to the level of depression, to thereby execute machine learning of the classifier.

4-2. Discriminating Method

A third embodiment of the present invention relates to a discriminating method for a level of a depressive symptom. The discriminating method includes a step of generating a indicator value for evaluating the depressive symptom for elements of a correlation matrix of functional connectivities measured for a subject in a resting state, a step of comparing the indicator value with a reference range of the indicator value set in advance in accordance with a level of the depressive symptom for each functional connectivity, and a step of determining that the subject has a level of the depressive symptom corresponding to the reference range including the indicator value.

FIG. 16 is a flow chart for illustrating processing to be executed by the data processing unit 32 to discriminate the level of the depressive symptom based on rs-fc MRI subject data by using the generated classifier.

The CPU 2040 receives, for example, input of start of processing from the input unit 40 to execute Step S401 to Step S406 illustrated in FIG. 14, to thereby generate an indicator value. Next, the CPU 2040 compares the indicator value with a reference range of the indicator value set in advance in accordance with the level of the depressive symptom in Step S501 illustrated in FIG. 16. The 12 pairs of functional connectivities correlate with, for example, the degree of severity of the depressive symptom based on BDI, and thus the reference range of the indicator value for determining the level of the depressive symptom can be determined in advance based on the correlation with the degree of severity of the depressive symptom based on BDI. In Step S502, the CPU 2040 determines which level of depressive symptom the indicator value generated in Step S406 of FIG. 14 corresponds to (Step S502). Then, in Step S503, the CPU 2040 determines that the subject has the level of the depressive symptom determined in Step S502. Regarding each step to be executed by the CPU 2040, all or a part of steps excluding the step of generating the indicator value may be manually performed.

Further, another mode of the third embodiment includes a program for causing a computer to execute processing including Step S501 to Step S503 described above, to thereby execute the function of the discriminating device. Another mode of the third embodiment includes a program for causing the computer to execute processing including Step S401 to Step S406 and Step S501 to Step S503 described above, to thereby execute the function of the discriminating device. Those programs may be stored in a storage medium, for example, a hard disk drive, a semiconductor memory element such as a flash memory, or an optical disc. The format of storage of a program into the storage medium is not limited as long as the CPU 2040 can read the program. The storage medium for storing a program is preferably a non-volatile storage medium.

5. Discriminating Device and Discriminating Method for Therapeutic Effect of Using First Classifier 5-1. Discriminating Device The discriminating device 1 and the discriminating device 2 can be used for generating information for discriminating a therapeutic effect. That is, a discriminating device for determining a therapeutic effect for a subject according to another mode of the first embodiment includes a processor and a storage device. The processor is configured to execute processing of: generating, by using the first classifier based on a program stored in the storage device, a first value for evaluating the depressive symptom for elements of a correlation matrix of functional connectivities measured for the subject in a resting state at a first time point; generating, by using the classifier, a second value for evaluating the depressive symptom for elements of a correlation matrix of the same functional connectivities as the above-mentioned functional connectivities inside a brain of the same subject as the above-mentioned subject in the resting state at a second time point, which is after start of treatment and later than the first time point; comparing the first value with the second value; and i) determining that the treatment is effective for improving the depressive symptom of the subject when the second value is improved more than the first value, and/or determining that the treatment is not effective for improving the depressive symptom of the subject when the second value is not improved more than the first value. In this case, the configurations of the discriminating device 1 and the discriminating device 2 are similar to those described in the above-mentioned section "3.", and thus a description thereof is omitted here. The discriminating processing unit 3010 executes processing of discriminating input data based on the classifier identified by the classifier data 3112, and generates information for discriminating the therapeutic effect for the subject.

Another mode of this mode includes using the discriminating device for drug reprofiling.

5-2. Discriminating Method

In a fourth embodiment of the present invention, the first classifier receives input of elements of a correlation matrix of functional connectivities shown in Table 1, which are acquired from resting-state fMRI data on a subject imaged at at least two time points, and generates information for discriminating a therapeutic effect. Specifically, the fourth embodiment includes a step of generating a first value for evaluating a depressive symptom for elements of a correlation matrix of functional connectivities measured for a subject in a resting state at a first time point, a step of generating a second value for evaluating the depressive symptom for elements of a correlation matrix of the same functional connectivities as the above-mentioned functional connectivities inside a brain of the same subject as the above-mentioned subject in the resting state at a second time point, a step of comparing the first value with the second value, and a step of determining that the treatment is effective for improving the depressive symptom of the subject when the second value is improved more than the first value, to thereby generate information indicating a possibility of being effective. The first time point may be a time point before treatment, or a time point after elapse of a predetermined period of time since start of the treatment. However, the first time point is preferably a time point before start of the treatment. Further, also when treatment is finished once and after that the treatment is resumed, a period of time since end of the treatment until the treatment is resumed may be defined as "before treatment". The second time point is not limited as long as the second time point is a time point after start of the treatment and later than the first time point.

FIG. 17 are flow charts for illustrating processing for discriminating the therapeutic effect based on fMRI data on a subject by using the first classifier.

In Step S601 illustrated in FIGS. 17, the CPU 2040 receives, for example, input of start of processing from the input unit 40 to acquire, via the interface unit 44, fMRI measurement data 3113 on a subject in the resting state, which has been obtained by imaging the subject by the MRI imaging unit 25 at the first time point.

In Step S602 and Step S603, the CPU 2040 executes the preprocessing described in the above-mentioned section "2.", and extracts elements of a correlation matrix at the first time point for all or a part of the functional connectivities selected from among 12 pairs of functional connectivities shown in Table 1.

In Step S604, the CPU 2040 calculates a Pearson correlation coefficient for the elements of the correlation matrix extracted in Step S603 at the first time point.

In Step S605 and Step S606, the CPU 2040 inputs the correlation coefficient calculated in Step S604 into the first classifier, and generates a first value for the selected functional connectivity. The first value is calculated as the indicator value described in the above-mentioned section "2.", for example.

The CPU 2040 acquires, via the interface unit 44, fMRI measurement data 3113 on a subject in the resting state, which has been obtained by imaging the subject by the MRI imaging unit 25 indicated in Step S607 at the second time point.

In Step S608 and Step S609, the CPU 2040 executes the preprocessing described in the above-mentioned section "2.", and extracts elements of the correlation matrix at the second time point for all or a part of the functional connectivities selected from among 12 pairs of functional connectivities shown in Table 1.

In Step S610, the CPU 2040 calculates a Pearson correlation coefficient for the elements of the correlation matrix extracted in Step S609 at the second time point.

In Step S611 and Step S612, the CPU 2040 inputs the correlation coefficient calculated in Step S610 into the first classifier, and generates a first value for the selected functional connectivity. The second value is generated as the indicator value described in the above-mentioned section "2.", for example.

The CPU 2040 compares the first value generated in Step S606 with the second value generated in Step S612 (Step S613).

When the CPU 2040 has determined that the second value is improved more than the first value in Step S614 ("YES: Y"), the CPU 2040 generates information indicating a state of the treatment relating to improvement of the depressive symptom of the subject (Step S615). In this case, the CPU 2040 may next proceed to Step S616 to present information indicating a possibility of continuation of the treatment. The doctor determines whether to continue the treatment based on the information indicating such a possibility of continuation of the treatment. For example, although not particularly limited, information of a preset region indicating effectiveness of the treatment may be displayed on an output screen in a distinctive manner, the "information indicating a state of the treatment" may be an indicator value to be output by the classifier, and "presenting information indicating a possibility of continuation of the treatment" may be to display this indicator value under a state in which the above-mentioned region is displayed.

Further, when the CPU 2040 has determined that the second value is not improved more than the first value in Step S614 ("NO: N"), the CPU 2040 generates information indicating a state of the treatment relating to improvement of the depressive symptom of the subject (Step S617). In this case, the CPU 2040 may next proceed to Step S618 to present information indicating a possibility that the treatment is to be finished.

The doctor determines whether to finish the treatment based on the information indicating such a possibility that the treatment is to be finished. For example, although not particularly limited, information of a preset region indicating no effectiveness of the treatment may be displayed on the output screen in a distinctive manner, the "information indicating a state of the treatment" may be an indicator value to be output by the classifier, and "presenting information indicating a possibility that the treatment is to be finished" may be to display this indicator value under a state in which the above-mentioned region is displayed.

Further, the CPU 2040 may proceed to Step S619 to present information indicating a possibility of changing the current treatment to another one. In this case, the CPU 2040 may present a possibility of a more specific treatment. In this case, the doctor can determine treatment to which the current treatment is to be changed among displayed potential treatments.

For example, in the expression represented by Math. 6, the threshold values for the disease label of the depressive symptom and the label of the healthy individual are set to 0, and thus the reference value is 0.

For example, when the "related weighted sum" is used as the indicator value of a biomarker, in Step S614, as the depressive symptom becomes severer, the indicator value becomes larger in the positive direction. Thus, the CPU 2040 can determine that the second value is improved more than the first value when the second value is smaller than the first value. Further, when the second value is larger than the first value, or when a significant difference between the first value and the second value is not recognized, the CPU 2040 can determine that the second value is not improved more than the first value.

The first value and the second value may be indicator values, but the correlation coefficients calculated in Step S604 and Step S610 may be set as the first value and the second value, respectively.

Further, in the third embodiment, Step S601 is required to be performed before Step S607. However, Step S602 to Step S606 are not required to be performed before Step S607. Step S602 to Step S606 are only required to be performed after Step S601 and somewhere before Step S613 at least.

All or a part of Step S601 to Step S619 may be manually performed.

The third embodiment can also be used for determining an effect of drug treatment. When the effect of drug administration is determined by using the first classifier, functional connectivities with at least the functional connectivity identification numbers 1 and 2 are preferably set as indicators.

Another mode of the fourth embodiment includes using the determination method for drug reprofiling.

Further, another mode of the fourth embodiment includes a program for causing a computer to execute processing including Step S601 to Step S619 described above, to thereby execute the function of the discriminating device. This program may be stored in a storage medium, for example, a hard disk drive, a semiconductor memory element such as a flash memory, or an optical disc. The format of storage of a program into the storage medium is not limited as long as the CPU 2040 can read the program. The storage medium for storing a program is preferably a non-volatile storage medium.

6. Classification Device and Classification Method for Patient with Depression

6-1. Classification Device

Figure 20:
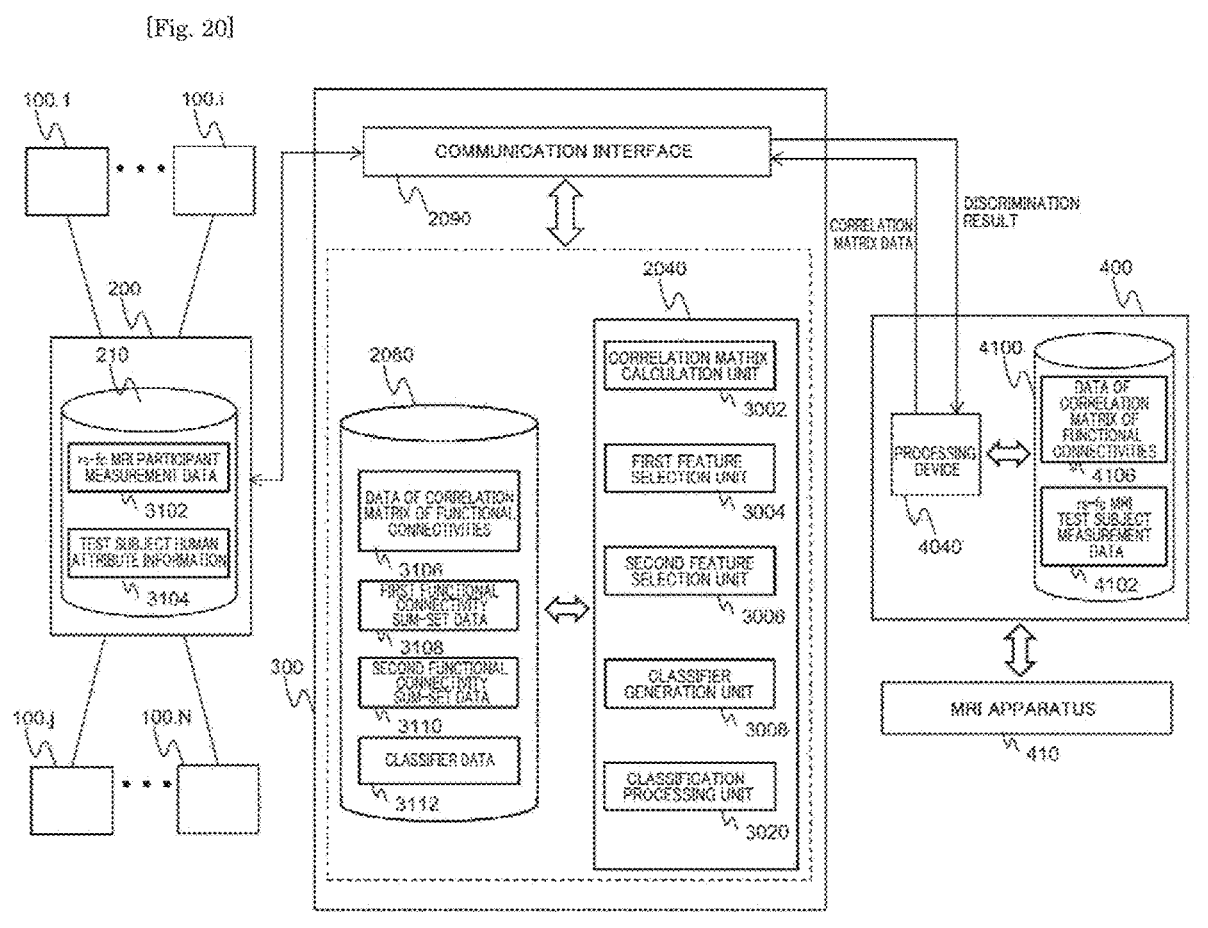

Another mode of the first embodiment relates to a classification device for a patient with depression. When depression is classified into a plurality of subclasses set in advance, the discriminating device 1 and the discriminating device 2 can be used as a classification device 1 and a classification device 2 (hereinafter collectively referred to as "classification device"), respectively, which are configured to assist the doctor in classifying a patient with depression. The classification device includes a processor and a storage device. That is, the processor of the discriminating device for classifying the patient with depression executes processing of generating, when the depressive symptom is classified into a plurality of subclasses set in advance, based on a program stored in the storage device, an indicator value for evaluating the depressive symptom for elements of a correlation matrix of functional connectivities measured for a subject in a resting state, comparing the indicator value with a reference range of the indicator value set in advance in accordance with a subclass for each functional connectivity, and determining that the subject has the subclass corresponding to the reference range including the indicator value. In this case, the configurations of the classification device 1 and the classification device 2 are similar to those of the discriminating device 1 and the discriminating device 2 described in the above-mentioned section "3.", and thus a description thereof is omitted here. FIG. 19 and FIG. 20 are functional block diagrams for illustrating the classification device 1 and the classification device 2. FIG. 19 and FIG. 20 are the same as FIG. 5 and FIG. 15, respectively, except that the discriminating processing unit 3010 is replaced with a classification processing unit 3020. The classification processing unit 3020 executes processing of classifying input data based on the classifier identified by the classifier data 3112, executes discrimination for classifying a patient with depression, and outputs a result.

The doctor uses the discrimination result for classifying a patient with depression, which is output from the classification device 1 or the classification device 2, as assistance information to classify the patient. In this sense, such a device can also be referred to as "classification assisting device".

6-2. Classification Method

A fifth embodiment of the present invention relates to a method of classifying a patient with depression. The discriminating method includes a step of generating, when depression is classified into a plurality of subclasses set in advance, an indicator value for evaluating a depressive symptom for elements of a correlation matrix of functional connectivities measured for a subject in a resting state, a step of comparing the indicator value with a reference range of the indicator value set in advance in accordance with a subclass for each functional connectivity, and a step of determining that the subject has the subclass corresponding to the reference range including the indicator value.

FIG. 18 is a flow chart for illustrating processing to be executed by the data processing unit 32 configured to generate information for discriminating a subclass of the depressive symptom based on fMRI data on a subject by using the generated classifier.

The CPU 2040 receives, for example, input of start of processing from the input unit 40 to execute Step S401 to Step S406 illustrated in FIG. 14, to thereby generate an indicator value. Next, in Step S701 illustrated in FIG. 18, the CPU 2040 compares the indicator value with a reference range of the indicator value set in advance in accordance with the subclass of depression. The subclass of depression is classified into subclasses of the melancholic MDD, the non-melancholic MDD, and the treatment-resistant MDD in terms of a clinical finding. Thus, for example, a classifier generated by setting the melancholic MDD as the "disease label" can be used to discriminate whether measurement data obtained from a subject whose brain activity has been measured corresponds to the disease label of the melancholic MDD. Similarly, a classifier generated by setting the non-melancholic MDD or the treatment-resistant MDD as the "disease label" can be used to discriminate whether measurement data obtained from a subject whose brain activity has been measured corresponds to the disease label of the non-melancholic MDD or the treatment-resistant MDD.

In Step S702, the CPU 2040 determines which subclass the indicator value generated in Step S406 of FIG. 15 corresponds to. Then, in Step S703, the CPU 2040 determines that the subject belongs to the subclass of depression determined in Step S702. The doctor uses information on the subclass output in this manner as assistance information for classification of a patient with depression, to thereby classify the patient. In this sense, such a method can also be referred to as "classification assisting method". All or a part of steps to be executed by the CPU 2040 may be manually performed except for the step of generating the indicator value.

Further, another mode of the fifth embodiment includes a program for causing a computer to execute processing including Step S701 to Step S703 described above, to thereby execute the function of the classification device. Another mode of the fifth embodiment includes a program for causing the computer to execute processing including Step S401 to Step S406 and Step S701 to Step S703 described above, to thereby execute the function of the classification device. Those programs may be stored in a storage medium, for example, a hard disk drive, a semiconductor memory element such as a flash memory, or an optical disc. The format of storage of a program into the storage medium is not limited as long as the CPU 2040 can read the program. The storage medium for storing a program is preferably a non-volatile storage medium.

7. Generation of Second Classifier and Discrimination of Therapeutic Effect of Using Second Classifier

7-1. Discriminating Device for Therapeutic Effect

A sixth embodiment of the present invention relates to a discriminating device for a therapeutic effect or a treatment assisting device, which is configured to execute classifier generation processing of generating a second classifier for discriminating a group of subjects among a plurality of subjects in whom a therapeutic effect given by treatment was shown and a group of subjects among the plurality of subjects in whom a therapeutic effect was not shown, and generate information serving as an indicator for assisting the doctor in determining the therapeutic effect.

The configuration of the discriminating device for a therapeutic effect is basically the same as that of FIG. 1, but the data processing unit 32 in FIG. 1 is replaced with a data processing unit 62 in the sixth embodiment. Further, in the discriminating device for a therapeutic effect, the configuration of the data processing unit 62 is basically the same as those of FIG. 1 and FIG. 2, but in the sixth embodiment, the storage unit 36, the control unit 42, the input unit 40, the interface unit 44, the data collection unit 46, the image processing unit 48, the display unit 38, and the display control unit 34 of FIG. 1 are replaced with a storage unit 66, a control unit 62, an input unit 70, an interface unit 74, a data collection unit 76, an image processing unit 78, a display unit 68, and a display control unit 64, respectively. Further, in FIG. 2, the computer main body 2010 of the data processing unit 32, the memory drive 2020, the disk drive 2030, the processor (CPU) 2040, the disk drive 2030, the memory drive 2020, the bus 2050, the ROM 2060, the RAM 2070, the non-volatile storage device 2080, and the communication interface 2090 are replaced with a computer main body 6010, a memory drive 6020, a disk drive 6030, a processor (CPU) 6040, a disk drive 6030, a memory drive 6020, a bus 6050, a RCM 6060, a RAM 6070, a non-volatile storage device 6080, and a communication interface 6090, respectively. The hardware of the data processing unit 62 is not particularly limited as described above, but a general-purpose computer can be used as the hardware.

(Generation of Classifier)

FIG. 23 is a functional block diagram for executing processing of generating the second classifier and discriminating processing by the generated second classifier.

The non-volatile storage device 6080 stores information on a signal obtained by using the MRI apparatus to measure, in advance and time-sequentially, a signal indicating a brain activity of a plurality of predetermined regions of each brain of a plurality of participants including healthy individuals and patients with depression who has received the treatment. The stored information is rs-fc MRI measurement data 6102 on a subject measured at the first time point, rs-fc MRI measurement data 6104 on a subject measured at the second time point, and a plurality of pieces of treatment data 6105 associated with respective subjects for which rs-fc MRI measurement data has been measured.

The treatment data 6105 contains information on the disease label and treatment history (e.g., treatment, administered drug name, dosage, or duration of administration) of a subject. The CPU 6040 executes processing of generating a classifier for identifying a group ("remitted group (remitted)") of subjects among a plurality of subjects in whom a therapeutic effect was shown and a group ("non-remitted group (non-remitted)") of subjects among the plurality of subjects in whom a therapeutic effect was not shown, based on the rs-fc MRI measurement data 6102 on a subject at the first time point, the rs-fc MRI measurement data 6104 on a subject at the second time point, and the treatment data 6105 on a subject. Thus, in this case, the disease label includes a "remitted label" and a "non-remitted label".

A first correlation measurement unit 6002 calculates, for each subject, the correlation matrix of functional connectivities of brain activities of a plurality of predetermined regions based on the rs-fc MRI measurement data 6102 on a subject at the first time point. Data on the calculated correlation matrix of functional connectivities is stored into the non-volatile storage device 6080 for each subject as first correlation measurement data 6106 on the correlation matrix of functional connectivities.

A second correlation measurement unit 6004 calculates, for each subject, the correlation matrix of functional connectivities of brain activities of a plurality of predetermined regions based on the rs-fc MRI measurement data 6104 on a subject at the second time point. Data on the calculated correlation matrix of functional connectivities is stored into the non-volatile storage device 6080 for each subject as second correlation measurement data 6108 on the correlation matrix of functional connectivities.

A second classifier generation unit 6008 acquires a regression expression based on a difference between the correlation at the first time point and the correlation at the second time point of the plurality of functional connectivities. The regression expression is stored into the non-volatile storage device 6080 as second classifier data 6020 for identifying the second classifier. A therapeutic effect discriminating processing unit 6100 executes processing of discriminating a therapeutic effect for input data based on the second classifier identified by the second classifier data 6020.

FIG. 21 is a flow chart for illustrating processing to be executed by the data processing unit 62 to generate the second classifier.

Now, a description is given of the processing illustrated in FIG. 23 in more detail with reference to FIG. 21.

In FIG. 21, when the data processing unit 62 receives, for example, input of start of processing from the input unit 70, and starts processing of generating the classifier (start), the data processing unit 62 reads the rs-fc MRI measurement data 6102 on each subject at the first time point, and measures a correlation at the first time point for each of the plurality of functional connectivities shown in Table 1 (Step S802). Measurement of this correlation is performed by calculating the Pearson correlation coefficient of each functional connectivity.

Next, the data processing unit 62 reads the rs-fc MRI measurement data 6104 on each subject at the second time point from the storage unit 66, and measures a correlation at the second time point for each of the plurality of functional connectivities shown in Table 1 for each subject (Step S803). Measurement of this correlation is performed by calculating the Pearson correlation coefficient of each functional connectivity.

Next, the data processing unit 62 calculates a difference between the correlation at the first time point and the correlation at the second time point for each of the first functional connectivity and the second functional connectivity, for example, among the plurality of functional connectivities shown in Table 1 of each subject (Step S804). The difference is calculated based on Expression (4) given below, for example.

[Math. 10]

$$\Delta \text{sign}(W)FC1 = \text{sign}(w_1) \cdot (FC1^{post} - FC1^{pre}) \quad (4)$$
$$\Delta \text{sign}(W)FC2 = \text{sign}(w_2) \cdot (FC2^{post} - FC2^{pre})$$

In Expression (4), FC1 represents a first connectivity strength in Table 1, and FC2 represents a second connectivity strength in Table 1. That is, as a result of calculation of a related weighted sum, a connectivity having the largest absolute value of weight is FC1, and a connectivity having the second largest absolute value of weight is FC2. Superscripts "post" and "pre" represent the second time point and the first time point, respectively. Typically, the first time point is a time point before treatment (before drug administration), and the second time point is a predetermined time point after start of the treatment (after start of drug administration). Further, "sign($w_1$)" indicates the sign of the weight of FC1, and "sign($w_2$)" indicates the sign of the weight of FC2. For example, as described later, the classifier created in FIG. 33f indicates Accuracy: 0.75, AUC: 0.79, Specificity: 0.88, and Sensitivity: 0.43.

Further, the data processing unit 62 acquires a regression expression for describing a relationship between the difference between the two correlations for each functional connectivity of each subject and an explanatory variable (label of "remitted group" and "non-remitted group") included in the treatment data 6105. The regression expression is not particularly limited, but can be acquired by linear regression analysis. It is possible to use this regression expression to generate a classifier configured to distinguish between a group of subjects in whom a therapeutic effect was shown and a group of subjects in whom a therapeutic effect was not shown, in a correlation state space (Step S804).

The term "correlation state space" herein refers to a space in which differences in strength (or differences in strength multiplied by sign of weight as required) between the first time point and the second time point of a plurality of functional connectivities are spanned as axes of the space. In the above-mentioned example, the correlation state space is a two-dimensional space.

As described above, for example, FIG. 33f is obtained by plotting a correlation state of a difference (Δsign(W)FC1) between correlations at the first time point and the second time point for the functional connectivity identification number 1 shown in Table 1 of each subject and a difference (Δsign(W)FC2) between correlations at the first time point and the second time point for the functional connectivity identification number 2 shown in Table 1 of each subject. A linear regression expression having a negative slope can be acquired in consideration of a relationship between the correlation between Δsign(W)FC1 and Δsign(W)FC2 and whether a therapeutic effect was shown in each subject. Then, on the basis of a regression straight line based on this linear regression expression, subjects distributed above the regression straight line and subjects distributed below the regression straight line can be identified as a group of subjects in whom a therapeutic effect was not shown and a group of subjects in whom a therapeutic effect was shown, respectively.

The doctor uses information on a therapeutic effect output in this manner as assistance information to determine a therapeutic effect for a patient with depression.

(Δsign(W)FC1 and Δsign(W)FC2 as Explanatory Variables)

In the above-mentioned example, the sign(W) of weight of each connectivity strength is used for convenience of display as a diagram. Change in strength of FC1 and FC2 through treatment (drug administration) is substantially important.

As shown in FIG. 33f, when remission and non-remission are not distinguished from each other, a change Δsign(W) FC1 in strength of the first functional connectivity and a change Δsign(W)FC2 in strength of the second functional connectivity do not have a correlation between the time before the start of treatment and the time after elapse of a predetermined period of time since start of treatment, and such a phenomenon as compensation for each change is not observed. In other words, those changes of the connectivity strength are independently of each other, which indicates that selection of variables for describing the effect of treatment is appropriate.

Thus, as described above, other functional connectivities can also be used by using functional connectivities for which the changes in strength through start of treatment can be regarded as being independently of each other, instead of using the first and second functional connectivities as described above. Further, a larger number of functional connectivities may be selected from among the functional connectivities shown in Table 1 as variables for describing the therapeutic effect.

(Discriminating Processing)

FIG. 22 is a flow chart for illustrating processing to be executed by the data processing unit 62 configured to discriminate a therapeutic effect based on rs-fc MRI data on a subject by using the second classifier generated in a seventh embodiment of the present invention.

The CPU 6040 receives, for example, input of start of processing from the input unit 70, to acquire, via the interface unit 64, rs-fc MRI measurement data 6113 on a subject in the resting state at the first time point from the MRI imaging unit 25 in Step S901.

The CPU 6040 executes preprocessing described in the above-mentioned section "2." in Step S902 and Step S903, extracts elements of a correlation matrix for all or a part of the functional connectivities shown in Table 1, and measures a correlation of each functional connectivity at the first time point.

In Step S904, the CPU 6040 acquires, via the interface unit 64, the rs-fc MRI measurement data 6113 on the subject in the resting state at the second time point from the MRI imaging unit 25.

The CPU 6040 executes preprocessing described in the above-mentioned section "2." in Step S905 and Step S906, extracts elements of a correlation matrix for all or a part of the functional connectivities shown in Table 1, and measures a correlation of each functional connectivity at the second time point.

Next, in Step S907, the CPU 6040 calculates, for each of the plurality of functional connectivities, a difference between the correlation of each functional connectivity at the first time point measured in Step S903 and the correlation of each functional connectivity at the second time point measured in Step S906.

The CPU 6040 inputs the difference calculated in Step S907 to the second classifier (Step S908), and determines whether a therapeutic effect was shown in the subject by using the second classifier (Step S908).

The method of measuring each correlation, the method of calculating the difference between correlations, and the discriminating method for a therapeutic effect are similar to those described in the method of generating the second classifier.

The first time point may be before start of treatment, or may be a time point after elapse of a predetermined period of time since start of the treatment. However, the first time point is preferably before start of treatment. Further, also when the treatment is finished once and after that the treatment is resumed, a period of time since the end of the treatment until the treatment is resumed may be defined as "before treatment". The second time point is not limited as long as the second time point is a time point after start of treatment and later than the first time point.

Further, in the seventh embodiment, Step S901 is required to be performed before Step S606. However, Step S902 and Step S903 are not required to be performed before Step S904. Step S902 and Step S903 are only required to be performed after Step S901 and at least somewhere before Step S907.

Further, another mode of the sixth embodiment includes using the second classifier, the discriminating device for a therapeutic effect, or the treatment assisting device for drug reprofiling.

7-2. Discriminating Method for Therapeutic Effect

The seventh embodiment relates to a discriminating method for a therapeutic effect using the second classifier. The discriminating method includes a step of measuring a first correlation between a plurality of functional connectivities inside a brain of a subject in a resting state at the first time point, a step of measuring a second correlation between the plurality of functional connectivities inside the brain of the same subject as the above-mentioned subject in the resting state at the second time point, and a step of discriminating a therapeutic effect for the subject by using the classifier based on a difference between the first correlation and second correlation of the plurality of functional connectivities of the subject. A specific procedure conforms to Step S901 to Step S909, but all or a part of the procedure may be manually performed.

Also in this case, discrimination information on a therapeutic effect output in this manner is used as assistance information to determine a therapeutic effect for a patient with depression.

Another mode of the seventh embodiment includes using the discriminating method for a therapeutic effect for drug reprofiling.

Further, another mode of the seventh embodiment includes a program for causing a computer to execute processing including Step S801 to Step S804 described above, to thereby execute the function of the second classifier. Another mode of the seventh embodiment includes a program for causing the computer to execute processing including Step S801 to Step S804 and Step S901 to Step S909 described above, to thereby execute the function of the discriminating device for a therapeutic effect. Another mode of the seventh embodiment includes a program for causing the computer to execute processing including Step S901 to Step S909 described above, to thereby execute the function of the discriminating device for a therapeutic effect. Those programs may be stored in a storage medium, for example, a hard disk drive, a semiconductor memory element such as a flash memory, or an optical disc. The format of storage of a program into the storage medium is not limited as long as the CPU 6040 can read the program. The storage medium for storing a program is preferably a non-volatile storage medium.

8. Determination of Therapeutic Effect for Classified Patient with Depression Using Second Classifier 8-1. Discriminating Device for Therapeutic Effect An eighth embodiment of the present invention relates to a device configured to cause the discriminating device for a therapeutic effect according to the sixth embodiment to discriminate a therapeutic effect by using rs-fc MRI data on a patient with depression classified by the classification device for a patient with depression described in the fourth embodiment.

That is, the eighth embodiment relates to a discriminating device for a therapeutic effect, which is configured to execute the first classifier generation processing described in the above-mentioned section "3.", the classification processing described in the above-mentioned section "6.", the second classifier generation processing described in the above-mentioned section "7.", first correlation measurement processing, second correlation measurement processing, and processing of discriminating a therapeutic effect for the subject by the second classifier.

Thus, the descriptions of the above-mentioned sections "3.", "6-1.", and "7-1." are incorporated in this embodiment. Another mode of the eighth embodiment includes using the discriminating device for a therapeutic effect for drug reprofiling.

8-2. Discriminating Method for Therapeutic Effect

A ninth embodiment of the present invention relates to a discriminating method for a therapeutic effect, which uses the second classifier, for a classified patient with depression.

FIG. 24 is a flow chart for discriminating a therapeutic effect for a classified patient with depression by using the second classifier.

In FIG. 24, Step S701 to Step S703 are the same as those of FIG. 18. Thus, the description of the above-mentioned section "6-2." is incorporated in this embodiment.

The CPU 6040 executes Step S921 to Step S929 for the subject whose subclass has been determined in Step S703 illustrated in FIG. 24. The respective steps of from Step S921 to Step S929 correspond to steps of from Step S901 to Step S909 described in the above-mentioned section "7-2." and illustrated in FIG. 22. Thus, the description of the above-mentioned section "7-2." is incorporated in this embodiment.

Although not particularly limited, in the above description, when the doctor has determined that the currently employed treatment (e.g., administration of specific drug) is not effective based on assistance of the therapeutic effect discriminating device, after that, the doctor can determine that another treatment (e.g., administration of another specific drug, neurofeedback, modified electroconvulsive therapy, or repetitive transcranial magnetic stimulation treatment) is to be used in combination, or the current treatment is to be changed to another treatment.

Another mode of the ninth embodiment includes using the discriminating method for a therapeutic effect for drug reprofiling.

Further, another mode of the eighth embodiment includes a program for causing a computer to execute processing including Step S921 to Step S929 described above, to thereby execute the function of the second classifier. Another mode of the eighth embodiment includes a program for causing the computer to execute processing including Step S701 to Step S703 and Step S921 to Step S929 described above, to thereby execute the function of the discriminating device for a therapeutic effect. Another mode of the seventh embodiment includes a program for causing the computer to execute processing including Step S401 to Step S406, Step S701 to Step S703 and Step S901 to Step S909 described above, to thereby execute the function of the discriminating device for a therapeutic effect. Those programs may be stored in a storage medium, for example, a hard disk drive, a semiconductor memory element such as a flash memory, or an optical disc. The format of storage of a program into the storage medium is not limited as long as the CPU 6040 can read the program. The storage medium for storing a program is preferably a non-volatile storage medium.

9. Neurofeedback

9-1. Brain Activity Training Device

A tenth embodiment of the present invention relates to a brain activity training device for giving feedback to a brain activity of a trainee, and performing training (neurofeedback training, which is also simply referred to as "training") so as to cause the brain activity to become closer to a correlation (connection) state of a healthy individual.

More generally, in terms of a relationship between brain activities of a group of healthy individuals and a group of patients, such a brain activity training device can not only be used for causing the functional connectivity state of the brain activity of the trainee to become closer to the functional connectivity state of the brain activity of a healthy individual, but also for causing the current functional connectivity state of the brain activity of the trainee to become closer to a target functional connectivity state of the brain activity. The functional connectivity state of the brain activity of a healthy individual and the target connectivity state of the brain activity are referred to as "target pattern" as described later. The target pattern is stored into a storage device 10080 or a memory drive 10020.

In this case, the trainee is preferably a subject (preferably subject with MDD, or more preferably, subject with melancholic MDD) assigned the label of "depressive symptom" by the discriminating device 1 for a depressive symptom, the discriminating device 2 for a depressive symptom, or the discriminating method for a depressive symptom described in the above-mentioned section "3.", a subject (preferably subject with MDD, or more preferably, subject with melancholic MDD) whose level of the depressive symptom is determined by the discriminating device and discriminating method for a level of a depressive symptom described in the above-mentioned section "4.", or a subject (preferably subject classified as MDD, or more preferably, subject classified as melancholic MDD) classified by the classification device and classification method for a patient with depression described in the above-mentioned section "6.". Thus, the description of the discriminating device 1 for a depressive symptom, the discriminating device 2 for a depressive symptom, or the discriminating method for a depressive symptom described in the above-mentioned section "3.", the description of the discriminating device and discriminating method for a level of a depressive symptom described in the above-mentioned section "4.", and the description of the classification device and classification method for a patient with depression described in the above-mentioned section "6." are incorporated in this embodiment.

FIG. 34 is a diagram for illustrating a concept of a configuration of the brain activity training device.

The configuration of the MRI apparatus 10 illustrated in FIG. 1 described above can be used as the hardware configuration of the brain activity training device, for example. The hardware configuration of the brain activity training device is basically the same as that of FIG. 1, but the data processing unit 32 in FIG. 1 is replaced with a data processing unit 102 in the tenth embodiment. Further, the configuration of the data processing unit 102 in the brain activity training device is basically similar to those of FIG. 1 and FIG. 2. However, in the tenth embodiment, in FIG. 1, the storage unit 36, the control unit 42, the input unit 40, the interface unit 44, the data collection unit 46, the image processing unit 48, the display unit 38, and the display control unit 34 are replaced with a storage unit 106, a control unit 112, an input unit 110, an interface unit 114, a data collection unit 116, an image processing unit 118, a display unit 108, and an display control unit 104, respectively. Further, in FIG. 2, the computer main body 2010 of the data processing unit 32, the memory drive 2020, the disk drive 2030, the processor (CPU) 2040, the disk drive 2030, the memory drive 2020, the bus 2050, the ROM 2060, the RAM 2070, the non-volatile storage device 2080, and the communication interface 2090 are replaced with a computer main body 10010, a memory drive 10020, a disk drive 10030, a processor (CPU) 10040, a disk drive 6030, a memory drive 6020, a bus 10050, a RCM 10060, a RAM 10070, a non-volatile storage device 10080, and a communication interface 10090, respectively. The hardware of the data processing unit 62 is not particularly limited as descried above, but a general-purpose computer can be used as the hardware.

The description of a method of driving the brain activity training device described below as an example is based on the assumption that the brain activity detecting apparatus for measuring time-series signals indicating brain activities by functional brain imaging uses real-time fMRI.

Now, a description is given of a flow of neurofeedback with reference to FIG. 34 and FIG. 38. First, the MRI apparatus 10 detects the brain activity of a trainee as time-series signals for a predetermined period of time, which indicate brain activities of a plurality of predetermined regions of the brain (Step S1001 of FIG. 38). The trainee preferably tries to increase a reward value described later during this period. Echo-planar imaging (EPI) is executed as fMRI.

Next, a CPU 10040 of the data processing unit 102 executes processing of reconstructing the taken image in real time.

As described in the first embodiment, the functional connectivities between regions of interest of the functional connectivity identification numbers ("ID" in Table 1) 1 to 12 shown in Table 1 are selected by feature selection for discrimination of the label of the "depressive symptom".

The trainee further selects and extracts at least one specific functional connectivity as a "functional connectivity to be trained" from among the above-mentioned 12 pairs of functional connectivities. Although not particularly limited, it is assumed that a "functional connectivity between left dorsolateral prefrontal cortex, and left precuneus and left posterior cingulate cortex" (connectivity of ID=1 in Table 1) having the largest degree of contribution to discrimination of the depression label is selected as the "functional connectivity to be trained" from among the functional connectivities shown in Table 1, for example. The term "degree of contribution" herein refers to an "absolute value of weight in related weighted sum".

In FIGS. 32, as described above, this connectivity is a connectivity having the largest degree of contribution among connectivities that change in a direction opposite to that of a healthy individual due to administration of the "antidepressant" as described above.

Only the connectivity of this ID=1 may be selected as the "functional connectivity to be trained", or other connectivities may be selected in addition to the connectivity of the ID=1. At this time, a connectivity of an ID=2 having the second largest degree of contribution may be selected as the functional connectivity to be selected in addition to the connectivity of the ID=1. In other cases, another connectivity that changes in the direction opposite to that of a healthy individual due to administration of the "antidepressant", for example, the connectivity of an ID=3, may be selected in addition to the connectivity of the ID=1. There may be one or more other functional connectivities to be selected in addition to the connectivity of the ID=1.

Further, the data processing unit 102 executes processing of calculating, for a region of interest corresponding to the "functional connectivity to be trained", a temporal correlation of the functional connectivity within a predetermined period of time (Step S1002 of FIG. 38).

That is, the data processing unit 102 first calculates the "degree of activity" of each region of interest based on pieces of fMRI data (signals) at n continuous measurement time points (n: natural number, n≥1) measured by fMRI in the resting state in real time. This degree of activity can be set to be an average value of measurement values at the n continuous measurement time points, for example. A period including the n continuous measurement time points is hereinafter referred to as a "sample step".

Then, the data processing unit 102 calculates, for the degree of activity of each sample step, a correlation (hereinafter referred to as "temporal correlation") of the degree of activity on a time axis by the following numerical expression for measurement windows in a predetermined period of time. The measurement window is a period of time including the degrees of activity (e.g., m degrees (m: natural number, m≥2)) of a plurality of sample steps continuous on the time axis.

$$\frac{\sum (x - \bar{x})(y - \bar{y})}{\sqrt{\sum (x - \bar{x})^2} \sqrt{\sum (y - \bar{y})^2}} \qquad \text{[Math. 11]}$$

In the expression given above, x represents the "degree of activity" of one region of interest of the "functional connectivity to be trained", and y represents the "degree of activity" of another region of interest of the "functional connectivity to be trained". Further, x (bar) (symbol representing "average" with "-" assigned to top of letter x is called "x (bar)". The same holds true for other letters) represents an average of the degrees of activity x within the measurement window as described above. The same holds true for "y (bar)". In the expression given above, Σ means taking a sum of the degrees of activity of m sample steps within the measurement window, for example. Further, although the measurement window is not particularly limited, the measurement window can be set to about ten to twenty seconds, for example.

The temporal correlation of the functional connectivity may take a positive or negative value as its sign.

Further, there may be a situation in which, for example, the sign of the temporal correlation of the functional connectivity is negative in the case of a "healthy individual" whereas the sign of the temporal correlation of the functional connectivity is positive in the case of a subject determined to have a "depressive symptom". It is to be understood that there may be an opposite case, or both signs may be the same. The sign of the temporal correlation of the functional connectivity and the size of the absolute value are collectively referred to as a "pattern of temporal correlation".

Further, for example, when a functional connectivity that has a negative temporal correlation is selected as the "functional connectivity to be trained" in the case of the "healthy individual", the "degree of similarity" between the temporal correlation of the functional connectivity to be trained of a trainee and the temporal correlation of a healthy individual can be calculated by the following function F1.

i) A function F1 that takes a constant value V1 when the sign of the temporal correlation of the functional connectivity to be trained of the trainee is positive, and takes a value V2 (>V1≥0) when the sign is negative, which increases the value V2 as the absolute value of the temporal correlation increases.

In contrast, when a functional connectivity that has a positive temporal correlation is selected as the "functional connectivity to be trained" in the case of the "healthy individual", the "degree of similarity" between the temporal correlation of the functional connectivity to be trained of the trainee and the temporal correlation of the healthy individual can be calculated by the following function F2.

ii) A function F2 that takes the constant value V1 when the sign of the temporal correlation of the functional connectivity to be trained of the trainee is negative, and takes the value V2 (>V1≥0) when the sign is positive, which increases the value V2 as the absolute value of the temporal correlation increases.

The "degree of similarity" is not limited to the above-mentioned example, and another function may be employed as long as the function is a function that increases the "degree of similarity" as the pattern becomes closer to the temporal correlation of the functional connectivity of a healthy individual in addition to the sign.

Further, although not particularly limited, when two or more "functional connectivities to be trained" are selected, an average value of degrees of similarity may be set as the "degree of similarity", or an average value of degrees of similarity weighted by the degree of contribution of each connectivity may be set as the "degree of similarity".

Further, the data processing unit 102 calculates a reward value in accordance with the degree of similarity calculated as described above (Step S1003 of FIG. 38). The reward value (score SC) becomes higher as the degree of similarity increases depending on the degree of similarity with a connectivity strength of the target brain activity.

The data processing unit 102 displays the calculated score SC on the presentation device 6, to thereby give feedback to a trainee 2 (Step S1004 of FIG. 38). Information to be fed back may be the score value itself, or may be a shape whose size changes depending on the magnitude of the value as shown in FIG. 35. Alternatively, other configurations may be employed as long as the information is an image that enables the trainee to recognize the magnitude of the score.

After that, the processing of from EPI imaging to score feedback is repeated in real time within a predetermined period of time.

FIG. 36 is a diagram for illustrating an example of a training sequence in neurofeedback.

As illustrated in FIG. 36, first, on a first day, the brain activity of a trainee in the resting state is measured in advance.

After that, training by neurofeedback is performed on the first day.

After that, neurofeedback training is performed also on second and third days.

On a fourth day (last day), after training by neurofeedback is performed, the subsequent brain activity of the trainee in the resting state is measured. The number of days for training may be smaller than or larger than this example.

Further, the brain activity of the trainee in the resting state is measured after elapse of a predetermined period of time, for example, after two months.

The therapeutic effect obtained by neurofeedback training can be determined by the discriminating device and discriminating method for a therapeutic effect using the first classifier described in the above-mentioned section "5.", or by generation of the second classifier and the discriminating method for a therapeutic effect using the second classifier described in the above-mentioned section "7."

Thus, the description of the discriminating device and discriminating method for a therapeutic effect using the first classifier described in the above-mentioned section "5.", or generation of the second classifier and the discriminating method for a therapeutic effect using the second classifier described in the above-mentioned section "7." is incorporated in this embodiment.

9-2. Computer Program for Controlling Brain Activity Training Device

Another mode of the tenth embodiment includes a computer program for executing processing of from Step S1001 to Step S1004 described above, and driving the brain activity training device. Those programs may be stored in a storage medium, for example, a hard disk drive, a semiconductor memory element such as a flash memory, or an optical disc. The format of storage of a program into the storage medium is not limited as long as the CPU 10040 can read the program. The storage medium for storing a program is preferably a non-volatile storage medium.

EXAMPLES

I. Data Collection and Evaluation Method

1. Data Collection Target

In order to select a patient with major depressive disorder (MDD) based on the standard of the Diagnostic and Statistical Manual of Mental Disorders (DSM)-IV, 105 patients gathered in Hiroshima University Hospital and clinics of Hiroshima city were subjected to screening by using Mini-international neuropsychiatric interview (M.I.N.I.). Patients with manic symptoms, psychotic symptoms, alcohol dependence or abuse, substance dependence or abuse, or antisocial personality disorder in the past or present day were excluded. Finally, 93 patients with the depressive symptom based on self-declaration were selected as a training data set for the MDD classifier. Before start of drug administration or within 0 to two weeks after start of drug administration under the condition described later, fMRI data on those patients was acquired. In the region, 145 healthy individuals were gathered, and took M.I.N.I. interviews, and individuals with no history of mental disorder were selected. An experiment in this Example was conducted through approval of the ethic committee of Hiroshima University. Further, prior to start of the experiment, all the participants were given written informed consent.

Further, depression cohorts were collected from completely independent four facilities.

The MDD includes three subtypes: the melancholic MDD, the non-melancholic MDD, and the treatment-resistant MDD. Now, in the following Example, a group including all the MDD patients, a group including patients with melancholic MDD, a group including patients with non-melancholic depression, a group including patients with treatment-resistant MDD, and a group of healthy individuals are set as a whole MDD group, a melancholic MDD group, a non-melancholic MDD group, a treatment-resistant MDD group, and a healthy control group, respectively.

A training data set for generating the melancholic MDD classifier is limited to a subtype (based on M.I.N.I.) of depression accompanied by a medium degree of the depressive symptom, for which the age and sex match those of the healthy control group, based on the Beck Depression Inventory (BDI). The number of patients and the number of healthy individuals (whose age and sex match those of patients and BDI-II score is smaller than 10) are set to be equal to each other so as not to cause a deviation among groups (Table 2a). Regarding a score of Japanese Adult Reading Test (JART) for evaluating an intelligence quotient (IQ), three pieces of lost data (one in melancholic MDD group and two in healthy control group for both of whole MDD group and melancholic MDD group) were found in the training data set, and two pieces of lost data were found in the treatment-resistant MDD group of the test data set. Regarding the BDI score, two pieces of lost data were found in the healthy control group only for the whole MDD group, and one piece of lost data was found in data after treatment with an antidepressant in the training data set.

In Table 2b, details of test data used for this Example are shown.

TABLE 2

| | a Training dataset | | | |
| --- | --- | --- | --- | --- |
| | All MDD and all controls (Hiroshima) | | Melancholic MDD and matched controls (Hiroshima) | |
| | MDD | HC | MDD | HC |
| No. of participants | 93 | 93 | 66 | 66 |
| Sex (Male/Female) | 50/43 | 44/49 | 40/26 | 32/34 |
| Age (Mean, SD) | 43.7 (11.9) | 39.3 (11.9) | 43.6 (12.7) | 43.4 (10.2) |
| Severity of depression (BDI-II) | 29.5 (8.6) | 4.1 (3.1) | 30.7 (8.4) | 3.8 (3.1) |
| IQ (JART) | 109.3 (10.3) | 112.6 (8.3) | 107.8 (10.9) | 111.8 (8.5) |
| Previous depressive episodes (single/recurrent) | 0.64 (0.96) | NA | 0.71 (1.03) | NA |
| Melancholia (%) | 74.2 | NA | 100 | NA |
| Comorbidity (Anxiety %) | 2.2 | NA | 2.2 | NA |
| Antidepressant (%) | 47 | NA | 45 | NA |

TABLE 2-continued

| | b Test dataset | | | | | | | | |
|---|---|---|---|---|---|---|---|---|---|
| | Independent Cohort All MDD (Chiba) | | Independent Cohort Melancholic MDD (Chiba) | | Antidepressant therapy Melancholic MDD (Hiroshima) | | Non-melancholic (Hiroshima) | | Treatment-resistant (Hiroshima) | |
| | MDD | HC | MDD | HC | Pre | Post | MDD | HC | MDD | HC |
| No. of participants | 15 | 47 | 11 | 40 | 28 | 28 | 24 | 24 | 25 | 28 |
| Sex (Male/Female) | 9/6 | 41/6 | 6/5 | 35/5 | 19/9 | 19/9 | 10/14 | 11/13 | 14/11 | 12/16 |
| Age (Mean, SD) | 39.7 | 24.4 | 38.7 | 24.1 | 43.7 | — | 42.7 | 31.4 | 44.7 | 44.4 |
| | (10.3) | (5.8) | (11.5) | (4.7) | (14.2) | | (9.8) | (10.3) | (10.0) | (8.6) |
| Severity of | 28.8 | 4.6 | 27.8 | 3.7 | 29.9 | 17.7 | 28.1 | 4.7 | 27.5 | 3.3 |
| depression (BDI-II) | (10.2) | (4.2) | (7.5) | (3.3) | (7.4) | (12.3) | (7.6) | (3.0) | (11.8) | (3.1) |
| IQ (JART) | NA | NA | NA | NA | 109.4 | — | 112.9 | 114.0 | 110.2 | 115.5 |
| | | | | | (11.8) | | (7.8) | (8.2) | (9.4) | (8.1) |
| Previous depressive | NA | NA | NA | NA | 0.9 | — | 0.4 | NA | 0.35 | NA |
| episodes (single/ | | | | | (1.1) | | (0.7) | | (0.49) | |
| recurrent) | | | | | | | | | | |
| Melancholia (%) | 73.3 | NA | 100 | NA | 100 | — | 0 | NA | 52.0 | NA |
| Comorbidity (Anxiety %) | NA | NA | NA | NA | 3.6 | — | 0 | NA | 7.1 | NA |
| Antidepressant (%) | NA | NA | NA | NA | 80 | — | 50 | NA | — | NA |

2. Generalization to Independent External Validation Cohort

An independent validation cohort (cohort of Chiba) was created in the National Institute of Radiological Sciences. The lifetime history of mental disorder was evaluated for participants based on M.I.N.I.

The MDD patients did not have a mental disorder as a complication, and the healthy control group did not have physical, neurological, or psychiatric disorders, and did not have a medical history of substance abuse in the past or present day. All the participants were given written informed consent before an experiment. The current experiment was approved by the institutional review boards of the radio-pharmaceuticals safety management committee and the National Institute of Radiological Sciences in accordance with the ethical standard defined by the Declaration of Helsinki in 1964 and the amendment thereto after 1964.

3. Evaluation of Depression and Depressive Symptom

The Beck Depression Inventory (BDI) was used for evaluating depression and a symptom of depression. Further, the Hamilton Rating Scale for Depression (HAMD) was also used for evaluation of a therapeutic effect.

4. Non-Melancholic MDD and Treatment-Resistant MDD

The non-melancholic MDD group includes all the MDDs of the BDI score of 17 or more. The treatment-resistant MDD refers to a person whose depressive symptom is not improved even when two or more types of antidepressants are administered among people who are diagnosed with MDD.

5. Evaluation of Classifier in Other Mental Disorders

As fMRI data on autism (ASD) patients and schizophrenia (SSD) patients, data described in the literature "Nature Communications|7:11254|DOI: 10.1038/ncomms 11254" by Yahata et al. was used. The ASD group was limited to persons to which antidepressants were not effective in order to suppress an influence due to complications of depression. The fMRI data was acquired under a resting state with opened eyes similarly to an MDD patient and a healthy individual.

6. Acquisition of fMRI Data

At the time of acquisition of fMRI data, the subject was asked to keep looking at a crosshair mark on the center of a monitor screen without thinking anything particular and sleeping in a scanning room with dim illumination. Details of a fMRI data acquisition condition in each facility are shown in Table 3.

TABLE 3

| Parameter | Training data Site 1 | Site 2 | Site 3 (+TRD) | Site 4 |
|---|---|---|---|---|
| Participants (Patients/HC) | 41/27 (49/41 for all MDD) | 4/19 (7/30) | 12/12 (all: 20/12, TRD: 25/28) | 8/9 (17/10) |
| MRI scanner | GE Signa HDxt | GE Signa HDxt | Siemens Magnetom | Siemens Verio |
| Magnetic field (T) | 3.0 | 3.0 | 3.0 | 3.0 |
| Field of view (mm) | 256 | 256 | 192 | 212 |
| Matrix | 64 × 64 | 64 × 64 | 64 × 64 | 64 × 64 |
| Number of slices | 32 | 32 | 38 | 40 |
| Number of volumes | 150 | 150 | 112 | 244 |
| In-plane resolution (mm) | 4.0 × 4.0 | 4.0 × 4.0 | 3.0 × 3.0 | 3.3 × 3.3 |
| Slice thickness (mm) | 4 | 4.0 | 3.0 | 3.2 |
| Slice gap (mm) | 0 | 0 | 0 | 0.8 |
| TR (ms) | 2,000 | 2,000 | 2,700 | 2,500 |
| TE (ms) | 27 | 27 | 31 | 30 |
| Total scan time (mm:ss) | 5:00 | 5:00 | 5:03 | 10:10 |
| Flip angle (deg) | 90 | 90 | 90 | 80 |
| Slice acquisition order | Ascending (Interleaved) | Ascending (Interleaved) | Ascending (Interleaved) | Ascending |

TABLE 3-continued

| | | | | |
|---|---|---|---|---|
| Instructions to participants and other imaging conditions | Please relax. Do not think of anything in particular. Do not sleep, but keep looking at the crosshair mark presented. The lights in the scan room were dimmed. | Same as Site 1 | Same as Site 1 | Same as Site 1 |

| Parameter | Test data Site 5 | ASD Site 6 | SCZ Site 7 |
|---|---|---|---|
| Participants (Patients/HC) | 11/40 (15/47) | 48/36 | 68/102 |
| MRI scanner | Siemens Verio | Philips Achieva/Siemens Magnetom Trio | Siemens Trio/Tim Trio |
| Magnetic field (T) | 3.0 | 3.0/3.0 | 3.0/3.0 |
| Field of view (mm) | 240 | 224/192 | 256/212 |
| Matrix | 64 × 64 | 64 × 64/64 × 64 | 64 × 48/64 × 64 |
| Number of slices | 33 | 45/33 | 30/40 |
| Number of volumes | 204 | 200/150 | 180/240 |
| In-plane resolution (mm) | 3.75 × 3.75 | 3.5 × 3.5/3.0 × 3.0 | 4.0 × 4.0/3.3 × 3.3 |
| Slice thickness (mm) | 3.8 | 3.5/3.5 | 4.0/3.2 |
| Slice gap (mm) | 0.5 | 0.0/0.0 | 0/0.8 |
| TR (ms) | 2,000 | 2,500/2,000 | 2,000/2,500 |
| TE (ms) | 25 | 30/30 | 30/30 |
| Total scan time (mm:ss) | 6:52 | 8:20/5:00 | 6:00/10:00 |
| Flip angle (deg) | 90 | 75/80 | 90/90 |
| Slice acquisition order | Ascending (Interleaved) | Ascending/Ascending (Interleaved) | Ascending/Ascending (Interleaved) |
| Instructions to participants and other imaging conditions | Same as Site 1 | Same as Site 1 except looking at the crosshair mark (i.e., all the subjects with eyes closed) | Same as Site 1 |

7. Preprocessing of fMRI Imaging Data and Correlation Between Regions

All the fMRI data was subjected to preprocessing by using the same method described in the literature by Yahata et al.

SPM8 (Wellcome Trust Center for Neuroimaging, University College London, UK) of the literature: Noriaki Yahata, Jun Morimoto, Ryuichiro Hashimoto, Giuseppe Lisi, Kazuhisa Shibata, Yuki Kawakubo, Hitoshi Kuwabara, Miho Kuroda, Takashi Yamada, Fukuda Megumi, Hiroshi Imamizu, Jose' E. Na'n ~ez Sr, Hidehiko Takahashi, Yasumasa Okamoto, Kiyoto Kasai, Nobumasa Kato, Yuka Sasaki, Takeo Watanabe & Mitsuo Kawato, "A small number of abnormal brain connections predicts adult autism spectrum disorder", Nature Communications, DOI: 10.1038/ncomms11254 Matlab R2014a (Mathworks Inc., USA) was used to preprocess the T1-weighted structural image and the resting state functional image. The functional image was preprocessed by slice timing correction and alignment to an average image. Next, a normalized parameter obtained by segmentation of a structural image synchronized by an average functional image was used to normalize the fMRI data, and resample the data in units of $2 \times 2 \times 2$ mm$^3$ voxels. Lastly, the functional image was smoothed with a 6-mm isotropic full-width half-maximum Gaussian kernel. After those steps, any volume (that is, functional image) due to extra head motion was removed by executing a scrubbing procedure based on relative change between frames of time-series data (refer to Table 4 for summary of head motion).

For each participant on each of 137 regions of interest (ROI) covering an entire cerebral cortex defined in terms of anatomy in Brainvisa Sulci Atlas (BSA; http://brainvisa), fMRI data was extracted chronologically. In this Example, the structural and functional images of cerebellum of a participant are not included in a facility 1, and thus cerebellum is not included in the ROI. After the data was subjected to a bandpass filter (0.008 Hz to 0.1 Hz), the following 9 parameters (6 head motion parameters after realignment, temporal fluctuation of white matter, temporal fluctuation of cerebrospinal fluid, fluctuation of whole brain) were subjected to linear regression.

A pairwise Pearson correlation among 137 ROIs was calculated to obtain a matrix of each of 9,316 functional connectivities (FC) of each participant.

TABLE 4

| | | Training data (Hiroshima) | | | Test data (Chiba) | | |
|---|---|---|---|---|---|---|---|
| | | HC | MDD | p | HC | MDD | p |
| Translation (in millimeter) | x | 0.010 ± 0.007 | 0.009 ± 0.007 | 1.550 | 0.013 ± 0.009 | 0.009 ± 0.005 | 0.919 |
| | y | 0.041 ± 0.026 | 0.040 ± 0.029 | 5.286 | 0.045 ± 0.021 | 0.044 ± 0.025 | 5.814 |
| | z | 0.035 ± 0.019 | 0.029 ± 0.019 | 0.391 | 0.028 ± 0.014 | 0.017 ± 0.005 | 0.072 |

TABLE 4-continued

| | | Training data (Hiroshima) | | | Test data (Chiba) | | |
|---|---|---|---|---|---|---|---|
| | | HC | MDD | p | HC | MDD | p |
| Rotation | x | 0.023 ± 0.011 | 0.021 ± 0.012 | 1.290 | 0.029 ± 0.014 | 0.018 ± 0.005 | 0.127 |
| (in millimeter) | y | 0.010 ± 0.005 | 0.008 ± 0.005 | 0.509 | 0.011 ± 0.006 | 0.007 ± 0.002 | 0.267 |
| | z | 0.009 ± 0.005 | 0.007 ± 0.003 | 0.401 | 0.012 ± 0.010 | 0.008 ± 0.003 | 1.750 |

II. Example 1: Selection of 12 Pairs of Functional Connectivities for Classification of Melancholic MDD In order to select 12 pairs of functional connectivities for classification of the melancholic MDD, rs-fMRI data of 66 melancholic MDD patients and 66 healthy individuals shown in Table 1a was used. The functional connectivity for classifying the melancholic MDD group was selected based on the procedure described in the embodiment in accordance with the method of creating the classifier for classifying autism (ASD) reported by the above-mentioned literature by Yahata et al.

This system uses the sparse canonical correlation analysis (L1-SCCA) subjected to L1 regularization and the sparse logistic regression (SLR). The SLR is not useful for classifying MDD, but has a capability of training the logistic regression model while at the same time trimming each functional connectivity in an objective manner. A certain amount of input was reduced by L1-SCCA before training by the SLR, and at the same time, the influence of a nuisance variable (NV) that may cause fatal overfitting (overtraining) was reduced. In this Example, the facility, the sex, and the age are included in the random variable, and thus an unrequired factor was removed by the L1-SCCA among those factors. In this method, nested feature selection using an inner loop and an outer loop as described later and a successive step of leave-one-out cross validation (LOOCV) were used to avoid information leakage and too optimistic results. As a result of the SLR, 54 pairs of functional connectivities were output (FIG. 26). Further, the LOOCV was performed to finally select the 12 pairs of functional connectivities (Table 5 and FIG. 26).

Whether the selected 12 pairs of functional connectivities FC were selected frequently with a large weight over an entire procedure of the outer loop was considered. This is important for stability and robustness of the 12 pairs of functional connectivities FC selected last.

For such consideration, the following expression:

[Math. 12]

$$c^k = \sum_{i=1}^{N} |w_i^k| \tag{5}$$

defines a cumulative absolute weight for k-th FC (k=1, 2, . . . , 9316).

In the expression given above, N represents the number of times of LOOCV (namely, number of subjects), and $w_i^k$ represents a weight related to the k-th functional connectivity FC of the i-th LOOCV.

The fact that the cumulative weight $c_i^k$ is a larger value means that the k-th functional connectivity FC contributes more to classification into the MDD and HC over the entire LOOCV.

TABLE 5

| ID | Name | Lat. | BSA atlas (Sulcus) | BA | rControl | rMDD | Weight |
|---|---|---|---|---|---|---|---|
| 1 | Precuneus/Posterior Cingulate Cortex | L | Internal parietal sulcus | 7, 23, 31 | −0.063 | 0.121 | 3.88 |
| | Middle Frontal Gyrus, Dorsolateral Prefrontal Cortex (DLPFC) | L | Intermediate frontal sulcus | 46 | | | |
| 2 | Supplementary Motor Area (SMA, Pre-SMA), Frontal Eye Fields, Dorsomedial Prefrontal Cortex | R | Median frontal sulcus | 6, 8, 9 | 0.175 | −0.017 | −3.34 |
| | Inferior Frontal Gyrus opercular part | L | Diagonal ramus of the lateral fissure | 44 | | | |
| 3 | Thalamus | L | Thalamus | — | 0.210 | 0.051 | −2.61 |
| | Anterior Cingulate Cortex, Posterior Cingulate Cortex | R | Subcallosal sulcus | 23, 24, 33 | | | |
| 4 | Precuneus | L | Superior parietal sulcus | 7 | −0.155 | 0.014 | 1.99 |
| | Inferior Frontal Gyrus opercular part | L | Diagonal ramus of the lateral fissure | 44 | | | |
| 5 | Inferior Frontal Gyrus opercular part | R | Inferior precentral sulcus | 44 | 0.408 | 0.288 | −2.38 |
| | Inferior Frontal Gyrus Triangular part | L | Inferior frontal sulcus | 45 | | | |
| 6 | Nucleus Accumbens | R | Accumbens | — | 0.010 | 0.134 | 2.22 |
| | Anterior Cingulate Cortex, Posterior Cingulate Cortex | R | Subcallosal sulcus | 23, 24, 33 | | | |
| 7 | Lingual Gyrus | L | Anterior intralingual sulcus | 18 | 0.074 | 0.163 | 2.75 |
| | Middle Occipital Gyrus | R | Lobe occipital | 19 | | | |
| 8 | Postcentral Gyrus (Gustatory Area) | R | Central sylvian sulcus | 43 | −0.137 | −0.004 | 1.73 |
| | Occipital Lobe (Visual Area) | R | Lobe occipital | 17, 18, 19 | | | |
| 9 | Superior Parietal Gyrus (Somatosensory Area) | L | Superior postcentral sulcus | 5 | 0.076 | −0.022 | −1.93 |
| | Inferior Temporal Gyrus, Fusiform Gyrus | L | Median occipito-terrporal lateral sulcus | 20, 37 | | | |
| 10 | Rolandic operculum, Supramarginal Gyrus (Auditory Area) | R | Posterior latera; fissure | 40, 41, 48 | 0.066 | 0.168 | 1.75 |
| | Orbitofrontal cortex, Insular Cortex, Inferior Frontal Gyrus Orbital part | R | Anterior lateral fissure | 12, 13, 47 | | | |

TABLE 5-continued

| ID | Name | Lat. | BSA atlas (Sulcus) | BA | rControl | rMDD | Weight |
|----|------|------|--------------------|-----|----------|------|--------|
| 11 | Occipital Lobe (Visual Association Area) | L | Posterior intra-lingual sulcus | 18 | −0.144 | −0.052 | 1.59 |
|    | Anterior Cingulate Cortex, Posterior Cingulate | L | Calloso-marginal posterior fissure | 5, 7, 23, 24, | | | |
|    | Cortex, Precuneus (Somatosensory Association | | | 31, 33 | | | |
|    | Area) | | | | | | |
| 12 | SMA, Pre-SMA, Frontal Eye Fields, DLPFC | R | Median frontal sulcus | 6, 8, 9 | 0.207 | 0.115 | −1.37 |
|    | Anterior Cingulate Cortex (ACC) | L | Calloso-marginal anterior fissure | 32 | | | |

In Table 7, "L" and "R" of "Lat." represent the left brain and the right brain in a distinguished manner. "BSA" represents Brodmann's area, and "BA" represents a number of the Brodmann's area. "rControl" represents a correlation coefficient for the healthy control group. "rMDD" represents a correlation coefficient for the melancholic MDD group. "Weight" represents the weight of a related weighted sum.

FIG. 25 shows the selected 12 pairs of functional connectivities and each weight.

Two functional connectivities with particularly large weights were left dorsolateral prefrontal cortex (DLPFC, BA46)-left posterior cingulate cortex (PCC)/precuneus and left inferior frontal gyrus (IFG opecular, BA44)-right DLPFC (BA9)/frontal eye field (FEF, BA8)/supplementary motor area (SMA, BA6). Those functional connectivities overlapped with Left DLPFC/IFG targeted by repetitive transcranial magnetic stimulation (rTMS) treatment of the MDD.

In this manner, a regression expression for classifying a melancholic MDD patient and a healthy individual, namely, a classifier, was created. Further, a related weighted sum (the associated weighted linear sum: WLS) was calculated as an indicator for determining whether each subject has the melancholic MDD or is healthy.

The distribution of WLS in the melancholic MDD group and the healthy control group is shown in FIG. 27*a*. The black bars indicate the melancholic MDD group, whereas the white bars indicate the healthy control group. The accuracy was 70% (sensitivity: 64%, specificity: 77%, AUC: 0.77; and p=0.049 in permutation test: FIG. 30*a*). The results indicate the fact that the classifier (hereinafter referred to as "first classifier in the present invention") constructed by the selected 12 pairs of functional connectivities can distinguish between a patient with melancholic MDD and a healthy individual.

Further, the classifier obtained by the above-mentioned method was also used to consider cohorts collected in Chiba (including 11 patients with melancholic MDD and 40 healthy individuals collected in Keio University Hospital). The result is shown in FIG. 27*b*. The accuracy of cohorts collected in Chiba was 65% (sensitivity: 64%, specificity: 65%, AUC: 0.62; and p=0.036 in permutation test: FIG. 30*b*). The classifier in the present invention also succeeded in classifying cohorts independent of training data into a patient with melancholic MDD and a healthy individual.

From the above-mentioned results, it has been considered that the classifier in the present invention can classify the melancholic MDD, and is also generalized.

III. Example 2: Application of Classifier in the Present Invention to Non-Melancholic MDD Group and Whole MDD Group FIG. 27*c* shows data obtained by creating the classifier in the present invention with each of the whole MDD group, the melancholic MDD group, and the non-melancholic MDD group serving as training data (vertical direction), and considering accuracy with each group serving as test data (horizontal direction). As a result of the LOOCV, for example, the classifier generated by the melancholic MDD group has the accuracy of 54% (sensitivity: 42%, specificity: 678, and AUC: 0.65) for the non-melancholic MDD. The accuracy of the LOOCV for the whole MDD group is 66% (sensitivity: 58%, specificity: 74%, and AUC: 0.74).

The results indicate the fact that the classifier having the whole MDD group as training data has a lower classification accuracy compared to the classifier having the melancholic MDD group as training data or the classifier having the melancholic MDD group as training data. Further, the whole MDD group was considered to include more various subtypes of MDDS.

FIG. 28*d*, FIG. 28*e*, FIG. 29*f*, FIG. 29*g*, and FIG. 29*h* show a smoothed histogram of the WLS and the AUC value, which were acquired for each subject of a melancholic MDD group (d), a non-melancholic MDD group (e), a treatment-resistant MDD group (f), an ASD group (g), and an SSD group (h). A significant difference was calculated by a Benjamini-Hochberg-corrected Kolmogorov-Smirnov test. WLS data of each group was normalized so as to match the median and standard deviation of the healthy control group. This normalization is not applied to quantitative analysis. The values of AUC=0.77 and p=$1.5\times10^{-5}$ were obtained for the melancholic MDD group-healthy control group (d). The values of AUC=0.65 and p=0.051 were obtained for the non-melancholic MDD group-healthy control group (e). The values of AUC=0.46 and p=0.54 were obtained for the treatment-resistant MDD group-healthy control group (f). The values of AUC=0.51 and p=0.74 were obtained for the autism group-healthy control group (g). The values of AUC=0.43 and p=0.038 were obtained for the schizophrenia group-healthy individual group (h).

IV. Example 3: Evaluation of Degree of Severity of Depression and Evaluation of Therapeutic Effect Using WLS Score A correlation between a BD score and a WLS score was verified to investigate whether the WLS score correlated with the degree of severity of depression. As shown in FIG. 31*a*, when a correlation between the BDI score and the WLS score was calculated for a group including the whole MDD group and the healthy control group, the value of r=0.655 and the value of p=0.001 in the permutation test were obtained at n=186, which indicates that both scores correlated with each other. Further, the value of r=0.188 and the value of p=0.046 in the permutation test were obtained at n=93 with focus on only the whole MDD group (FIG. 31*b*), which indicates that both scores relatively correlated with each other.

Next, whether an effect of escitalopram, which is a selective serotonin reuptake inhibitor (SSRI), can be evaluated by the WLS score was considered. A smoothed histogram of the WLS score of each of 24 remitted melancholic MDD patients shown in Table 1a, to whom escitalopram was administered for 6 weeks to 8 weeks, is shown in FIG. 31c. When an antidepressant is administered, the distribution of the WLS score was shifted toward the healthy control group. The value of AUC=0.72 and the value of p=0.008 in the Benjamini-Hochberg-corrected Kolmogorov-Smirnov test were obtained.

This result relates to a group, and does not indicate a relationship between the WLS and improvement of an individual. Thus, a relationship between $\Delta$WLS (specifically, $WLS_{post}$–$WLS_{pre}$) and $\Delta$BDI (specifically, $BDI_{post}$–$BDI_{pre}$), and a relationship between $\Delta$WLS and $\Delta$HAMD (specifically, $HAMD_{post}$–$HAMD_{pre}$) were considered. The significant difference was acquired by the permutation test. As shown in FIG. 31d, $\Delta$BDI and $\Delta$WLS correlated with each other significantly (r=0.373 and p=0.040), but $\Delta$HAMD and $\Delta$WLS did not correlate with each other (r=0.154 and p=0.237). A deviation between BDI and HAMD is already reported.

Example 5: Change of 12 Pairs of Functional Connectivities Through Treatment

Next, contribution to $\Delta$WLS was considered for each functional connectivity in order to consider an influence of SSRI (escitalopram) on each of the 12 pairs of functional connectivities.

Specifically, in preliminary and subsequent analysis of administration, the following numerical expression was used to calculate a contribution score of each functional connectivity.

$$c_i = w_i \left( \frac{\sum_{j=1}^{N} FC_{i,j}^{post}}{N} - \frac{\sum_{j=1}^{N} FC_{i,j}^{pre}}{N} \right) \qquad \text{[Math. 13]}$$

(In the expression given above, N represents the number of patients who have received the treatment, and $w_i$ represents the weight of the classifier.)

Further, in order to obtain a reference score, a similar contribution score between the MDD and the healthy control group was also calculated by the following numerical expression, to thereby calculate the contribution score.

$$s_i = w_i \left( \frac{\sum_{j=1}^{N} FC_{i,j}^{HC}}{N} - \frac{\sum_{j=1}^{N} FC_{i,j}^{MDD}}{M} \right) \qquad \text{[Math. 14]}$$

(In the expression given above, M represents the number of MDDs, and N represents the number of healthy controls.)

That is, $s_i$ represents a difference in average connectivity strength between the healthy control group and the MDD group weighted by the weight of the classifier. In the classifier, the MDD shows positivity (a positive score), and the healthy individual shows negativity (a negative score), and thus $s_i$ always takes a negative score. Further, in Expression 2, $$FC_i^{MDD}$$

represents reduction (a negative sign through subtraction). The fact that $c_i$ and $s_i$ take large negative values means that the contribution of $FC_i$ is large in the after-treatment-before-treatment healthy individual-MDD. In other words, the fact that $c_i$ becomes negative means that $FC_i$ after treatment becomes closer to the corresponding FC of a healthy individual. In contrast, the fact that $c_i$ becomes positive means that $FC_i$ after treatment becomes closer to the MDD. The numbers of members in the healthy control group and in the MDD group are different from each other, and thus the significant difference between $c_i$ and $s_i$ for each $FC_i$ is evaluated by a Welch's t-test. The Welch's t-test is calculated in accordance with the following numerical expression.

$$t_i = \frac{s_i - c_i}{\sqrt{\dfrac{\sigma_s^2}{N_s} - \dfrac{\sigma_c^2}{N_c}}} \qquad \text{[Math. 15]}$$

(where $\sigma_s^2$ represents the variance of samples of $s_i$, and is calculated as a sum of variances of $FC_i^{HC}$ and $FC_i^{MDD}$ ($\sigma_s^2 = \sigma_{HC}^2 + \sigma_{MDD}^2$) by using the law of total variance. Similarly, $\sigma_c^2$ is also calculated as a sum of variances of $FC_i^{post}$ and $FC_i^{pre}$ ($\sigma_c^2 = \sigma_{post}^2 + \sigma_{pre}^2$). $N_s = (N_{CTRL} + N_{MDD})/2$ and $N_c = (N_{post} + N_{pre})/2$ represent sizes of samples.)

The p-value of each test was adjusted for a plurality of comparisons by the Benjamini-Hochberg method. As shown in FIG. 32a, FC1 (i.e., DLPFC-Precuneus/PCC) exhibited the largest significant difference between $c_i$ and $s_i$. This indicates the fact that the FC1 has transitioned toward the MDD group, which is opposite to the healthy control group, after administration of an antidepressant.

Eight functional connectivities among the 12 pairs of the functional connectivities (functional connectivity identification number shown in Table C may be denoted by "FC #") for classification of the melancholic MDD transitioned toward the direction of the healthy control group, and became "normal". However, four pairs of functional connectivities of the FCs #1, 3, 9, and 12 transitioned toward the direction opposite to the healthy control group (FIG. 32a). Among those, the FC #1 (Left DLPFC-Left Precuneus/PCC FC) is a functional connectivity having the largest degree of contribution among the 12 pairs of functional connectivities. The significant difference in change of FC #1 through treatment was p=0.009 in pairwise comparison for classification of the melancholic MDD group and the healthy control group (FIG. 32a).

As a result of focusing on two primary functional connectivities (FC #1, FC #2) having the largest degree of contribution, a significant difference was observed after treatment (p=0.002 in corresponding t-test), whereas a difference was not observed before treatment (p=0.96). In a test by two-way analysis of variance, the functional connectivities of FC #1 and FC #2 have a significant temporal interaction through treatment (FC #number x time, F (1,23)=6.70, p=0.016), and a significant difference was not observed for each primary effect. However, a significant difference in transition was observed in a pairwise t-test between the FC #1 and the FC #2 after treatment (p=0.002). In all the diagrams of FIG. 32 and FIG. 33, transition toward the positive direction indicates transition toward the direction of the melancholic MDD, whereas transition toward the negative direction indicates transition toward the direction of the healthy individual. This is because the sign of the weight of the melancholic MDD classifier was multiplied by the FC or the difference in FC. As described above, the FC #1 has transitioned toward the positive direction after treatment of escitalopram, and thus whether a completely independent cohort results in the same result was verified. Eleven melancholic MDD patients (serotonin-norepinephrine reuptake inhibitor (SNRI) duloxetine was administered for 6 weeks to 8 weeks) gathered in Chiba were considered (FIG. 32c). There was no significant difference before treatment (n.s., p=0.77), whereas a difference in trend level between FC #1 and FC #2 (p=0.10) was observed in a paired t-test after treatment. Next, the changes of FC #1 and FC #2 at the time of administration of SSRI to healthy subjects (19 persons) were observed. A significant difference between FC #1 and FC #2 was observed after single administration of paroxetine (p=0.033). There was no difference before treatment (p=0.18), and a significant relation was not observed (FIG. 32d).

Further, an effect of antidepressant treatment was investigated by dividing patients among cohorts of Hiroshima, in whom a therapeutic effect was determined to be shown by a clinician, into a non-remitted patient (n=7) and a remitted patient (n=7). As a result, significant interactions among the remitted and non-remitted groups x functional connectivities of FC #1 and FC #2, x time points before and after treatment were observed (FIG. 33e, F (1,22)=8.86, p=0.007), which indicates that there is difference in pattern of treatment reaction between FC #1 and FC #2. Specifically, the value of FC #2 decreases after treatment with an antidepressant only in the remitted group (p=0.001), and a significant difference was observed in those values (p=0.019). Further, in the non-remitted group, although there was no difference before treatment, a significant difference between FC #1 and FC #2 was observed after treatment with an antidepressant (p=0.033).

The changes of FC #1 and FC #2 were plotted two-dimensionally for 24 patients in order to consider how FC #1 and FC #2 change in the remitted group and the non-remitted group (FIG. 33f).

The FC #1 and FC #2 were obtained by the following numerical expression.

$$\Delta\text{sign}(W)FC1 = \text{sign}(w_1) \cdot (FC1^{post} - FC1^{pre})$$ [Math. 16]

$$\Delta\text{sign}(W)FC2 = \text{sign}(w_2) \cdot (FC2^{post} - FC2^{pre})$$

$FC1^{post}$ represents FC1 after administration, $FC1^{pre}$ represents FC1 before administration, $FC2^{post}$ represents FC2 after administration, $FC2^{pre}$ represents FC2 before administration, and "sign" represents the sign of the weight of each functional connectivity. The accuracy of this expression was Accuracy: 0.75, AUC: 0.79, Specificity: 0.88, Sensitivity: 0.43.

As a result, the changes of FC #1 and FC #2 apparently contribute to remission. Meanwhile, a significant difference or correlation was not observed between the change of FC #1 and the change of FC #2 (p=0.57).

V. Example 4: Neurofeedback V-1. Selection of Target Functional Connectivity to be Used for FC Neurofeedback Training The first functional connectivity shown in Table 5 was selected as a target of neurofeedback in accordance with the following procedure.

First, a biomarker (Yamashita A, Hayasaka S, Lisi G, Ichikawa N, Takamura M, Okada G, Morimoto J, Yahata N, Okamoto Y, Kawato M, Imamizu H (2015) Common functional connectivity between depression and depressed mood. The 37th annual meeting of the Japanese society of biological psychiatry; 24-26 September; Tokyo, Japan.) for predicting the degree of severity of a depressive symptom based on the classifier in the present invention and the BDI score was constructed as a biomarker for rs-fc MRI.

The target functional connectivity was set to include the above-mentioned biomarker.

During neurofeedback training, participants tried to decrease the correlation of the target FC.

A total of 10 participants including 3 participants with MDD and 7 participants with subclinical depression participated in the training. The average value of BDI-II of participants with subclinical depression, which were measured at two different time points prior to the neurofeedback training, was larger than 10.

In the neurofeedback training, participants lied on their back in the fMRI apparatus, looked at a monitor in the apparatus via prism eyeglasses, and imagined that the connectivity indicator of the functional connectivity shown in FIG. 35 moved toward the negative direction.

The neurofeedback score was calculated in accordance with a publicly known method.

FIG. 37a shows aggregation of neurofeedback scores on respective training days of 3 MDD participants. The score indicates an increase tendency over 4 days of training. When the significance of the result was examined by using a multivariate regression model including two explanatory variables (each training day and training item) and one response variable (neurofeedback score), a significantly good effect was exhibited (95% confidence interval (CI) coefficient: 1.9-9.1) on the training day. In a t-text performed as subsequent comparison, a significantly high neurofeedback score was obtained on the last day for all the 3 MDD participants compared to the first day of training (t=4.01, P<0.001). Those results indicate the fact that all the MDD participants learned to induce a negative correlation of the target FC through training. Further, as shown in FIG. 37b, the Hamilton Rating Scale for Depression (HAMD) indicating the degree of severity of the depressive symptom decreased for all the 3 MDD participants after the training.

Similarly to the MDD participants, 7 participants with subclinical depression had a tendency of having an increased neurofeedback score during the training period (FIG. 37c). When the significance of this result was analyzed, the primary effect of the training day was significant in one-way analysis of variance (one-way ANOVA) (p=0.0046). In a subsequent comparison paired t-test, the neurofeedback score was significantly higher on the last day of training than on the first day of training. The BDI score after the training also had a tendency of decreasing (p=0.07). Further, as shown in FIG. 37d, five out of the 7 participants with subclinical depression changed the target rs-fc MRI toward the normal direction, and the amount of change in rs-fc MRI through the training significantly correlated with the BDI score (r=0.87, p=0.011).

As described above, half or more of the participants decreased the functional connectivity shown in Table 5, which correlated with the BDI score, through the training. Thus, it is indicated that the functional connectivity shown in Table 5 can be used as the target functional connectivity of neurofeedback training for improving the depressive symptom. Further, it is indicated that the functional connectivity shown in Table 5 can be used as a treatment method or biomarker for developing a neurofeedback training method for improving the depressive symptom.

V-2. Comparison to Other Antidepressant Treatment

The therapeutic effect on MDD obtained by the neurofeedback training method was compared to other treatment methods (administration of antidepressant, repetitive transcranial magnetic stimulation: rTMS, and modified electro-convulsive therapy: ECT intervention). The neurofeedback training method improved the therapeutic effect more than the other antidepressant treatments.

REFERENCE SIGNS LIST 2 subject, 6 display, 10 MRI apparatus, 11 magnetic field applying mechanism, 12 static magnetic field generating coil, 14 magnetic field gradient generating coil, 16 RF irradiating unit, 18 bed, 20 reception coil, 21 driving unit, 22 static magnetic field power supply, 24 gradient magnetic field power supply, 26 signal transmission unit, 28 signal reception unit, 30 bed driving unit, 32 data processing unit, 36 storage unit, 38 display unit, 40 input unit, 42 control unit, 44 interface unit, 46 data collection unit, 48 image processing unit, 50 network interface.

The invention claimed is:

1. A discriminating device comprising a processor configured to:

execute classifier generation processing of using information obtained by measuring, for a plurality of subjects, a correlation at a first time point of a plurality of functional connectivities selected from among functional connectivity identification numbers 1 to 12, and a correlation at a second time point of the plurality of functional connectivities, the second time point being set to be after start of treatment and later than the first time point, to thereby generate in advance a classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point;

calculate a first correlation of the plurality of functional connectivities inside a brain of a subject in a resting state at the first time point;

calculate a second correlation of the plurality of functional connectivities inside the brain of the same subject in the resting state at the second time point; and execute processing of determining a therapeutic effect on a patient with depression by discriminating a therapeutic effect on the subject by the classifier based on a difference between the first correlation and the second correlation of the plurality of functional connectivities of the subject, the functional connectivity identification numbers 1 to 12 as follows:

| Functional connectivity identification number 1 | Left side | Brodmann's area or region name: 7, 23, 31 |
|---|---|---|
| | Left side | Brodmann's area or region name: 46 |
| functional connectivity identification number 2 | Right side | Brodmann's area or region name: 6, 8, 9 |
| | Left side | Brodmann's area or region name: 44 |
| functional connectivity identification number 3 | Left side | Brodmann's area or region name: Thalamus |
| | Right side | Brodmann's area or region name: 23, 24, 33 |
| functional connectivity identification number 4 | Left side | Brodmann's area or region name: 7 |
| | Left side | Brodmann's area or region name: 44 |

-continued

| functional connectivity identification number 5 | Right side | Brodmann's area or region name: 44 |
|---|---|---|
| | Left side | Brodmann's area or region name: 45 |
| functional connectivity identification number 6 | Right side | Brodmann's area or region name: Nucleus accumbens |
| | Right side | Brodmann's area or region name: 23, 24, 33 |
| functional connectivity identification number 7 | Left side | Brodmann's area or region name: 18 |
| | Right side | Brodmann's area or region name: 19 |
| functional connectivity identification number 8 | Right side | Brodmann's area or region name: 43 |
| | Left side | Brodmann's area or region name: 17, 18, 19 |
| functional connectivity identification number 9 | Left side | Brodmann's area or region name: 5 |
| | Left side | Brodmann's area or region name: 20, 37 |
| functional connectivity identification number 10 | Right side | Brodmann's area or region name: 40, 41, 48 |
| | Right side | Brodmann's area or region name: 12, 13, 47 |
| functional connectivity identification number 11 | Left side | Brodmann's area or region name: 18 |
| | Left side | Brodmann's area or region name: 5, 7, 23, 24, 31, 33 |
| functional connectivity identification number 12 | Right side | Brodmann's area or region name: 6, 8, 9 |
| | Left side | Brodmann's area or region name: 32. |

2. The discriminating device according to claim 1, wherein the plurality of functional connectivities are a functional connectivity with the functional connectivity identification number 1 and a functional connectivity with the functional connectivity identification number 2.

3. The discriminating device according to claim 2, which is further configured for drug reprofiling.

4. The discriminating device according to claim 1, which is further configured for drug reprofiling.

5. A discriminating method for assisting in determination of a therapeutic effect on a patient with depression, the discriminating method comprising the steps of:

using information obtained by measuring, for a plurality of subjects, a correlation at a first time point of a plurality of functional connectivities selected from among functional connectivity identification numbers 1 to 12, and a correlation at a second time point of the plurality of functional connectivities, the second time point being set to be after start of treatment and later than the first time point, to thereby generate in advance a classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point;

measuring a first correlation of the plurality of functional connectivities inside a brain of a subject in a resting state at the first time point;

measuring a second correlation of the plurality of functional connectivities inside the brain of the same subject in the resting state at the second time point; and discriminating, by the classifier, a therapeutic effect on the subject based on a difference between the first correlation and the second correlation of the plurality of functional connectivities of the subject, the functional connectivity identification numbers 1 to 12 as follows:

| Functional connectivity identification number 1 | Left side | Brodmann's area or region name: 7, 23, 31 |
|---|---|---|
| | Left side | Brodmann's area or region name: 46 |
| functional connectivity identification number 2 | Right side | Brodmann's area or region name: 6, 8, 9 |
| | Left side | Brodmann's area or region name: 44 |
| functional connectivity identification number 3 | Left side | Brodmann's area or region name: Thalamus |
| | Right side | Brodmann's area or region name: 23, 24, 33 |
| functional connectivity identification number 4 | Left side | Brodmann's area or region name: 7 |
| | Left side | Brodmann's area or region name: 44 |
| functional connectivity identification number 5 | Right side | Brodmann's area or region name: 44 |
| | Left side | Brodmann's area or region name: 45 |
| functional connectivity identification number 6 | Right side | Brodmann's area or region name: Nucleus accumbens |
| | Right side | Brodmann's area or region name: 23, 24, 33 |
| functional connectivity identification number 7 | Left side | Brodmann's area or region name: 18 |
| | Right side | Brodmann's area or region name: 19 |
| functional connectivity identification number 8 | Right side | Brodmann's area or region name: 43 |
| | Left side | Brodmann's area or region name: 17, 18, 19 |
| functional connectivity identification number 9 | Left side | Brodmann's area or region name: 5 |
| | Left side | Brodmann's area or region name: 20, 37 |
| functional connectivity identification number 10 | Right side | Brodmann's area or region name: 40, 41, 48 |
| | Right side | Brodmann's area or region name: 12, 13, 47 |
| functional connectivity identification number 11 | Left side | Brodmann's area or region name: 18 |
| | Left side | Brodmann's area or region name: 5, 7, 23, 24, 31, 33 |
| functional connectivity identification number 12 | Right side | Brodmann's area or region name: 6, 8, 9 |
| | Left side | Brodmann's area or region name: 32. |

6. The discriminating method according to claim 5, which is configured for drug reprofiling.

7. A second classifier generating device comprising:

a processor configured to measure, for a plurality of subjects, a correlation at a first time point of a plurality of functional connectivities selected from among functional connectivity identification numbers 1 to 12, and a correlation at a second time point of the plurality of functional connectivities, the second time point being set to be after start of treatment and later than the first time point, to thereby generate a second classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point; and a storage device configured to store information for identifying the second classifier generated by the processor, the functional connectivity identification numbers 1 to 12 as follows:

| Functional connectivity identification number 1 | Left side | Brodmann's area or region name: 7, 23, 31 |
|---|---|---|
| | Left side | Brodmann's area or region name: 46 |
| functional connectivity identification number 2 | Right side | Brodmann's area or region name: 6, 8, 9 |
| | Left side | Brodmann's area or region name: 44 |
| functional connectivity identification number 3 | Left side | Brodmann's area or region name: Thalamus |
| | Right side | Brodmann's area or region name: 23, 24, 33 |
| functional connectivity identification number 4 | Left side | Brodmann's area or region name: 7 |
| | Left side | Brodmann's area or region name: 44 |
| functional connectivity identification number 5 | Right side | Brodmann's area or region name: 44 |
| | Left side | Brodmann's area or region name: 45 |
| functional connectivity identification number 6 | Right side | Brodmann's area or region name: Nucleus accumbens |
| | Right side | Brodmann's area or region name: 23, 24, 33 |
| functional connectivity identification number 7 | Left side | Brodmann's area or region name: 18 |
| | Right side | Brodmann's area or region name: 19 |
| functional connectivity identification number 8 | Right side | Brodmann's area or region name: 43 |
| | Left side | Brodmann's area or region name: 17, 18, 19 |
| functional connectivity identification number 9 | Left side | Brodmann's area or region name: 5 |
| | Left side | Brodmann's area or region name: 20, 37 |
| functional connectivity identification number 10 | Right side | Brodmann's area or region name: 40, 41, 48 |
| | Right side | Brodmann's area or region name: 12, 13, 47 |
| functional connectivity identification number 11 | Left side | Brodmann's area or region name: 18 |
| | Left side | Brodmann's area or region name: 5, 7, 23, 24, 31, 33 |
| functional connectivity identification number 12 | Right side | Brodmann's area or region name: 6, 8, 9 |
| | Left side | Brodmann's area or region name: 32. |

8. A method of generating a second classifier, the method comprising a step of measuring, for a plurality of subjects, a correlation at a first time point of a plurality of functional connectivities selected from among functional connectivity identification numbers 1 to 12, and a correlation at a second time point of the plurality of functional connectivities, the second time point being set to be after start of treatment and later than the first time point, to thereby generate in advance a classifier configured to distinguish between a group of subjects among the plurality of subjects in whom a therapeutic effect was shown and a group of subjects among the plurality of subjects in whom a therapeutic effect was not shown, in a correlation state space spanned by differences of the correlations of the plurality of functional connectivities at the first time point and the second time point, the functional connectivity identification numbers 1 to 12 as follows:

| Functional connectivity identification number 1 | Left side | Brodmann's area or region name: 7, 23, 31 |
|---|---|---|
| | Left side | Brodmann's area or region name: 46 |
| functional connectivity identification number 2 | Right side | Brodmann's area or region name: 6, 8, 9 |
| | Left side | Brodmann's area or region name: 44 |

-continued

| functional connectivity identification number 3 | Left side | Brodmann's area or region name: Thalamus |
| | Right side | Brodmann's area or region name: 23, 24, 33 |
| functional connectivity identification number 4 | Left side | Brodmann's area or region name: 7 |
| | Left side | Brodmann's area or region name: 44 |
| functional connectivity identification number 5 | Right side | Brodmann's area or region name: 44 |
| | Left side | Brodmann's area or region name: 45 |
| functional connectivity identification number 6 | Right side | Brodmann's area or region name: Nucleus accumbens |
| | Right side | Brodmann's area or region name: 23, 24, 33 |
| functional connectivity identification number 7 | Left side | Brodmann's area or region name: 18 |
| | Right side | Brodmann's area or region name: 19 |

-continued

| functional connectivity identification number 8 | Right side | Brodmann's area or region name: 43 |
| | Left side | Brodmann's area or region name: 17, 18, 19 |
| functional connectivity identification number 9 | Left side | Brodmann's area or region name: 5 |
| | Left side | Brodmann's area or region name: 20, 37 |
| functional connectivity identification number 10 | Right side | Brodmann's area or region name: 40, 41, 48 |
| | Right side | Brodmann's area or region name: 12, 13, 47 |
| functional connectivity identification number 11 | Left side | Brodmann's area or region name: 18 |
| | Left side | Brodmann's area or region name: 5, 7, 23, 24, 31, 33 |
| functional connectivity identification number 12 | Right side | Brodmann's area or region name: 6, 8, 9 |
| | Left side | Brodmann's area or region name: 32. |

* * * * *